US008586617B2

(12) United States Patent
Galley et al.

(10) Patent No.: US 8,586,617 B2
(45) Date of Patent: Nov. 19, 2013

(54) AMINOMETHYL-4-IMIDAZOLES

(75) Inventors: Guido Galley, Rheinfelden (DE); Annick Goergler, Colmar (FR); Katrin Groebke Zbinden, Liestal (CH); Roger Norcross, Olsberg (CH); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 1293 days.

(21) Appl. No.: 11/872,203

(22) Filed: Oct. 15, 2007

(65) Prior Publication Data
US 2008/0119535 A1    May 22, 2008

(30) Foreign Application Priority Data
Oct. 19, 2006 (EP) ..................... 06122586

(51) Int. Cl.
*A61K 31/417* (2006.01)
*C07D 233/64* (2006.01)

(52) U.S. Cl.
USPC ...................... 514/400; 548/335.5

(58) Field of Classification Search
None
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Elbe | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahle et al. | |
| 4,146,647 A | 3/1979 | Lafon | |
| 4,323,570 A | 4/1982 | Stenzel et al. | |
| 4,505,918 A | 3/1985 | Huff et al. | |
| 4,517,198 A * | 5/1985 | Kurkela et al. | 514/400 |
| 4,665,095 A | 5/1987 | Winn et al. | |
| 5,464,847 A | 11/1995 | Courtemanche et al. | |
| 5,610,174 A | 3/1997 | Craig et al. | |
| 5,658,938 A | 8/1997 | Geerts et al. | |
| 7,851,626 B2 | 12/2010 | Ding et al. | |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |
| 2008/0096903 A1 | 4/2008 | Chen et al. | |

FOREIGN PATENT DOCUMENTS

| | | |
|---|---|---|
| CA | 2246027 | 2/2000 |
| EP | 0 024 829 | 3/1981 |
| EP | 0 081 324 A2 | 6/1983 |
| EP | 0 125 410 | 11/1984 |
| EP | 0 166 937 | 1/1986 |
| EP | 0 331 374 | 9/1989 |
| EP | 0 424 059 | 4/1991 |
| EP | 0 576 350 A1 | 12/1993 |
| EP | 0 857 483 | 8/1998 |
| EP | 0 924 209 | 6/1999 |
| EP | 1 103 243 | 5/2001 |
| EP | 1 413 576 | 4/2004 |
| ES | 323 985 | 12/1966 |
| FR | 6 551 | 12/1968 |
| GB | 877306 | 9/1961 |
| GB | 1016514 | 1/1966 |
| JP | 63141969 | 12/1986 |
| WO | WO 96/22768 | 8/1996 |
| WO | WO 97/12874 | 4/1997 |
| WO | 97/31638 | 9/1997 |
| WO | WO 98/12183 | 3/1998 |
| WO | WO 01/30762 A1 | 5/2001 |
| WO | 01/51472 | 7/2001 |
| WO | WO 01/81334 | 11/2001 |
| WO | WO 02/22801 A2 | 3/2002 |
| WO | WO 02/40453 A | 5/2002 |
| WO | WO 02/076950 | 10/2002 |
| WO | WO 03/092374 | 11/2003 |
| WO | WO 2004/014898 | 2/2004 |
| WO | 2004/018419 | 3/2004 |
| WO | 2004/022544 | 3/2004 |
| WO | 2004/022561 | 3/2004 |
| WO | 2006/119411 | 11/2006 |
| WO | WO 2006/119411 | 11/2006 |
| WO | WO 2006/133216 | * 12/2006 |
| WO | WO 2007/024944 | 3/2007 |
| WO | 2007/084684 | 7/2007 |
| WO | WO 2007/085556 A2 | 8/2007 |
| WO | 2008/046756 | 4/2008 |
| WO | 2008/046757 | 4/2008 |
| WO | 2008/046758 | 4/2008 |

OTHER PUBLICATIONS

Hodson et al. Bioorganic & Medicinal Chemistry Letters 12 (2002) 3449-3452.*

(Continued)

*Primary Examiner* — Joseph McKane
*Assistant Examiner* — Alicia L Otton

(57) ABSTRACT

The present invention relates to amino-4-methyl imidazoles and pharmaceutically-acceptable salts thereof. The compound may be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

9 Claims, No Drawings

(56) References Cited

OTHER PUBLICATIONS

Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing $\alpha_{1A}$-Adrenoceptor Agonist, J. Med. Chem. (2004), 47: 3220-3235.
Amemiya et al., Synthesis and α-Adrenergic Activities of 2-and 4-Substituted Imidazoline and Imidazoline Analogues, J. Med. Chem. (1992), 35:750-755.
Bagley et al., Synthesis and $\alpha_2$-Adrenegeric Activities of Imidazole and Imidazolidine Analogues: In Vitro and In Vivo Selectivity, Medicinal Chemistry Research (1994), 4:346-364.
Branchek et al., Trace amine receptors as targets for novel therapeutics: legend, myth and fact, Curr. Opin. Phamacol. (2003), 3:90-97.
Bunzow et al., Amphetamine, 3,4-Methylenedioxymethamphetamine, Lysergic Acid Diethylamide, and Metabolites of the catecholamine Neurotransmitters Are Agonists of a Rat Trace Amine Receptor, Molecular Pharmacology (2001), 60: 1181-1188.
Carroll et al., In Vitro and In Vivo Characterization of Alpha-1A Selective Agonists and Their Utility for Stress Incontinence, Med. Chem. Res. (2004), 13:134-148.
De Bernardis et al., Conformationally Defined Adrenergic Agents. 3. Modifications to the Carbocyclic Ring of 5,6-Dihydroxy-1-(2-imidazolinyl)tetralin: Improved Separation of $\alpha_1$ and $\alpha_2$ Adrenergic Activities, J. Med. Chem. (1986), 29:1413-1417.
De Bernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at α—Adrenoceptors, J. Med. Chem. (1987), 30:1011-1017.
Faust et al., Antihypertensive Agents: Derivatives of 2-Imidazoline and 1,4,5,6-Tetrahydropyrimidine, J. Org. Chem. (1961), 26: 4044-4047.
Hirashima et al., Three-Dimensional Common-Feature Hypotheses for Octopamine Agonist 2-(Arylimino)imidazolidines, Bioorganic & Medicinal Chemistry (2002), 10:117-123.
Holt, A., Imidazoline binding sites on receptors and enzymes:Emerging targets for novel antidepressant drugs?, Journal of Psychiatry & Neuroscience (2003), 28:409-414.
Jetter et al., Synthesis of 4-Substituted Imidazoles via Palladium-Catalyzed Cross-Coupling Reactions, Synthesis (1998), 829-831.
Law et al., Benzylimidazolines as $h5-HT_{1B/1D}$ Serotonin Receptor Ligands: A Structure-Affinity Investigation, J. Med. Chem. (1998), 41:2243-2251.
Lee et al., 4-[(N-Imidazol-2-ylmethyl)aniline]pyranopyridine Analogs as Novel Anti-Angiogenic Agents, Bull. Korean Chem. Soc. (2005), 25: 619-628.
Lindemann et al., A renaissance in trace amines inspired by a novel GPCR family, Trends in Pharmacol. Sci. (2005), 26:274-281.
Lindemann et al., Trace amine-associated receptors form structurally and functionally distinct subfamilies of novel G protein-coupled receptors, Genomics (2005), 85: 372-385.
Matsunaga et al., $C_{17,20}$ inhibitors. Part 2: Design, synthesis and structure-activity relationships of (2-naphthylmethyl)-1H-imidazoles as novel $C_{17,20}$-lyase inhibitors, Bioorganic & Medicinal Chemistry (2004), 4314.
Matsunaga et al., Synthetic studies on $(1_S)$-6,7-dimethoxy-2-naphthyl)-1-(1H-imidazol-4-yl)2-methylpropan-1-ol as a selective $C_{17,20}$-lyase inhibitor, Tetrahedron: Asymmetry (2004), 15: 2021-2028.
McCormack et al., Autoradiographic Localization of Tryptamine Binding Sites in the Rat and Dog Central Nervous System, J. Neurosci. (1986), 6:94-101.
McLennan, P;L., The Hypothermic Effect of Clonidine and Other Imidazolidines in Relation to their Ability to Enter the Central Nervous System in Mice, European Journal of Pharmacology (1981), 69:477-482.
Mosseau et al., A high-affinity [$^3$H]tryptamine binding site in human brain, Prog. Brain Res. (1995), 106:285-291.
Nathanson, J.A.,Phenyliminoimidazolines: Characterization of a Class of Potent Agonists of Octopamine-Sensitive Adenylate Cylcase and Their Use in Understanding the Pharmacology of Octopamine Receptors, Amer. Soc. Pharmacology (1985), 28:254-268.
Ojida et al., Sterocontrolled synthesis of (1S)-1-(1H-imidazol-4-y1)-1-(6-methoxy-2-napthyl)-2-methylpropan-1-ol as a potent $C_{17,20}$-lyase inhibitor,Tetrahedron: Asymmetry (2004), 15: 1555-1559.
Olmos et al., Imidazolines stimulate release of insulin from RIN-5AH cells independently from imidazoline $I_1$ and $I_2$ receptors, European Journal of Pharmacology (1994), 262: 41-48.
Prisinzano et al., 2-(aniline)imidazolines and 2-(benzyl)imidazoline derivatives as $h5-HT_{1D}$ serotonin receptor ligands, Bioorganic & Medicinal Chemistry Letter (2004), 14:4697-4699.
Savola et al., Cardiovascular and Sedative α-Adrenoceptor Effects of Detomidine-like Arylalkyl Imidazoles and Associated Derivatives, Drug Res. (1988), 38:29-35.
Timmermans et al., Characterization of α-Adrenoceptor Populations. Quantitive Relationships between Cardiovascular Effects Initiated at Central and Peripheral α-Adrenoceptors, J. Med. Chem. (1981), 24:502-507.
Timmermans et al., Correlations between Central Hypotensive and Peripheral Hypertensive Effects of Structurally Dissimilar Alpha-Adrenoceptor Agonists, Life Sciences (1981), 28:653-660.
Turner et al., A Facile Route to Imidazol-4-yl Anions and Their Reaction with Carbonyl Compounds, J. Org. Chem. (1991), 56: 5739-5740.
Usdin, E. and M. Sandler, Eds., Psychopharmacology Series, vol. 1: Trace Amines and the Brain (1976), 1-281.
Wentland et al., Synthesis and Antidepressant Properties of Novel 2-Substituted 4,5-Dihydro-1H-imidazole Derivatives, J. Med. Chem. (1987), 30:1482-1489.
Zhang et al., Medetomidine Analogs as $\alpha_2$-Adrenegeric Ligands. 3. Synthesis and Biological Evaluation of a New Series of Medetomidine Analogs and Their Potential Binding Interactions with $\alpha_2$-Adrenoceptors Involving a "Methyl Pocket", J. Med. Chem. (1997), 40: 3014-3024.
Hodson, S.J., et al., Bioorganic & Medicinal Chemistry Letters, vol. 12, pp. 3449-3452 (2002) XP002307084.
Swett; Yellin, J. Med. Chem., vol. 13, No. 5, pp. 968-970 (1970) XP002464069.
Glenn, et al., J. Med. Chem., vol. 49, No. 19, pp. 5710-5727 (2006) XP002464070.
Chilean Office Action in Corresponding Appl. 2971-07 dated Oct. 18, 2010.
(English Translation of Jap Office Action in Corres Appl 817166 Dec. 6, 2011).
(*Translation Russian Office Action in Appl. No. 2009112496* Aug. 26, 2011).
(Translation of Korean Off Act for Corr App KR20020084091 Oct. 27, 2011).
(Peruvian Office Action in Corres. PE Appl. 1403Jan Jan. 6, 2012).
Farmacia de Remington (17th Edition),:2181-2184 ( 1987).

* cited by examiner

AMINOMETHYL-4-IMIDAZOLES

PRIORITY TO RELATED APPLICATION(S)

This application claims the benefit of European Patent Application No. 06122586.8, filed Oct. 19, 2006, which is hereby incorporated by reference in its entirety.

FIELD OF THE INVENTION

This application relates to compounds which have a good affinity to the trace amino associated receptors (TAARs), especially for TAAR1.

The invention relates also to processes for preparing such compounds, a pharmaceutical composition comprising such a compound, and a method for treating a disease or disorder in a patient comprising administering such a compound to a patient in need of such treatment.

BACKGROUND OF THE INVENTION

It has been found that the compounds of formula I have a good affinity to the trace amine associated receptors (TAARs), especially for TAAR1.

The compounds may be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The classical biogenic amines (serotonin, norepinephrine, epinephrine, dopamine, histamine) play important roles as neurotransmitters in the central and peripheral nervous system. Deutch, A. Y. and Roth, R. H. (1999) Neurotransmitters. In *Fundamental Neuroscience* (2nd edn) (Zigmond, M. J., Bloom, F. E., Landis, S. C., Roberts, J. L., and Squire, L. R., eds.), pp. 193-234, Academic Press. Their synthesis and storage, as well as their degradation and reuptake after release are tightly regulated. An imbalance in the levels of biogenic amines is known to be responsible for the altered brain function under many pathological conditions. Wong, M. L. and J. Licinio (2001)*Nat. Rev. Neurosci.*, 2, 343-351; Carlsson, A. et al. (2001)*Annu. Rev. Pharmacol. Toxicol*, 41, 237-260; Tuite, P., and J. Riss (2003) *Expert Opin. Invest. Drugs*, 12, 1335-1352; Castellanos, F. X. and R. Tannock (2002) *Nat. Rev. Neurosci.*, 3, 617-628.

A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines. Ursdin, Earl; Sandler, Merton; Editors. *Psychopharmacology Series, Vol. 1: Trace Amines and the Brain [Proceedings of a Study Group at the 14th Annual Meeting of the American College of Neuropsychopharmacology*, San Juan, Puerto Rico] (1976). Their disregulation has been linked to various psychiatric diseases like schizophrenia and depression and for other conditions like attention deficit hyperactivity disorder, migraine headache, Parkinson's disease, substance abuse and eating disorders Lindemann, L. and M. Hoener (2005) *Trends in Phamacol. Sci.* 26, 274-281; Branchek, T. A. and T. P. Blackburn (2003) *Curr. Opin. Pharmacol.*, 3, 90-97; Premont, R. T. et al. (2001) *Proc. Natl. Acad. Sci.* S. A. 98, 9474-9475.

For a long time, TA-specific receptors had only been hypothesized based on anatomically discrete high-affinity TA binding sites in the central nervous system of humans and other mammals. Mousseau, D. D. and R. F. Butterworth (1995) *Prog. Brain Res.* 106, 285-291; McCormack, J. K. et al. (1986) *J. Neurosci.* 6, 94-101. Accordingly, the pharmacological effects of TAs were believed to be mediated through the well known machinery of classical biogenic amines, by either triggering their release, inhibiting their reuptake or by "cross reacting" with their receptor systems. Premont, R. T. et al. (2001) *Proc. Natl. Acad. Sci. U.S.A.* 98, 9474-9475; Dyck, L. F. (1989) *Life Sci.* 44, 1149-1156; Paker, E. M. and L. X. Cubeddu (1988) *J. Pharmacol. Exp. Ther.* 245, 199-210. This view changed significantly with the recent identification of several members of a novel family of GPCRs, the trace amine associated receptors (TAARs). Lindemann, L. and M. Hoener (2005) *Trends in Pharmacol. Sci*, 26, 274-281; Lindemann, L. et al. (2005) *Genomics,* 85, 372-385. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies Lindemann, L. and M. Hoener (2005) *Trends in Pharmacol. Sci.* 26, 274-281; Lindemann, L. et al. (2005), *Genomics,* 85, 372-385. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

The present invention relates to compounds which have a good affinity to the trace amino associated receptors (TAARs), especially for TAAR1.

SUMMARY OF THE INVENTION

The present invention relates to a compound of formula I

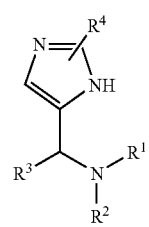

wherein:
R$^1$ is selected from the group consisting of:
  hydrogen;
  lower alkyl;
  —(CR$_2$)$_n$—OH;

—(CH$_2$)$_n$-aryl, optionally substituted by halogen, lower alkoxy, or lower alkyl substituted by halogen;
—(CH$_2$)$_n$-heteroaryl, optionally substituted by halogen, lower alkoxy, or lower alkyl substituted by halogen;
—(CR$_2$)$_n$— cycloalkyl, optionally substituted by hydroxyl;
—(CH$_2$)$_n$-heterocyclyl;
—(CH$_2$)$_n$—NH—S(O)$_2$CH$_3$;
—(CR$_2$)$_n$O-lower alkyl substituted by halogen; and
lower alkyl substituted by halogen;
each R is independently selected from the group consisting of hydrogen and lower alkyl;
R$^2$ is selected from the group consisting of:
  2,2-dioxo-2,3-dihydro-1H-benzo[c]thiophenyl;
  6,7-dihydro-5H-cyclopentapyrimidin-2-yl;
  2,2-difluoro-benzo[1,3]dioxol-5-yl;
  2,2,3,3-tetrafluoro-2,3-dihydro-benzo[1,4]dioxin-6-yl;
  aryl, optionally substituted by one or more substituents, selected from the group consisting of:
    halogen;
    lower alkyl;
    lower alkoxy;
    cycloalkyl;
    —(CH$_2$)$_n$-hydroxy;
    lower alkyl substituted by halogen;
    lower alkoxy substituted by halogen;
    —S(O)$_2$-lower alkyl;
    —(CH$_2$)$_n$—S(O)$_2$—NH-lower alkyl;
    —(CH$_2$)$_n$—O-lower alkyl;
    nitro;
    amino;
    cyano;
    —NHC(O)-lower alkyl;
    —C(O)NH-lower alkyl;
    —O-tetrahydro-naphthalenyl;
    —(CH$_2$)$_n$-aryl, optionally substituted by halogen, aryloxy optionally substituted by halogen, lower alkoxy, or lower alkyl substituted by halogen;
    —CH=CH-aryl optionally substituted by halogen;
    —(CH$_2$)$_n$—O-aryl optionally substituted by halogen, lower, or lower alkyl substituted by halogen;
    —O—(CH$_2$)$_n$-aryl, optionally substituted by halogen;
    —(CH$_2$)$_n$-heteroaryl, optionally substituted by =O;
    —(CH$_2$)$_n$—O-heteroaryl;
    —(CH$_2$)$_n$-heterocyclyl, optionally substituted by =O;
    —(CH$_2$)$_n$—O-heterocyclyl, optionally substituted by lower alkyl;
    —S-aryl;
    —CH(OH)-aryl;
    —C(CH$_3$)$_2$-aryl;
    —NR-aryl; and
    2-oxo-2H-pyridin-1-yl; and
  heteroaryl, optionally substituted by one or more substituents, selected from the group consisting of:
    halogen;
    lower alkyl;
    lower alkoxy;
    cycloalkyl;
    —(CH$_2$)$_n$-hydroxy;
    lower alkyl substituted by halogen;
    lower alkoxy substituted by halogen;
    —S(O)$_2$-lower alkyl;
    —(CH$_2$)$_n$—S(O)$_2$—NH-lower alkyl;
    —(CH$_2$)$_n$—O-lower alkyl;
    nitro;
    amino;
    cyano;
    —NHC(O)-lower alkyl;
    —C(O)NH-lower alkyl;
    —O-tetrahydro-naphthalenyl;
    —(CH$_2$)$_n$-aryl, optionally substituted by halogen, aryloxy optionally substituted by halogen, lower alkoxy, or lower alkyl substituted by halogen;
    —CH=CH-aryl optionally substituted by halogen;
    —(CH$_2$)$_n$—O-aryl optionally substituted by halogen, lower alkoxy, or lower alkyl substituted by halogen;
    —O—(CH$_2$)$_n$-aryl, optionally substituted by halogen;
    —(CH$_2$)$_n$-heteroaryl, optionally substituted by =O;
    —(CH$_2$)$_n$—O-heteroaryl;
    —(CH$_2$)$_n$-heterocyclyl, optionally substituted by =O;
    —(CH$_2$)$_n$—O-heterocyclyl, optionally substituted by lower alkyl;
    —S-aryl;
    —CH(OH)-aryl;
    —C(CH$_3$)$_2$-aryl;
    —NR-aryl; and
    2-oxo-2H-pyridin-1-yl;
R$^3$ is selected from the group consisting of: hydrogen and lower alkyl;
R$^4$ is selected from the group consisting of: hydrogen and lower alkyl; and
n is 0, 1, 2, 3 or 4;
and
to a pharmaceutically active salt of the above compound, with the proviso that the compound is not:
4-phenylaminomethyl-imidazol;
benzyl-(3H-imidazol-4-ylmethyl)-phenyl-amine;
(1H-imidazol-4-ylmethyl)-(4-methoxy-phenyl)-amine;
(3,4-dichloro-phenyl)-(1H-imidazol-4-ylmethyl)-amine;
(4-chloro-phenyl)-(1H-imidazol-4-ylmethyl)-amine;
(4-bromo-phenyl)-(1H-imidazol-4-ylmethyl)-amine;
(3,5-dichloro-phenyl)-(1H-imidazol-4-ylmethyl)-amine; or
(3-chloro-phenyl)-(1H-imidazol-4-ylmethyl)-amine.

A further aspect of the present invention are processes for the preparation of the above compound.

Yet another aspect of the present invention is a pharmaceutical composition comprising the above compound or pharmaceutically-acceptable salt thereof.

Yet another aspect of the present invention is a method for treating a disease or disorder in a patient comprising administering the above compound, or pharmaceutically-acceptable salt thereof, to a patient in need of such treatment.

DETAILED DESCRIPTION OF THE INVENTION

The present invention relates to a compound of formula I

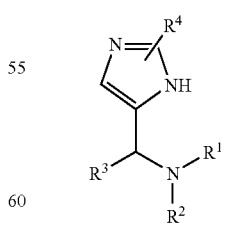

wherein:
R$^1$ is selected from the group consisting of:
  hydrogen;
  lower alkyl;
  —(CR$_2$)$_n$—OH;

—(CH$_2$)$_n$-aryl, optionally substituted by halogen, lower alkoxy, or lower alkyl substituted by halogen;
—(CH$_2$)$_n$-heteroaryl, optionally substituted by halogen, lower alkoxy, or lower alkyl substituted by halogen;
—(CR$_2$)$_n$— cycloalkyl, optionally substituted by hydroxyl;
—(CH$_2$)$_n$-heterocyclyl;
—(CH$_2$)$_n$—NH—S(O)$_2$CH$_3$;
—(CR$_2$)$_n$O-lower alkyl substituted by halogen; and
lower alkyl substituted by halogen;
each R is independently selected from the group consisting of hydrogen and lower alkyl;
R$^2$ is selected from the group consisting of:
  2,2-dioxo-2,3-dihydro-1H-benzo[c]thiophenyl;
  6,7-dihydro-5H-cyclopentapyrimidin-2-yl;
  2,2-difluoro-benzo[1,3]dioxol-5-yl;
  2,2,3,3-tetrafluoro-2,3-dihydro-benzo[1,4]dioxin-6-yl;
  aryl, optionally substituted by one or more substituents, selected from the group consisting of:
    halogen;
    lower alkyl;
    lower alkoxy;
    cycloalkyl;
    —(CH$_2$)$_n$-hydroxy;
    lower alkyl substituted by halogen;
    lower alkoxy substituted by halogen;
    —S(O)$_2$-lower alkyl;
    —(CH$_2$)$_n$—S(O)$_2$—NH-lower alkyl;
    —(CH$_2$)$_n$—O-lower alkyl;
    nitro;
    amino;
    cyano;
    —NHC(O)-lower alkyl;
    —C(O)NH-lower alkyl;
    —O-tetrahydro-naphthalenyl;
    —(CH$_2$)$_n$-aryl, optionally substituted by halogen, aryloxy optionally substituted by halogen, lower alkoxy, or lower alkyl substituted by halogen;
    —CH=CH-aryl optionally substituted by halogen;
    —(CH$_2$)$_n$—O-aryl optionally substituted by halogen, lower, or lower alkyl substituted by halogen;
    —O—(CH$_2$)$_n$-aryl, optionally substituted by halogen;
    —(CH$_2$)$_n$-heteroaryl, optionally substituted by =O;
    —(CH$_2$)$_n$—O-heteroaryl;
    —(CH$_2$)$_n$-heterocyclyl, optionally substituted by =O;
    —(CH$_2$)$_n$—O-heterocyclyl, optionally substituted by lower alkyl;
    —S-aryl;
    —CH(OH)-aryl;
    —C(CH$_3$)$_2$-aryl;
    —NR-aryl; and
    2-oxo-2H-pyridin-1-yl; and
  heteroaryl, optionally substituted by one or more substituents, selected from the group consisting of:
    halogen;
    lower alkyl;
    lower alkoxy;
    cycloalkyl;
    —(CH$_2$)$_n$-hydroxy;
    lower alkyl substituted by halogen;
    lower alkoxy substituted by halogen;
    —S(O)$_2$-lower alkyl;
    —(CH$_2$)$_n$—S(O)$_2$—NH-lower alkyl;
    —(CH$_2$)$_n$—O-lower alkyl;
    nitro;
    amino;
    cyano;
    —NHC(O)-lower alkyl;
    —C(O)NH-lower alkyl;
    —O-tetrahydro-naphthalenyl;
    —(CH$_2$)$_n$-aryl, optionally substituted by halogen, aryloxy optionally substituted by halogen, lower alkoxy, or lower alkyl substituted by halogen;
    —CH=CH-aryl optionally substituted by halogen;
    —(CH$_2$)$_n$—O-aryl optionally substituted by halogen, lower alkoxy, or lower alkyl substituted by halogen;
    —O—(CH$_2$)$_n$-aryl, optionally substituted by halogen;
    —(CH$_2$)$_n$-heteroaryl, optionally substituted by =O;
    —(CH$_2$)$_n$—O-heteroaryl;
    —(CH$_2$)$_n$-heterocyclyl, optionally substituted by =O;
    —(CH$_2$)$_n$—O-heterocyclyl, optionally substituted by lower alkyl;
    —S-aryl;
    —CH(OH)-aryl;
    —C(CH$_3$)$_2$-aryl;
    —NR-aryl; and
    2-oxo-2H-pyridin-1-yl;
R$^3$ is selected from the group consisting of: hydrogen and lower alkyl;
R$^4$ is selected from the group consisting of: hydrogen and lower alkyl; and
n is 0, 1, 2, 3 or 4;
and to a pharmaceutically active salt of the above compound, with the proviso that the compound is not:
4-phenylaminomethyl-imidazol;
benzyl-(3H-imidazol-4-ylmethyl)-phenyl-amine;
(1H-imidazol-4-ylmethyl)-(4-methoxy-phenyl)-amine;
(3,4-dichloro-phenyl)-(1H-imidazol-4-ylmethyl)-amine;
(4-chloro-phenyl)-(1H-imidazol-4-ylmethyl)-amine;
(4-bromo-phenyl)-(1H-imidazol-4-ylmethyl)-amine;
(3,5-dichloro-phenyl)-(1H-imidazol-4-ylmethyl)-amine; or
(3-chloro-phenyl)-(1H-imidazol-4-ylmethyl)-amine.

Furthermore, the invention includes all racemic mixtures, all their corresponding enantiomers and/or optical isomers. In addition, all tautomeric forms of compounds of formula I are also encompassed by the present invention.

Such compounds have a good affinity to the trace amino associated receptors (TAARs), especially for TAAR1 and may be used in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

In preferred embodiments, the compounds of the present invention, or their pharmaceuticaly-accpetable salts, are used for treating depression, psychosis, Parkinson's disease, anxiety and attention deficit hyperactivity disorder (ADHD).

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a substituent in which an alkyl group is attached via an oxygen atom to the remainder of the molecule.

As used herein, the term "cycloalkyl" denotes a saturated carbon ring containing 3 to 7 carbon atoms, for example cyclopropyl, cyclohexyl and the like.

As used herein, the term "lower alkyl substituted by halogen" denotes a saturated straight- or branched-chain group containing from 1 to 7 carbon atoms wherein one or more hydrogen atoms are replaced by a halogen atom, for example —CH$_2$F, —CF$_3$, As used herein, the term "lower alkyl substituted by halogen" denotes an alkyl group as defined above, wherein at least one hydrogen atom is replaced by halogen, for example —CF$_3$, —CHF$_2$, —CH$_2$F, —CH$_2$CF$_3$, —CF$_2$CHF$_2$, —CF$_2$CF$_3$, —CH$_2$CH$_2$CF$_3$, —CH$_2$CF$_2$CF$_3$ and the like.

As used herein, the term "lower alkoxy substituted by halogen" denotes a lower alkoxy group as defined above wherein one or more hydrogen atoms are replaced by a halogen atom, for example —OCH$_2$F, —OCF$_3$, —OCF$_2$CF$_3$, —OCH$_2$CH$_2$CF$_3$, and —OCH$_2$CF$_2$CF$_3$.

As used herein, the term "lower alkyl substituted by halogen" denotes an alkyl group as defined above, wherein at least one hydrogen atom is replaced by halogen, for example —CF$_3$, —CHF$_2$, —CH$_2$F, —OCH$_2$CF$_3$, —OCF$_2$CHF$_2$ and the like.

As used herein, the term "aryl" denotes a carbon ring or ring system, wherein at least one ring is aromatic in nature, for example phenyl, naphthyl, or indanyl.

As used herein, the term "heteroaryl" denotes an aromatic ring or a ring system selected from the group consisting of quinolinyl, pyrazinyl, thiophenyl, pyrrolyl, imidazolyl, thiazolyl, pyrazolyl, pyridinyl, pyrimidinyl, benzofuranyl, benzo[1.3]dioxolyl and indolyl.

As used herein, the term "heterocyclyl" denotes a non-aromatic ring group selected from the group consisting of morpholinyl, pyrrolidinyl, [1.3]dioxalanyl, tetrahydrofuranyl, tetrahydropyranyl, piperidinyl, and oxetanyl.

The term "halogen" denotes chlorine, iodine, fluorine or bromine.

The term "thiophenyl" denotes an aromatic ring containing 5 members of which 4 are carbon atoms and one is a sulfur atom.

The term "pharmaceutically acceptable salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

In an embodiment of the present invention, the compound is a compound of formula IA

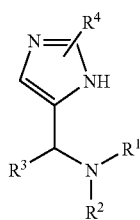

IA wherein:
$R^1$ is selected from the group consisting of:
  hydrogen;
  lower alkyl;
  —(CH$_2$)$_n$-aryl, optionally substituted by halogen, lower alkoxy, or lower alkyl substituted by halogen;
  —(CR$_2$)$_n$— cycloalkyl, optionally substituted by hydroxyl;
  —(CR$_2$)$_n$—OH;
  —(CH$_2$)$_n$-heterocyclyl;
  —(CH$_2$)$_n$—NH—S(O)$_2$CH$_3$;
  —(CR$_2$)$_n$O-lower alkyl; and
  lower alkyl substituted by halogen;
each R is independently selected from the group consisting of: hydrogen and lower alkyl;
$R^2$ is selected from the group consisting of:
  aryl, optionally substituted by one or more substituents, selected from the group consisting of:
    halogen;
    lower alkyl;
    lower alkoxy;
    —(CH$_2$)$_n$-hydroxy;
    lower alkyl substituted by halogen;
    lower alkoxy substituted by halogen;
    —S(O)$_2$-lower alkyl;
    —(CH$_2$)$_n$—S(O)$_2$—NH-lower alkyl;
    —(CH$_2$)$_n$—O-lower alkyl;
    nitro;
    amino;
    —NHC(O)-lower alkyl;
    —C(O)NH-lower alkyl;
    —(CH$_2$)$_n$-aryl, optionally substituted by halogen, aryloxy optionally substituted by halogen, lower alkoxy, or lower alkyl substituted by halogen;
    —S-aryl;
    —CH(OH)-aryl;
    —C(CH$_3$)$_2$-aryl;
    —NR-aryl; and
    2-oxo-2H-pyridin-1-yl;
    —(CH$_2$)$_n$-heterocyclyl, optionally substituted by =O;
    —(CH$_2$)$_n$-heteroaryl; and
    —(CH$_2$)$_n$—O-heteroaryl; and
  heteroaryl, optionally substituted by one or more substituents, selected from the group consisting of:
    halogen;
    lower alkyl;
    lower alkoxy;
    —(CH$_2$)$_n$-hydroxy;
    lower alkyl substituted by halogen;
    lower alkoxy substituted by halogen;
    —S(O)$_2$-lower alkyl;
    —(CH$_2$)$_n$—S(O)$_2$—NH-lower alkyl;
    —(CH$_2$)$_n$—O-lower alkyl;
    nitro;
    amino;
    —NHC(O)-lower alkyl;
    —C(O)NH-lower alkyl;
    —(CH$_2$)$_n$-aryl, optionally substituted by halogen, aryloxy optionally substituted by halogen, lower alkoxy, or lower alkyl substituted by halogen;
    —S-aryl;
    —CH(OH)-aryl;
    —C(CH$_3$)$_2$-aryl;
    —NR-aryl; and
    2-oxo-2H-pyridin-1-yl;
    —(CH$_2$)$_n$-heterocyclyl, optionally substituted by =O;
    —(CH$_2$)$_n$-heteroaryl; and
    —(CH$_2$)$_n$—O-heteroaryl;
$R^3$ is selected from the group consisting of: hydrogen and lower alkyl;
$R^4$ is selected from the group consisting of: hydrogen and lower alkyl; and
n is 0, 1, 2, 3 or 4
or a pharmaceutically active salt thereof;
with the proviso that the compound is not:
4-phenylaminomethyl-imidazol-dihydrochloride; or
benzyl-(3H-imidazol-4-ylmethyl)-phenyl-amine.

Preferred compounds of the present invention are those of formula I wherein $R^1$ is lower alkyl.

Especially preferred from this group are those wherein $R^2$ is optionally substituted aryl, for example the following compounds:

ethyl-(3H-imidazol-4-ylmethyl)-phenyl-amine;
methyl-(3H-imidazol-4-ylmethyl)-phenyl-amine;
(3-fluoro-phenyl)-(3H-imidazol-4-ylmethyl)-methyl-amine;
ethyl-(3H-imidazol-4-ylmethyl)-m-tolyl-amine;
(3H-imidazol-4-ylmethyl)-isopropyl-phenyl-amine;
(3-chloro-phenyl)-(3H-imidazol-4-ylmethyl)-methyl-amine;
(4-chloro-phenyl)-(3H-imidazol-4-ylmethyl)-methyl-amine;
(3-chloro-phenyl)-(3H-imidazol-4-ylmethyl)-isopropyl-amine;
(3,5-dichloro-phenyl)-(3H-imidazol-4-ylmethyl)-isopropyl-amine;
(3H-imidazol-4-ylmethyl)-isopropyl-(3-methoxy-phenyl)-amine;
(3H-imidazol-4-ylmethyl)-isopropyl-m-tolyl-amine;
(3H-imidazol-4-ylmethyl)-isopropyl-(3-trifluoromethyl-phenyl)-amine;
(4-chloro-phenyl)-(3H-imidazol-4-ylmethyl)-isopropyl-amine;
(4-chloro-3-trifluoromethyl-phenyl)-(3H-imidazol-4-ylmethyl)-isopropyl-amine;
(3,4-dichloro-phenyl)-(3H-imidazol-4-ylmethyl)-isopropyl-amine;
(3-chloro-4-trifluoromethoxy-phenyl)-(3H-imidazol-4-ylmethyl)-isopropyl-amine;
(4-chloro-phenyl)-ethyl-(3H-imidazol-4-ylmethyl)-amine;
(3,4-difluoro-phenyl)-ethyl-(3H-imidazol-4-ylmethyl)-amine;
(4-fluoro-phenyl)-(3H-imidazol-4-ylmethyl)-isopropyl-amine;
(3H-imidazol-4-ylmethyl)-isopropyl-(4-trifluoromethoxy-phenyl)-amine;
(3H-imidazol-4-ylmethyl)-isopropyl-naphthalen-2-yl-amine;
(3H-imidazol-4-ylmethyl)-indan-5-yl-isopropyl-amine;
(3-chloro-5-fluoro-phenyl)-(3H-imidazol-4-ylmethyl)-isopropyl-amine;
(3,4-difluoro-phenyl)-(3H-imidazol-4-ylmethyl)-isopropyl-amine;
(5-chloro-2-fluoro-phenyl)-(3H-imidazol-4-ylmethyl)-isopropyl-amine;
(3-chloro-2-fluoro-phenyl)-ethyl-(3H-imidazol-4-ylmethyl)-amine;
ethyl-(3H-imidazol-4-ylmethyl)-naphthalen-2-yl-amine;
(3,5-difluoro-phenyl)-(3H-imidazol-4-ylmethyl)-isopropyl-amine;
(2,4-difluoro-3-methoxy-phenyl)-(3H-imidazol-4-ylmethyl)-isopropyl-amine;
(4-fluoro-3-methyl-phenyl)-(3H-imidazol-4-ylmethyl)-isopropyl-amine;
(3H-imidazol-4-ylmethyl)-(3-isopropoxy-phenyl)-isopropyl-amine;
(3-benzyloxy-phenyl)-(3H-imidazol-4-ylmethyl)-isopropyl-amine;
(3H-imidazol-4-ylmethyl)-isopropyl-(3-trifluoromethoxy-phenyl)-amine;
(3H-imidazol-4-ylmethyl)-isopropyl-(3-phenoxy-phenyl)-amine;
((3-difluoromethoxy-phenyl)-(3H-imidazol-4-ylmethyl)-isopropyl-amine;
(3H-imidazol-4-ylmethyl)-isopropyl-[3-(1,1,2,2-tetrafluoro-ethoxy)-phenyl]-amine;
(3-chloro-4-methyl-phenyl)-(1H-imidazol-4-ylmethyl)-isopropyl-amine;
(3,4-dimethyl-phenyl)-ethyl-(1H-imidazol-4-ylmethyl)-amine;
(4-benzyloxy-3-chloro-phenyl)-(1H-imidazol-4-ylmethyl)-isopropyl-amine;
[3-chloro-4-(4-chloro-phenoxy)-phenyl]-ethyl-(1H-imidazol-4-ylmethyl)-amine;
(3-benzyl-phenyl)-(3H-imidazol-4-ylmethyl)-isopropyl-amine;
biphenyl-3-yl-(3H-imidazol-4-ylmethyl)-isopropyl-amine;
[3-(4-chloro-phenoxy)-phenyl]-(3H-imidazol-4-ylmethyl)-isopropyl-amine;
N-(1H-imidazol-4-ylmethyl)-N'-phenyl-benzene-1,4-diamine;
{4-[2-(4-chloro-phenyl)-ethyl]-phenyl}-ethyl-(1H-imidazol-4-ylmethyl)-amine;
(3-bromo-4-fluoro-phenyl)-(3H-imidazol-4-ylmethyl)-isopropyl-amine;
(3H-imidazol-4-ylmethyl)-methyl-(3-phenoxy-phenyl)-amine;
(3H-imidazol-4-ylmethyl)-(3-methoxy-phenyl)-methyl-amine;
ethyl-(3H-imidazol-4-ylmethyl)-(3-phenoxy-phenyl)-amine;
(3-difluoromethoxy-phenyl)-(3H-imidazol-4-ylmethyl)-methyl-amine;
(3-benzyloxy-phenyl)-(3H-imidazol-4-ylmethyl)-methyl-amine;
(3-benzyloxy-phenyl)-ethyl-(3H-imidazol-4-ylmethyl)-amine;
ethyl-(3H-imidazol-4-ylmethyl)-(3-methoxy-phenyl)-amine;
ethyl-(4-fluoro-3-methoxy-phenyl)-(3H-imidazol-4-ylmethyl)-amine;
(3-difluoromethoxy-phenyl)-ethyl-(3H-imidazol-4-ylmethyl)-amine;
(4-chloro-3-methoxy-phenyl)-(3H-imidazol-4-ylmethyl)-isopropyl-amine;
[3-(3-chloro-phenoxy)-phenyl]-(3H-imidazol-4-ylmethyl)-isopropyl-amine;
(3H-imidazol-4-ylmethyl)-isopropyl-(3-phenoxymethyl-phenyl)-amine;
(4-fluoro-3-phenoxy-phenyl)-(3H-imidazol-4-ylmethyl)-isopropyl-amine;
(3-bromo-phenyl)-(3H-imidazol-4-ylmethyl)-isopropyl-amine;
(3,4-dichloro-phenyl)-ethyl-(1H-imidazol-4-ylmethyl)-amine;
(3-bromo-phenyl)-ethyl-(3H-imidazol-4-ylmethyl)-amine;
(3-bromo-phenyl)-(3H-imidazol-4-ylmethyl)-methyl-amine;
(3,4-difluoro-phenyl)-(1H-imidazol-4-ylmethyl)-methyl-amine;
(3,4-dichloro-phenyl)-(1H-imidazol-4-ylmethyl)-methyl-amine;
(3,5-dichloro-phenyl)-(1H-imidazol-4-ylmethyl)-methyl-amine;
(3,5-difluoro-phenyl)-(1H-imidazol-4-ylmethyl)-methyl-amine;
(4-bromo-phenyl)-(1H-imidazol-4-ylmethyl)-isopropyl-amine;
(3,4-dibromo-phenyl)-(1H-imidazol-4-ylmethyl)-isopropyl-amine;
(4-bromo-phenyl)-ethyl-(1H-imidazol-4-ylmethyl)-amine;

(3,5-dichloro-phenyl)-ethyl-(1H-imidazol-4-ylmethyl)-amine;
(3-chloro-phenyl)-ethyl-(1H-imidazol-4-ylmethyl)-amine;
(4-bromo-3-fluoro-phenyl)-ethyl-(1H-imidazol-4-ylmethyl)-amine;
(3,5-difluoro-phenyl)-ethyl-(1H-imidazol-4-ylmethyl)-amine;
(4-chloro-3-fluoro-phenyl)-ethyl-(1H-imidazol-4-ylmethyl)-amine;
(3-chloro-5-fluoro-phenyl)-ethyl-(1H-imidazol-4-ylmethyl)-amine;
(3-bromo-4-fluoro-phenyl)-ethyl-(1H-imidazol-4-ylmethyl)-amine;
(3-chloro-4-fluoro-phenyl)-ethyl-(1H-imidazol-4-ylmethyl)-amine;
(4-chloro-3-methoxy-phenyl)-ethyl-(1H-imidazol-4-ylmethyl)-amine;
(4-bromo-3-chloro-phenyl)-(1H-imidazol-4-ylmethyl)-isopropyl-amine; and
(3-chloro-4-trifluoromethoxy-phenyl)-ethyl-(1H-imidazol-4-ylmethyl)-amine.

Also preferred are compounds of formula I wherein $R^1$ is hydrogen. Especially preferred from this group are such compounds wherein $R^2$ is optionally substituted aryl, for example the following compounds:
(3-chloro-5-fluoro-phenyl)-(1H-imidazol-4-ylmethyl)-amine;
{3-[ethyl-(3H-imidazol-4-ylmethyl)-amino]-2,6-difluoro-phenyl}-methanol;
(3-bromo-4-fluoro-phenyl)-(3H-imidazol-4-ylmethyl)-amine;
[3-(3-chloro-phenoxy)-phenyl]-(3H-imidazol-4-ylmethyl)-amine;
(4-fluoro-3-phenoxy-phenyl)-(3H-imidazol-4-ylmethyl)-amine;
(3-bromo-phenyl)-(3H-imidazol-4-ylmethyl)-amine;
(3-bromo-5-trifluoromethyl-phenyl)-(3H-imidazol-4-ylmethyl)-amine;
(3H-imidazol-4-ylmethyl)-(3-isopropyl-phenyl)-amine;
(3,5-difluoro-phenyl)-(1H-imidazol-4-ylmethyl)-amine;
(3,4-dibromo-phenyl)-(1H-imidazol-4-ylmethyl)-amine;
(3-chloro-4-fluoro-phenyl)-(1H-imidazol-4-ylmethyl)-amine;
(4-bromo-3-chloro-phenyl)-(1H-imidazol-4-ylmethyl)-amine; and
(3-chloro-4-trifluoromethoxy-phenyl)-(1H-imidazol-4-ylmethyl)-amine.

Also preferred are compounds of formula I wherein $R^1$ is lower alkyl and $R^2$ is optionally substituted heteroaryl, for example the following compounds:
(4,6-dichloro-pyrimidin-2-yl)-ethyl-(1H-imidazol-4-ylmethyl)-amine;
(6-bromo-pyridin-2-yl)-(3H-imidazol-4-ylmethyl)-isopropyl-amine; and
ethyl-(1H-imidazol-4-ylmethyl)-(6-trifluoromethyl-pyridin-2-yl)-amine.

A further embodiment of the invention are compounds of formula I wherein $R^1$ is optionally substituted $CH_2$-aryl. Especially preferred from this group are such compounds wherein $R^2$ is optionally substituted aryl, for example the following compounds:
(2-chloro-benzyl)-(3-chloro-phenyl)-(1H-imidazol-4-ylmethyl)-amine;
(3-chloro-benzyl)-(3-chloro-phenyl)-(1H-imidazol-4-ylmethyl)-amine;
(4-chloro-benzyl)-(3-chloro-phenyl)-(1H-imidazol-4-ylmethyl)-amine; and
benzyl-(3-chloro-phenyl)-(1H-imidazol-4-ylmethyl)-amine.

Also preferred are compounds of formula I wherein $R^1$ is CRH-cycloalkyl and $R^2$ is optionally substituted aryl, for example:
(3-chloro-phenyl)-cyclopropylmethyl-(3H-imidazol-4-ylmethyl)-amine; and
(3-chloro-phenyl)-(1-cyclopropylethyl)-(3H-imidazol-4-ylmethyl)-amine.

The present compounds of formula I and their pharmaceutically-acceptable salts can be prepared by methods known in the art, for example, by processes described below.

One such process comprises reacting an amine of formula II

with a compound of formula III

to produce a compound of formula I

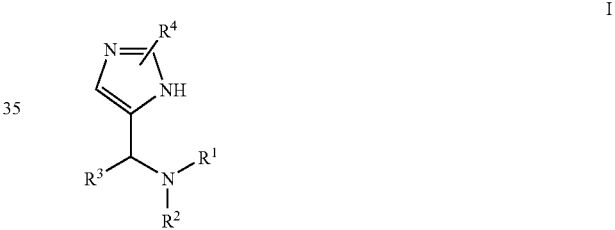

wherein $R^1$, $R^2$, $R^3$, and $R^4$ are as defined above.

Another such process comprises reacting a compound of formula I-1

with a compound of formula $R^{1'}$—CHO
to produce a compound of formula I-2

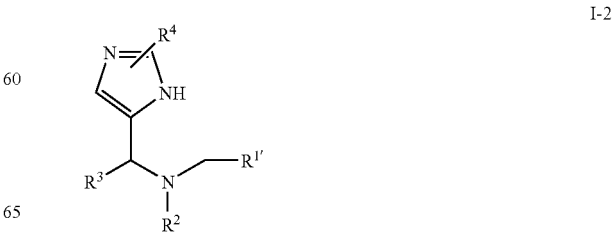

wherein $R^{1'}$ is selected from the group consisting of:

lower alkyl;

—$(CH_2)_{n-1}$-aryl optionally substituted by halogen, lower alkoxy, or lower alkyl substituted by halogen;

—$(CH_2)_{n-1}$-heteroaryl, optionally substituted by halogen, lower alkoxy, or lower alkyl substituted by halogen;

—$(CR_2)_{n-1}$—cycloalkyl, optionally substituted by hydroxyl;

—$(CR_2)_{n-1}$—OH,

—$(CH_2)_{n-1}$-heterocyclyl;

—$(CH_2)_{n-1}$—NH—S(O)$_2$CH; and

—$(CR_2)_{n-1}$O-lower alkyl.

The other variables are as described above.

Yet another such process comprises reacting a compound of formula I-1

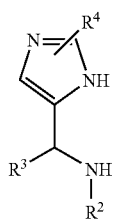

I-1 with a compound of formula V

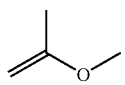

V to produce a compound of formula I-3

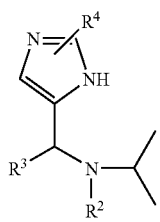

I-3 wherein the substituents are as defined above.

Yet another such process comprises removing a protecting group (denoted as "PG" below) from a compound of formula VI or a compound of formula X

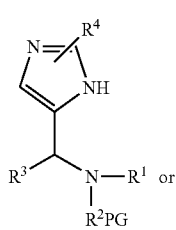

VI

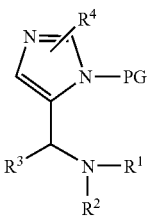

X to produce a compound of formula I

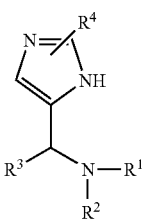

I wherein the substituents are as defined above, wherein the preferred protecting group is 2-trimethylsilanyl-ethoxymethyl.

If desired, the compound obtained by one of the processes described above may be converted into a pharmaceutically-acceptable salt.

The following are general schemes which exemplify the use of the above processes in the production of compounds of formula I. The starting materials are either commercially available, (e.g. from one or more of the following chemical suppliers such as Aldrich, Fluka, Acros, Maybridge, Avocado, TCI, or additional suppliers as indicated in databases such as Chemical Abstracts [American Chemical Society, Columbus, Ohio] or Available Chemicals Directory [Elsevier MDL, San Ramon, Calif.])", are otherwise known in the chemical literature, or may be prepared in accordance with methods described in the specific examples.

Method 1

Scheme 1

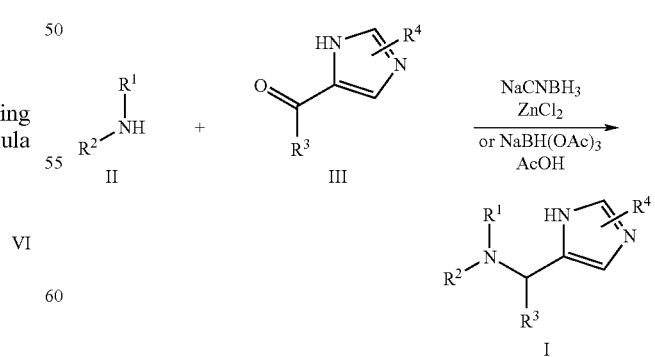

Compounds of formula I may be prepared by reductive amination using an amine of formula II and a corresponding imidazole-4-carbaldehyde/ketone of formula III.

Method 2

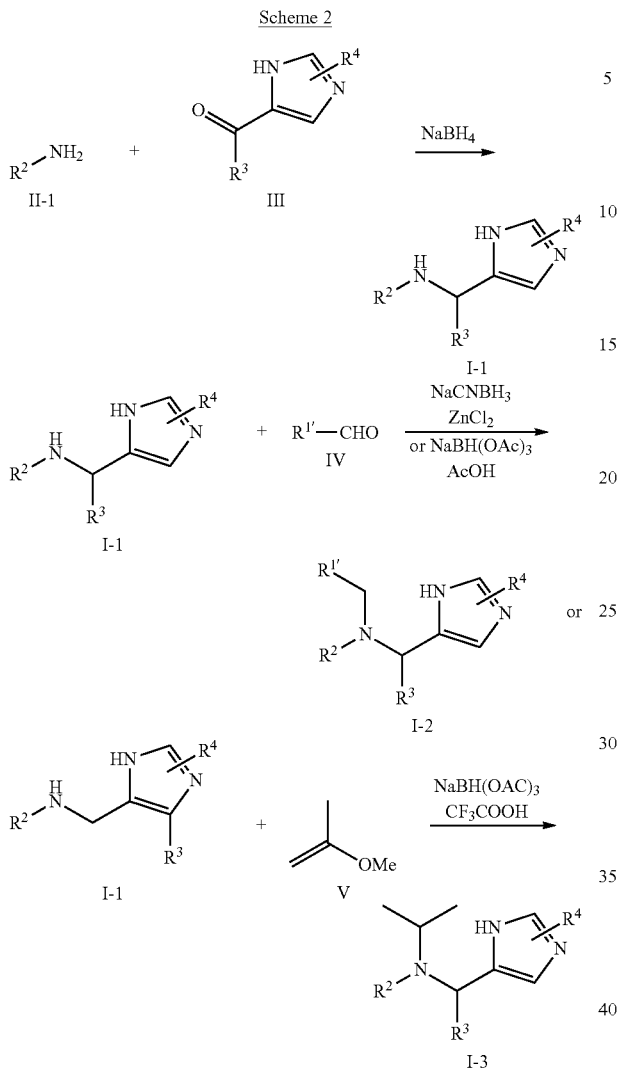

Compounds of formula I-1 may be prepared by reductive amination followed by N-derivatisation to obtain compounds of formulas I-2 or 1-3.

$R^{1'}$ is selected from the group consisting of:
lower alkyl;
—$(CH_2)_{n-1}$-aryl optionally substituted by halogen, lower alkoxy, or lower alkyl substituted halogen;
—$(CH_2)_{n-1}$-heteroaryl optionally substituted by halogen, lower alkoxy, or lower alkyl substituted halogen;
—$(CR_2)_{n-1}$-cycloalkyl, optionally substituted by hydroxy;
—$(CR_2)_{n-1}$—OH;
—$(CR_2)_{n-1}$-heterocyclyl;
—$(CH_2)_{n-1}$—NH—S(O)$_2$CH$_3$; and
—$(CR_2)_{n-1}$O-lower alkyl.

The other variables are as described above.

Method 3

Scheme 3

Compounds of formula I may be prepared from protected compounds of formula VI by removal of the protecting group ("PG"). The protecting groups are known groups described in the literature. The preferred protecting group is 2-trimethyl-silanyl-ethoxymethyl.

Method 4

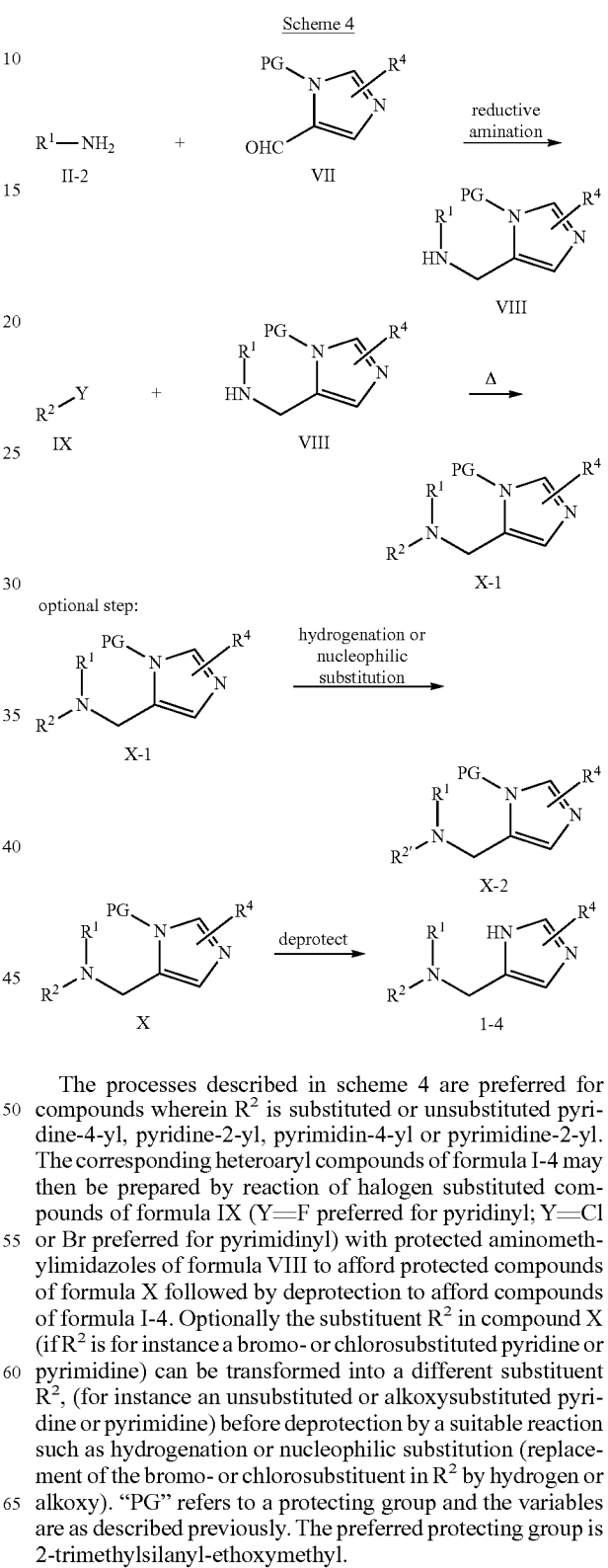

The processes described in scheme 4 are preferred for compounds wherein $R^2$ is substituted or unsubstituted pyridine-4-yl, pyridine-2-yl, pyrimidin-4-yl or pyrimidine-2-yl. The corresponding heteroaryl compounds of formula I-4 may then be prepared by reaction of halogen substituted compounds of formula IX (Y=F preferred for pyridinyl; Y=Cl or Br preferred for pyrimidinyl) with protected aminomethylimidazoles of formula VIII to afford protected compounds of formula X followed by deprotection to afford compounds of formula I-4. Optionally the substituent $R^2$ in compound X (if $R^2$ is for instance a bromo- or chlorosubstituted pyridine or pyrimidine) can be transformed into a different substituent $R^2$, (for instance an unsubstituted or alkoxysubstituted pyridine or pyrimidine) before deprotection by a suitable reaction such as hydrogenation or nucleophilic substitution (replacement of the bromo- or chlorosubstituent in $R^2$ by hydrogen or alkoxy). "PG" refers to a protecting group and the variables are as described previously. The preferred protecting group is 2-trimethylsilanyl-ethoxymethyl.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically-acceptable salts possess valuable pharmacological properties. Specifically, it has been found that the compounds of the present invention have a good affinity to the trace amine associated receptors (TAARs), especially TAAR1.

Pharmaceutical compositions containing a compound of formula I or a pharmaceutically-acceptable salt thereof and a therapeutically-inert carrier are also an object of the present invention, as is a process for their production, which comprises bringing one or more compounds of formula I and/or pharmaceutically-acceptable salts thereof and, if desired, one or more other therapeutically valuable substances into a galenical administration form together with one or more therapeutically-inert carriers.

The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, and parenterally, e.g. in the form of injection solutions.

The compounds of formula I can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention relates also to a method for treating a disease or disorder in a patient comprising administering a therapeutically-effective amount of a compound of the present invention to a patient in need of such treatment. A "therapeutically-effective amount" is the amount of the subject compound that will elicit the biological or medical response of a tissue, system, animal or human that is being sought by the researcher, veterinarian, medical doctor or other clinician. The above method may involve the administration of a composition which comprises a therapeutically-effective amount of the compound such as the compositions described above.

In preferred embodiments, the compound is used to treat disorders of the central nervous system, for example the treatment or prevention of schizophrenia, depression, cognitive impairment and Alzheimer's disease.

The therapeutically-effective amount can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation

Wet Granulation

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|  | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLES

The following examples illustrate the invention but are not intended to limit its scope.

Example 1

Ethyl-(3H-imidazol-4-ylmethyl)-phenyl-amine

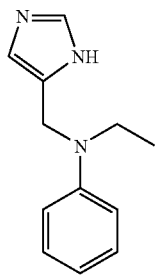

To a solution of N-ethylaniline (0.145 g, 1.2 mmol) in 1,2-dichloroethane (5 ml) were added molecular sieves (2 g, size 0.4 nM) and 4-formylimidazole (0.3 g, 3.12 mmol). After stirring the mixture for 5 min at room temperature sodium triacetoxyborohydride (1.02 g, 4.8 mmol) and acetic acid (5 drops) were added. The reaction mixture was stirred at room temperature overnight. For workup ethyl acetate (50 ml) and 1 M sodium bicarbonate solution (30 ml) were added and the mixture was shaken. The organic layer was separated, dried over magnesium sulfate and evaporated. The residue was purified using flash chromatography (column: Isolute® Flash-NH$_2$ (Separtis); eluent: ethyl acetate/methanol=95:5) to yield a white solid (122 mg, 51%); MS (ISP): 202.0 ((M+H)$^+$.).

Example 2

Methyl-(3H-imidazol-4-ylmethyl)-phenyl-amine

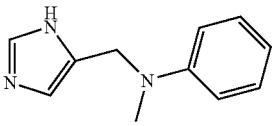

The title compound, MS (ISP): 188.1 ((M+H)$^+$.) was obtained in comparable yield analogous to the procedure described for Example 1 using N-methylaniline instead of N-ethylaniline.

Example 3

(2-Chloro-pyridin-4-yl)-ethyl-(3H-imidazol-4-ylmethyl)-amine

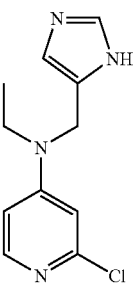 [SMILES: CCN(Cc1cnc[nH]1)c1ccnc(Cl)c1]

a) 5-Ethylaminomethyl-imidazole-1-sulfonic acid dimethylamide

To a saturated solution of ethylamine in methanol (40 ml) was added 4-formyl-imidazole-1-sulfonic acid dimethylamide (2.5 g, 12.3 mmol) and the mixture was stirred overnight. Sodium borohydride (0.70 g, 18.5 mmol) was added and the mixture was stirred at room temperature for 3 h. Water was added and the solution was extracted three times with ethyl acetate. The combined organic layers were dried over magnesium sulfate and evaporated. The residue was purified by flash chromatography (SiO2: dichloromethane/methanol=9:1) to yield a light yellow oil (0.785 g, 27%); MS (ISP): 233.1 ((M+H)$^+$.).

b) (2-Chloro-pyridin-4-yl)-ethyl-(3H-imidazol-4-ylmethyl)-amine

A mixture of 5-ethylaminomethyl-imidazole-1-sulfonic acid dimethylamide (0.2 g, 0.86 mmol) and 2-chloro-4-fluoropyridine (0.12 g; 0.91 mmol) was heated in a sealed vessel in a microwave oven for 30 min at 140° C. Then after cooling a solution of hydrochloric acid in ethanol (5 N, 1 ml) was added and the mixture was stirred at 90° C. overnight. For workup aqueous ammonia solution was added to basic pH and the mixture was extracted three times with ethyl acetate. The combined organic layers were dried over magnesium sulfate and evaporated. The residue was purified by flash chromatography (SiO$_2$; ethyl acetate/methanol 8:2) to yield a white solid, (0.13 g, 64%); MS (ISP): 239.0 ((M+H)$^+$.).

Example 4

(3-Fluoro-phenyl)-(3H-imidazol-4-ylmethyl)-methyl-amine

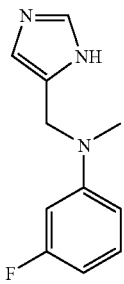

The title compound, MS (EI): 205.1 (M⁺.) was obtained in comparable yield analogous to the procedure described for Example 1 using N-methyl-3-fluoroaniline instead of N-ethylaniline.

Example 5

(3H-Imidazol-4-ylmethyl)-methyl-o-tolyl-amine

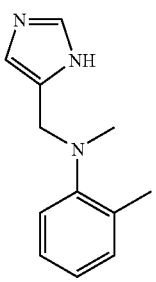

The title compound, MS (ISP): 202.1 ((M+H)⁺.) was obtained in comparable yield analogous to the procedure described for Example 1 using N-methyl-o-tolylamine instead of N-ethylaniline.

Example 6

Ethyl-(3H-imidazol-4-ylmethyl)-m-tolyl-amine

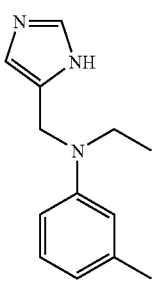 [SMILES: CCN(Cc1cnc[nH]1)c1cccc(C)c1]

The title compound, MS (ISP): 216.2 ((M+H)⁺.) was obtained in comparable yield analogous to the procedure described for Example 1 using N-ethyl-m-tolylamine instead of N-ethylaniline.

Example 7

(3H-Imidazol-4-ylmethyl)-isopropyl-phenyl-amine

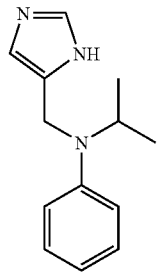 [SMILES: CC(C)N(Cc1cnc[nH]1)c1ccccc1]

The title compound, MS (ISP): 216.2 ((M+H)⁺.) was obtained in comparable yield analogous to the procedure described for Example 1 using isoporopyl-phenyl-amine instead of N-ethylaniline.

Example 8

(2-Chloro-phenyl)-(3H-imidazol-4-ylmethyl)-methyl-amine

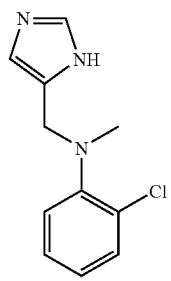

The title compound, MS (ISP): 221.9 ((M+H)⁺.) was obtained in comparable yield analogous to the procedure described for Example 1 using 2-(chlorophenyl)-methyl-amine instead of N-ethylaniline.

Example 9

(3-Chloro-phenyl)-(3H-imidazol-4-ylmethyl)-methyl-amine

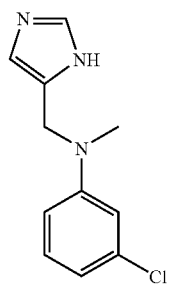

The title compound, MS (ISP): 221.9 ((M+H)⁺.) was obtained in comparable yield analogous to the procedure described for Example 1 using 3-(chlorophenyl)-methyl-amine instead of N-ethylaniline.

Example 10

(4-Chloro-phenyl)-(3H-imidazol-4-ylmethyl)-methyl-amine

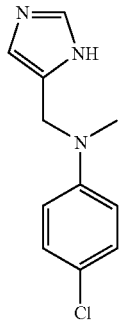

The title compound, MS (ISP): 221.9 ((M+H)$^+$.) was obtained in comparable yield analogous to the procedure described for Example 1 using 4-(chlorophenyl)-methyl-amine instead of N-ethylaniline.

Example 11

Cyclohexyl-(3H-imidazol-4-ylmethyl)-phenyl-amine

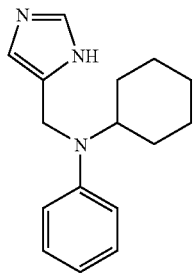 [SMILES: c1ccc(N(Cc2cnc[nH]2)C2CCCCC2)cc1]

The title compound, MS (ISP): 256.0 ((M+H)$^+$.) was obtained in comparable yield analogous to the procedure described for Example 1 using cyclohexyl-phenyl-amine instead of N-ethylaniline.

Example 12

2-[(3H-Imidazol-4-ylmethyl)-phenyl-amino]-ethanol

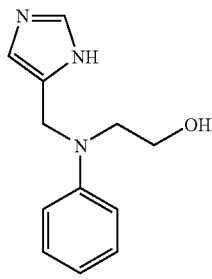 [SMILES: OCCN(Cc1cnc[nH]1)c1ccccc1]

The title compound, MS (ISP): 218.0 ((M+H)$^+$.) was obtained in comparable yield analogous to the procedure described for Example 1 using 2-phenylamino-ethanol instead of N-ethylaniline.

Example 13

(3H-Imidazol-4-ylmethyl)-(2-methoxy-phenyl)-methyl-amine

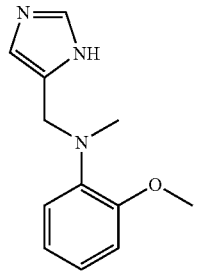 [SMILES: COc1ccccc1N(C)Cc1cnc[nH]1]

The title compound, MS (ISP): 218.0 ((M+H)$^+$.) was obtained in comparable yield analogous to the procedure described for Example 1 using (2-methoxy-phenyl)-methyl-amine instead of N-ethylaniline.

Example 14

(3-Chloro-phenyl)-methyl-(2-methyl-3H-imidazol-4-ylmethyl)-amine

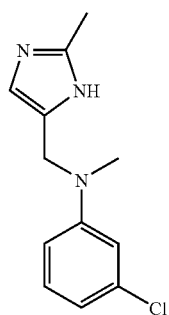 [SMILES: Cc1ncc(CN(C)c2cccc(Cl)c2)[nH]1]

The title compound, MS (ISP): 236.1 ((M+H)$^+$.) was obtained in comparable yield analogous to the procedure described for Example 1 using 3-(chlorophenyl)-methyl-amine instead of N-ethylaniline and 4-formyl-2-methylimidazole instead of 4-formylimidazole.

Example 15

(3-Chloro-phenyl)-methyl-(5-methyl-3H-imidazol-4-ylmethyl)-amine

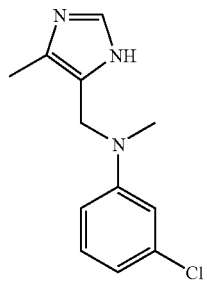 [SMILES: Cc1nc[nH]c1CN(C)c1cccc(Cl)c1]

The title compound, MS (ISP): 235.8 ((M+H)$^+$.) was obtained in comparable yield analogous to the procedure described for Example 1 using 3-(chlorophenyl)-methyl-amine instead of N-ethylaniline and 4-formyl-5-methylimidazole instead of 4-formylimidazole.

Example 16

(3-Chloro-phenyl)-(1H-imidazol-4-ylmethyl)-(2-trifluoromethyl-benzyl)-amine

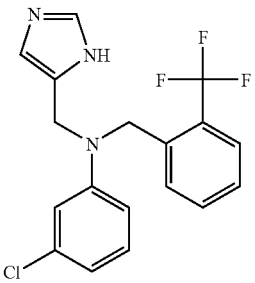 [SMILES: FC(F)(F)c1ccccc1CN(Cc1cnc[nH]1)c1cccc(Cl)c1]

The title compound, MS (ISP): 366.0 ((M+H)$^+$.) was obtained in comparable yield analogous to the procedure described for Example 1 using (3-chloro-phenyl)-(3-trifluoromethyl-benzyl)-amine instead of N-ethylaniline.

Example 17

(3-Chloro-phenyl)-(H-imidazol-4-ylmethyl)-(3-methoxy-benzyl)-amine

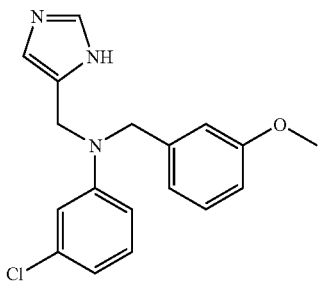 [SMILES: COc1cccc(CN(Cc2cnc[nH]2)c2cccc(Cl)c2)c1]

The title compound, MS (ISP): 327.9 ((M+H)$^+$.) was obtained in comparable yield analogous to the procedure described for Example 1 using (3-chloro-phenyl)-(3-methoxy-benzyl)-amine instead of N-ethylaniline.

Example 18

(2-Chloro-benzyl)-(3-chloro-phenyl)-(1H-imidazol-4-ylmethyl)-amine

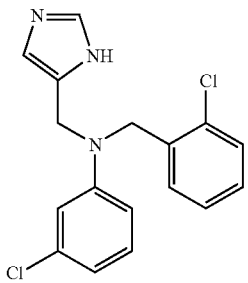 [SMILES: Clc1cccc(N(Cc2cnc[nH]2)Cc2ccccc2Cl)c1]

The title compound, MS (ISP): 332.0; 334.0 ((M+H)$^+$.) was obtained in comparable yield analogous to the procedure described for Example 1 using (2-chloro-benzyl)-(3-chloro-phenyl)-amine instead of N-ethylaniline.

Example 19

(3-Chloro-benzyl)-(3-chloro-phenyl)-(1H-imidazol-4-ylmethyl)-amine

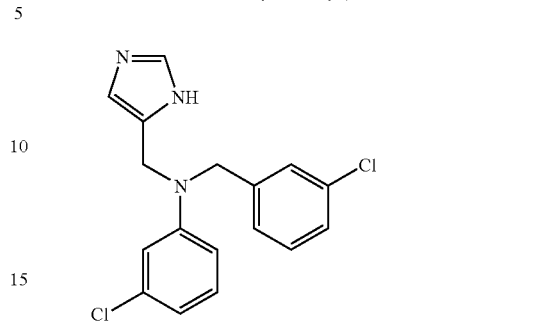

The title compound, MS (ISP): 331.9; 334.0 ((M+H)$^+$.) was obtained in comparable yield analogous to the procedure described for Example 1 using (3-chloro-benzyl)-(3-chloro-phenyl)-amine instead of N-ethylaniline.

Example 20

(4-Chloro-benzyl)-(3-chloro-phenyl)-(1H-imidazol-4-ylmethyl)-amine

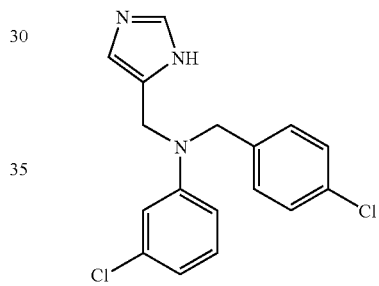

The title compound, MS (ISP): 332.0; 334.0 ((M+H)$^+$.) was obtained in comparable yield analogous to the procedure described for Example 1 using (4-chloro-benzyl)-(3-chloro-phenyl)-amine instead of N-ethylaniline.

Example 21

Benzyl-(3-chloro-phenyl)-(1H-imidazol-4-ylmethyl)-amine

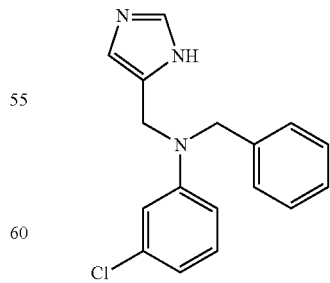

The title compound, MS (ISP): 298.1 ((M+H)$^+$.) was obtained in comparable yield analogous to the procedure described for Example 1 using benzyl-(3-chloro-phenyl)-amine instead of N-ethylaniline.

Example 22

(3-Bromo-benzyl)-(1H-imidazol-4-ylmethyl)-phenyl-amine

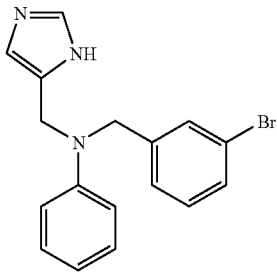 [SMILES: Brc1cccc(CN(Cc2cnc[nH]2)c2ccccc2)c1]

The title compound, MS (ISP): 341.9; 343.9 ((M+H)$^+$.) was obtained in comparable yield analogous to the procedure described for Example 1 using (3-bromo-benzyl)-phenyl-amine instead of N-ethylaniline.

Example 23

(3-Chloro-phenyl)-(3H-imidazol-4-ylmethyl)-isopropyl-amine

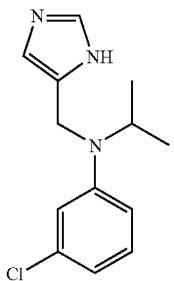

The title compound, MS (ISP): 250.1 ((M+H)$^+$.) was obtained in comparable yield analogous to the procedure described for Example 1 using (3-chloro-phenyl)-isopropyl-amine instead of N-ethylaniline.

Example 24

(3,5-Dichloro-phenyl)-(3H-imidazol-4-ylmethyl)-isopropyl-amine

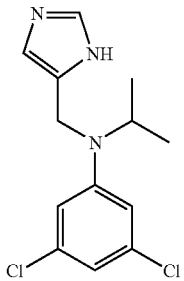 [SMILES: CC(C)N(Cc1cnc[nH]1)c1cc(Cl)cc(Cl)c1]

The title compound, MS (ISP): 283.9; 285.9 ((M+H)$^+$.) was obtained in comparable yield analogous to the procedure described for Example 1 using (3,5-dichloro-phenyl)-isopropyl-amine instead of N-ethylaniline.

Example 25

(3H-Imidazol-4-ylmethyl)-isopropyl-(3-methoxy-phenyl)-amine

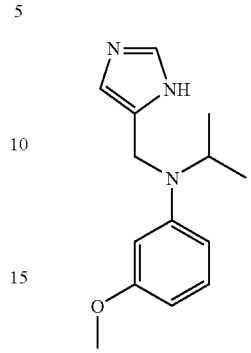

The title compound, MS (ISP): 246.1 ((M+H)$^+$.) was obtained in comparable yield analogous to the procedure described for Example 1 using isopropyl-(3-methoxy-phenyl)-amine instead of N-ethylaniline.

Example 26

(3H-Imidazol-4-ylmethyl)-isopropyl-m-tolyl-amine

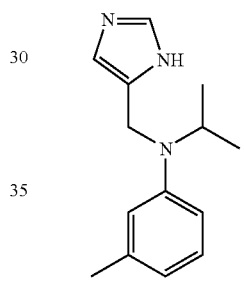

The title compound, MS (ISP): 230.0 ((M+H)$^+$.) was obtained in comparable yield analogous to the procedure described for Example 1 using N-isopropyl-m-tolylamine instead of N-ethylaniline.

Example 27

(3H-Imidazol-4-ylmethyl)-isopropyl-(3-trifluoromethyl-phenyl)-amine

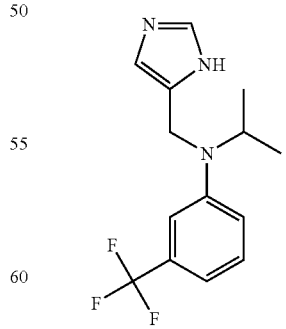

The title compound, MS (ISP): 284.0 ((M+H)$^+$.) was obtained in comparable yield analogous to the procedure described for Example 1 using N-isopropyl-3-(trifluoromethyl)aniline instead of N-ethylaniline.

Example 28

(4-Chloro-phenyl)-(3H-imidazol-4-ylmethyl)-isopropyl-amine

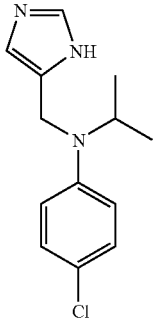 [SMILES: CC(C)N(Cc1cnc[nH]1)c1ccc(Cl)cc1]

The title compound, MS (ISP): 250.1 ((M+H)$^+$.) was obtained in comparable yield analogous to the procedure described for Example 1 using (4-chloro-phenyl)-isopropyl-amine instead of N-ethylaniline.

Example 29

(3H-Imidazol-4-ylmethyl)-isopropyl-(4-methoxyphenyl)-amine

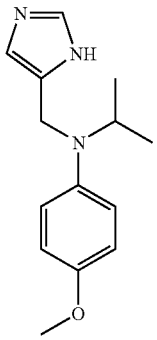 [SMILES: COc1ccc(N(Cc2cnc[nH]2)C(C)C)cc1]

The title compound, MS (ISP): 246.1 ((M+H)$^+$.) was obtained in comparable yield analogous to the procedure described for Example 1 using isopropyl-(4-methoxy-phenyl)-amine instead of N-ethylaniline.

Example 30

(1H-Imidazol-4-ylmethyl)-diphenyl-amine

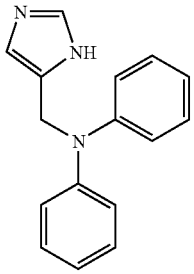 [SMILES: c1ccc(N(Cc2cnc[nH]2)c2ccccc2)cc1]

The title compound, MS (ISP): 250.1 ((M+H)$^+$.) was obtained in comparable yield analogous to the procedure described for Example 1 using diphenyl-amine instead of N-ethylaniline.

Example 31

(4-Chloro-3-trifluoromethyl-phenyl)-(3H-imidazol-4-ylmethyl)-isopropyl-amine

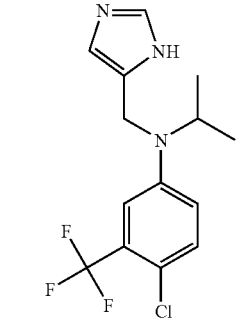 [SMILES: CC(C)N(Cc1cnc[nH]1)c1ccc(Cl)c(C(F)(F)F)c1]

a) (4-Chloro-3-trifluoromethyl-phenyl)-isopropyl-amine

5-Amino-2-chlorobenzotrifluoride (0.587 g, 3.0 mmol) was dissolved in methanol (30 ml). Then acetone (1.58 ml, 30 mmol) and zinc chloride (1.635 g, 12 mmol) were added and the reaction mixture was cooled with an ice bath. After adding sodium cyanoborohydride (0.566 g, 9.0 mmol) the mixture was allowed to stir at 40° C. overnight. After cooling, the reaction mixture was poured onto ammonium chloride/ice and extracted with ethyl acetate (2 times 50 ml). The organic layer was dried over magnesium sulfate and evaporated. The residue was purified using flash chromatography (SiO$_2$; eluent: heptane/ethyl acetate=95:5) to yield a light yellow oil (0.530 g, 74%) that was directly used for the next step; MS (EI): 222.1 ((M-CH$_3$)$^+$); 237.1 (M$^+$.).

b) (4-Chloro-3-trifluoromethyl-phenyl)-(3H-imidazol-4-ylmethyl)-isopropyl-amine (4-Chloro-3-trifluoromethyl-phenyl)-(3H-imidazol-4-ylmethyl)-isopropyl-amine, MS (ISP): 318.1 ((M+H)$^+$.) was obtained in comparable yield analogous to the procedure described for Example 1 using (4-chloro-3-trifluoromethyl-phenyl)-isopropyl-amine instead of N-ethylaniline.

Example 32

(3,4-Dichloro-phenyl)-(3H-imidazol-4-ylmethyl)-isopropyl-amine

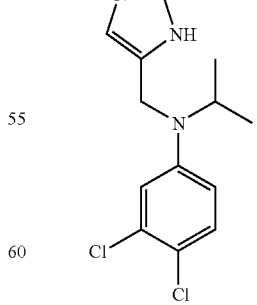

The title compound, MS (ISP): 284.0 ((M+H)$^+$.) was obtained in comparable yield analogous to the procedure described for Example 1 using (3,4-dichloro-phenyl)-isopropyl-amine instead of N-ethylaniline.

Example 33

(3-Chloro-4-trifluoromethoxy-phenyl)-(3H-imidazol-4-ylmethyl)-isopropyl-amine

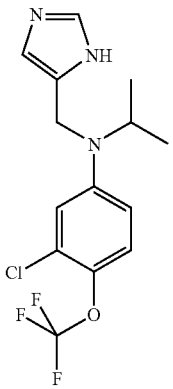 [SMILES: CC(C)N(Cc1cnc[nH]1)c1ccc(OC(F)(F)F)c(Cl)c1]

a) (3-Chloro-4-trifluoromethoxy-phenyl)-isopropyl-amine (3-Chloro-4-trifluoromethoxy-phenyl)-isopropyl-amine was obtained in comparable yield analogous to the procedure described for Example 31 step a) using 3-chloro-4-trifluoromethoxy-phenylamine instead of 5-amino-2-chlorobenzotrifluoride and was used directly in the next step.

b) (3-Chloro-4-trifluoromethoxy-phenyl)-(3H-imidazol-4-ylmethyl)-isopropyl-amine The title compound, MS (ISP): 334.2 ((M+H)$^+$.) was obtained in comparable yield analogous to the procedure described for Example 1 using (3-chloro-4-trifluoromethoxy-phenyl)-isopropyl-amine instead of N-ethylaniline.

Example 34

(3H-Imidazol-4-ylmethyl)-isopropyl-(3-methoxy-5-trifluoromethyl-phenyl)-amine

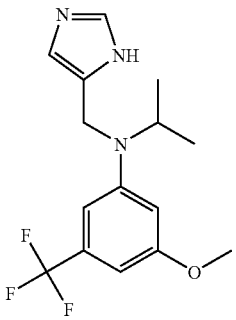 [SMILES: COc1cc(N(Cc2cnc[nH]2)C(C)C)cc(C(F)(F)F)c1]

a) Isopropyl-(3-methoxy-5-trifluoromethyl-phenyl)-amine

Isopropyl-(3-methoxy-5-trifluoromethyl-phenyl)-amine was obtained in comparable yield analogous to the procedure described for Example 31 step a) using 3-methoxy-5-(trifluoromethyl)-aniline instead of 5-amino-2-chlorobenzotrifluoride and was used directly in the next step.

b) (3H-Imidazol-4-ylmethyl)-isopropyl-(3-methoxy-5-trifluoromethyl-phenyl)-amine The title compound, MS (ISP): 314.1 ((M+H)$^+$.) was obtained in comparable yield analogous to the procedure described for Example 1 using isopropyl-(3-methoxy-5-trifluoromethyl-phenyl)-amine instead of N-ethylaniline.

Example 35

(3-Chloro-phenyl)-isopropyl-(2-methyl-3H-imidazol-4-ylmethyl)-amine

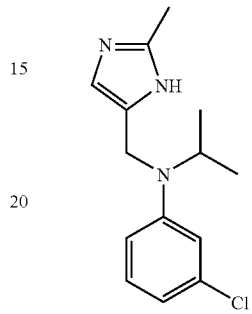

The title compound, MS (ISP): 264.1 ((M+H)$^+$.) was obtained in comparable yield analogous to the procedure described for Example 1 using 3-(chlorophenyl)-isopropyl-amine instead of N-ethylaniline and 4-formyl-2-methylimidazole instead of 4-formylimidazole.

Example 36

Cyclopropyl-(3H-imidazol-4-ylmethyl)-phenyl-amine

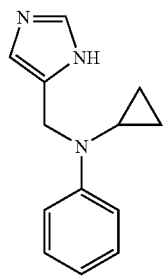 [SMILES: c1ccc(N(Cc2cnc[nH]2)C2CC2)cc1]

The title compound, MS (ISP): 214.1 ((M+H)$^+$.) was obtained in comparable yield analogous to the procedure described for Example 1 using N-cyclopropyl-aniline instead of N-ethylaniline.

Example 37

(3-Chloro-4-methoxy-phenyl)-(3H-imidazol-4-ylmethyl)-isopropyl-amine

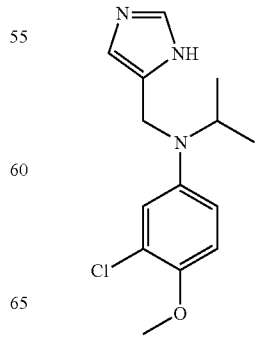

N-Isopropyl-3-chloro-4-methoxy-aniline (0.20 g, 1.0 mmol) was dissolved in methanol (10 ml). Then 4-formylimidazole (0.288 g, 3.0 mmol) and zinc chloride (0.545 g, 4.0 mmol) were added and the reaction mixture was cooled with an ice bath. After adding sodium cyanoborohydride (0.189 g, 3.0 mmol) the mixture was allowed to stir at 40° C. overnight. After cooling, the reaction mixture was poured onto ammoniumchloride/ice and extracted with ethyl acetate (3 times 20 ml). The organic layer was dried over magnesium sulfate and evaporated. The residue was purified using flash chromatography (column: Isolute® Flash-NH$_2$ (Separtis); eluent: ethyl acetate/methanol=95:5) to yield a white solid (136 mg, 49%); MS (ISP): 280.0 ((M+H)$^+$.).

Example 38

(R)-2-[(3H-Imidazol-4-ylmethyl)-phenyl-amino]-propan-1-ol

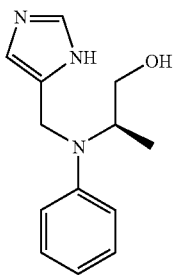 [SMILES: C[C@H](CO)N(Cc1cnc[nH]1)c1ccccc1]

The title compound, MS (ISP): 231.9 ((M+H)$^+$.) was obtained in comparable yield analogous to the procedure described for Example 37 using (R)-2-phenylamino-propan-1-ol instead of N-isopropyl-3-chloro-4-methoxy-aniline.

Example 39

(S)-2-[(3H-Imidazol-4-ylmethyl)-phenyl-amino]-propan-1-ol

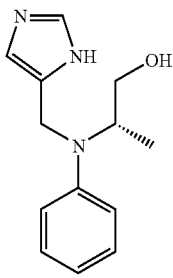 [SMILES: C[C@@H](CO)N(Cc1cnc[nH]1)c1ccccc1]

The title compound, MS (ISP): 231.9 ((M+H)$^+$.) was obtained in comparable yield analogous to the procedure described for Example 37 using (S)-2-phenylamino-propan-1-ol instead of N-isopropyl-3-chloro-4-methoxy-aniline.

Example 40

(3H-Imidazol-4-ylmethyl)-(1-methoxymethyl-propyl)-phenyl-amine

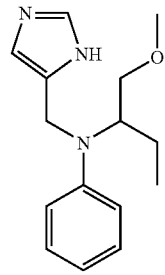 [SMILES: CCC(COC)N(Cc1cnc[nH]1)c1ccccc1]

The title compound, MS (ISP): 260.0 ((M+H)$^+$.) was obtained in comparable yield analogous to the procedure described for Example 37 using (1-methoxymethyl-propyl)-phenyl-amine instead of N-isopropyl-3-chloro-4-methoxy-aniline.

Example 41

(2,2-Difluoro-ethyl)-(3H-imidazol-4-ylmethyl)-phenyl-amine

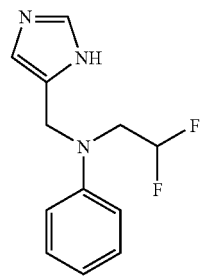 [SMILES: FC(F)CN(Cc1cnc[nH]1)c1ccccc1]

The title compound, MS (ISP): 237.9 ((M+H)$^+$.) was obtained in comparable yield analogous to the procedure described for Example 37 using (2,2-difluoroethyl)-phenyl-amine instead of N-isopropyl-3-chloro-4-methoxy-aniline.

Example 42

Biphenyl-4-yl-(3H-imidazol-4-ylmethyl)-isopropyl-amine

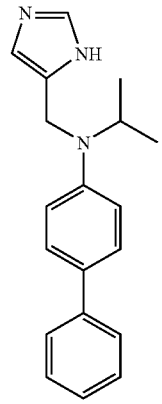 [SMILES: CC(C)N(Cc1cnc[nH]1)c1ccc(-c2ccccc2)cc1]

The title compound, MS (ISP): 292.1 ((M+H)$^+$.) was obtained in comparable yield analogous to the procedure described for Example 37 using biphenyl-4-yl-isopropylamine instead of N-isopropyl-3-chloro-4-methoxy-aniline.

Example 43

(1H-Imidazol-4-ylmethyl)-(2-methoxy-ethyl)-phenyl-amine

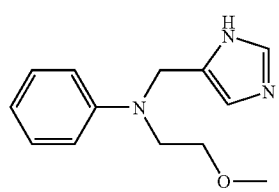 [SMILES: COCCN(Cc1cnc[nH]1)c1ccccc1]

The title compound, MS (ISP): 232.2 ((M+H)$^+$.) was obtained in comparable yield analogous to the procedure described for Example 37 using (2-methoxyethyl)-phenyl-amine instead of N-isopropyl-3-chloro-4-methoxy-aniline.

Example 44

[1,3]Dioxolan-2-ylmethyl-(1H-imidazol-4-ylmethyl)-phenyl-amine

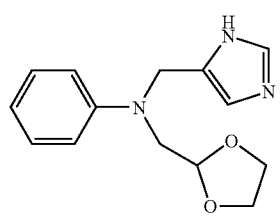 [SMILES: c1ccc(N(Cc2cnc[nH]2)CC2OCCO2)cc1]

a) [1,3]Dioxolan-2-ylmethyl-phenyl-amine

A suspension of phenylboronic acid (0.5 g, 4.1 mmol), copper(II)-acetate-1-hydrate (0.041 g, 0.21 mmol) and molecular sieves (1.5 g, size 0.4 nm, powdered) in dichloromethane (12 ml) was stirred for 5 min. Then 2-(aminomethyl)-1,3-dioxolane (0.211 g, 2.05 mmol) was added and oxygen was bubbled through the mixture for 5 min. The vessel was closed and shaken overnight at room temperature. For workup ethyl acetate (50 ml) and 1 M sodium bicarbonate solution (30 ml) were added and the mixture was shaken. The organic layer was separated, dried over magnesium sulfate and evaporated. The residue was purified using flash chromatography (SiO$_2$; eluent: heptane/ethyl acetate=90:10) to yield a light yellow oil (105 mg, 14%); MS (EI): 179.1 (M$^+$.).

b) [1,3]Dioxolan-2-ylmethyl-(1H-imidazol-4-ylmethyl)-phenyl-amine

The title compound, MS (ISP): 260.1 ((M+H)$^+$.) was obtained in comparable yield analogous to the procedure described for Example 37 using [1,3]dioxolan-2-ylmethyl-phenyl-amine instead of N-isopropyl-3-chloro-4-methoxy-aniline.

Example 45

(1H-Imidazol-4-ylmethyl)-phenyl-(tetrahydro-furan-2-ylmethyl)-amine

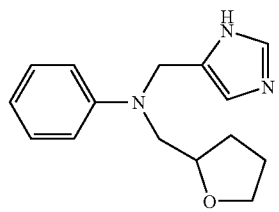 [SMILES: c1ccc(N(Cc2cnc[nH]2)CC2CCCO2)cc1]

The title compound, MS (ISP): 258.1 ((M+H)$^+$.) was obtained in comparable yield analogous to the procedure described for Example 37 using phenyl-(tetrahydro-furan-2-ylmethyl)-amine instead of N-isopropyl-3-chloro-4-methoxy-aniline.

Example 46

(3-Chloro-phenyl)-(1H-imidazol-4-ylmethyl)-(2-methoxy-ethyl)-amine

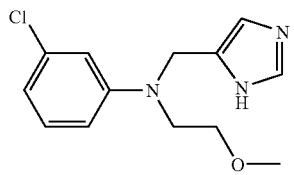 [SMILES: COCCN(Cc1cnc[nH]1)c1cccc(Cl)c1]

The title compound, MS (ISP): 266.2 ((M+H)$^+$.) was obtained in comparable yield analogous to the procedure described for Example 37 using (3-chloro-phenyl)-(2-methoxy-ethyl)-amine instead of N-isopropyl-3-chloro-4-methoxy-aniline.

Example 47

N-{2-[(3H-Imidazol-4-ylmethyl)-phenyl-amino]-ethyl}-methanesulfonamide

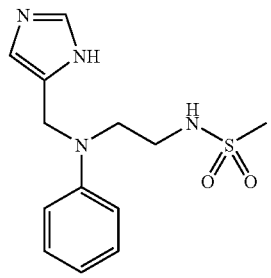 [SMILES: CS(=O)(=O)NCCN(Cc1cnc[nH]1)c1ccccc1]

The title compound, MS (ISP): 295.1 ((M+H)$^+$.) was obtained in comparable yield analogous to the procedure described for Example 1 using N-(2-anilinoethyl)-methansulfonamide instead of N-ethylaniline.

Example 48

(2-Butyl-3H-imidazol-4-ylmethyl)-(3-chloro-phenyl)-isopropyl-amine

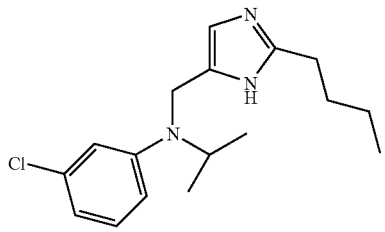 [SMILES: CCCCc1ncc(CN(c2cccc(Cl)c2)C(C)C)[nH]1]

The title compound, MS (ISP): 306.4 ((M+H)+.) was obtained in comparable yield analogous to the procedure described for Example 37 using N-isopropyl-3-chloro-aniline instead of N-isopropyl-3-chloro-4-methoxy-aniline and 2-butyl-4-formyl-imidazole instead of 4-formylimidazole.

Example 49

(3H-Imidazol-4-ylmethyl)-phenyl-(tetrahydro-pyran-4-yl)-amine

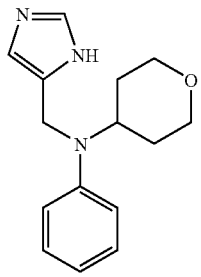 [SMILES: c1ccc(N(Cc2cnc[nH]2)C2CCOCC2)cc1]

The title compound, MS (ISP): 257.9 ((M+H)+.) was obtained in comparable yield analogous to the procedure described for Example 1 using phenyl-(tetrahydro-pyran-4-yl)-amine instead of N-ethylaniline.

Example 50 tert-Butyl-(3-chloro-phenyl)-(3H-imidazol-4-ylmethyl)-amine

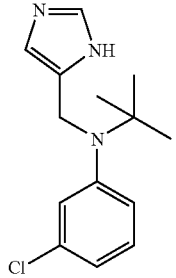 [SMILES: CC(C)(C)N(Cc1cnc[nH]1)c1cccc(Cl)c1]

The title compound, MS (ISP): 263.9; 266.0 ((M+H)+.) was obtained in comparable yield analogous to the procedure described for Example 1 using tert-butyl-(3-chloro-phenyl)-amine instead of N-ethylaniline.

Example 51

(3-Chloro-phenyl)-cyclopropylmethyl-(3H-imidazol-4-ylmethyl)-amine

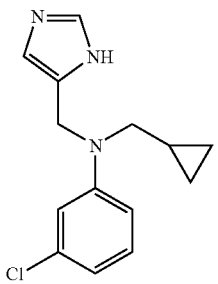 [SMILES: Clc1cccc(N(Cc2cnc[nH]2)CC2CC2)c1]

a) (3-chloro-phenyl)-cyclopropylmethyl-amine

To a solution of 3-chloroaniline (1.27 g, 10 mmol) in 1,2-dichloroethane (20 ml) were added molecular sieves (4 g, size 0.4 nM) and cyclopropanecarboxyaldehyde (0.7 g, 10 mmol). After stirring the mixture for 5 min at room temperature sodium triacetoxyborohydride (3.18 g, 15 mmol) and acetic acid (0.6 g, 10 mmol) were added. The reaction mixture was stirred at room temperature overnight. For workup dichloromethane (100 ml) and 1 M sodium bicarbonate solution (40 ml) were added and the mixture was shaken. The organic layer was separated, dried over magnesium sulfate and evaporated. The residue was purified using flash chromatography (heptane/ethyl acetate=9:1) to yield a colourless liquid (1.09 g, 60%); MS (EI): 181.1 (M+.).

b) (3-Chloro-phenyl)-cyclopropylmethyl-(3H-imidazol-4-ylmethyl)-amine

The title compound, MS (ISP): 261.9; 263.9 ((M+H)+.) was obtained in comparable yield analogous to the procedure described for Example 1 using (3-chloro-phenyl)-cyclopropylmethyl-amine instead of N-ethylaniline.

Example 52

(3-Chloro-phenyl)-(1-cyclopropylethyl)-(3H-imidazol-4-ylmethyl)-amine

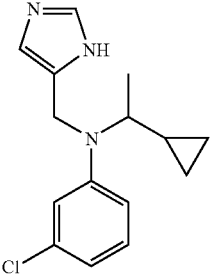 [SMILES: CC(C1CC1)N(Cc1cnc[nH]1)c1cccc(Cl)c1]

a) (3-chloro-phenyl)-(1-cyclopropylethyl)-amine

To a solution of 3-chloroaniline (1.27 g, 10 mmol) in 1,2-dichloroethane (20 ml) were added molecular sieves (4 g, size 0.4 nM) and cyclopropyl methyl ketone (0.84 g, 10 mmol).

After stirring the mixture for 5 min at room temperature sodium triacetoxyborohydride (3.18 g, 15 mmol) and acetic acid (0.6 g, 10 mmol) were added. The reaction mixture was stirred at room temperature overnight. For workup dichloromethane (100 ml) and 1 M sodium bicarbonate solution (40 ml) were added and the mixture was shaken. The organic layer was separated, dried over magnesium sulfate and evaporated. The residue was purified using flash chromatography (heptane/ethyl acetate=9:1) to yield a colourless liquid (0.083 g, 4.5%); MS (ISP): 196.3 (M+H)$^+$.).

b) (3-Chloro-phenyl)-(1-cyclopropylethyl)-(3H-imidazol-4-ylmethyl)-amine

The title compound, MS (ISP): 276.0; 277.9 ((M+H)$^+$.) was obtained in comparable yield analogous to the procedure described for Example 1 using (3-chloro-phenyl)-(1-cyclopropylethyl)-amine instead of N-ethylaniline.

Example 53

(3-Chloro-4-fluoro-phenyl)-(3H-imidazol-4-ylmethyl)-isopropyl-amine

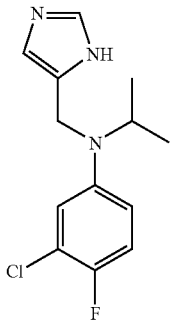 [SMILES: CC(C)N(Cc1cnc[nH]1)c1ccc(F)c(Cl)c1]

The title compound, MS (ISP): 268.1 ((M+H)$^+$.) was obtained analogous to the procedure described for Example 1 using (3-chloro-4-fluoro-phenyl)-isopropyl-amine instead of N-ethylaniline.

Example 54 trans-4-[(3-Chloro-phenyl)-(3H-imidazol-4-ylmethyl)-amino]-cyclohexanol

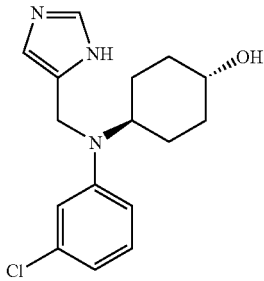 [SMILES: O[C@H]1CC[C@H](N(Cc2cnc[nH]2)c2cccc(Cl)c2)CC1]

a) trans-[4-(tert-Butyl-dimethyl-silanyloxy)-cyclohexyl]-(3-chloro-phenyl)-amine To a solution of 3-chloroaniline (1.27 g, 10 mmol) in 1,2-dichloroethane (20 ml) were added molecular sieves (4 g, size 0.4 nM) and 4-(tert-butyldimethylsilyloxy)-cyclohexanone (4.57 g, 20 mmol). After stirring the mixture for 30 min at room temperature sodium triacetoxyborohydride (8.48 g, 40 mmol) and acetic acid (1.2 g, 20 mmol) were added. The reaction mixture was stirred at room temperature overnight. For workup dichloromethane (100 ml) and 1 M sodium bicarbonate solution (40 ml) were added and the mixture was shaken. The organic layer was separated, dried over magnesium sulfate and evaporated. The residue was purified using flash chromatography (heptane/ethyl acetate=1:1) to yield a colourless liquid (0.80 mg, 23.5%); MS (EI): 339.2; 341.3 (M$^+$.).

b) trans-4-[(3-Chloro-phenyl)-(3H-imidazol-4-ylmethyl)-amino]-cyclohexanol

To a solution of [4-(tert-butyl-dimethyl-silanyloxy)-cyclohexyl]-(3-chloro-phenyl)-amine (0.68 g, 20 mmol) in 1,2-dichloroethane (10 ml) were added molecular sieves (2 g, size 0.4 nM) and 4-formyl-imidazole (0.50 g, 5.2 mmol). After stirring the mixture for 30 min at room temperature sodium triacetoxyborohydride (1.70 g, 8 mmol) and acetic acid (0.24 g, 4 mmol) were added. The reaction mixture was stirred at room temperature overnight. For workup dichloromethane (50 ml) and 1 M sodium bicarbonate solution (30 ml) were added and the mixture was shaken. The organic layer was separated, dried over magnesium sulfate and evaporated. The residue was purified using flash chromatography (heptane/ethyl acetate=1:1) to yield a 0.3 g of a white solid. This compound was dissolved in tetrahydrofuran (5 ml), tetrabutylammonium fluoride solution (1M in tetrahydrofuran, 2 ml) was added at 0° C., and the mixture was stirred at room temperature overnight. The solvent was evaporated and the residue was mixed with water and ethyl acetate. The organic layer was separated, dried over magnesium sulfate and evaporated. The residue was purified using flash chromatography (ethyl acetate/methanol=9:1) to yield a white foam (0.14 mg, 65%); MS (ISP): 306.2 (M+H)$^+$).

Example 55

(4-Chloro-phenyl)-(3H-imidazol-4-ylmethyl)-oxetan-3-yl-amine

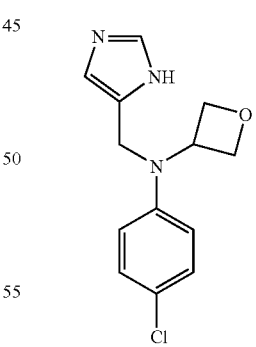

a) (4-Chloro-phenyl)-oxetan-3-yl-amine

4-Chloroaniline (0.26 g, 2.0 mmol) was dissolved in methanol (25 ml). Then 3-oxetanone (0.22 g, 3 mmol) and zinc chloride (1.09 g, 8.0 mmol) were added and the reaction mixture was cooled with an ice bath. After adding sodium cyanoborohydride (0.377 g, 6.0 mmol) the mixture was allowed to stir at 40° C. for 5 hours. After cooling, the reaction mixture was poured onto ammonium chloride/ice and extracted with ethyl acetate (3 times 20 ml). The organic layer was dried over magnesium sulfate and evaporated. The residue was purified using flash chromatography (heptane/ethyl acetate=95:5) to yield a light yellow liquid (108 mg, 29%); $^1$H-NMR (CDCl$_3$): 4.14 b, 1H(NH); 4.55 m, 3H(CHO, CHN); 5.00 t, 2H(CHO), 6.43 d, 2H (aryl-H) and 7.15 d, 2H (aryl-H).

b) (4-Chloro-phenyl)-(3H-imidazol-4-ylmethyl)-oxetan-3-yl-amine

The title compound, MS (ISP): 264.1 ((M+H)$^+$.) was obtained in comparable yield analogous to the procedure described for Example 1 using (4-chloro-phenyl)-oxetan-3-yl-amine instead of N-ethylaniline.

Example 56

(3-Chloro-phenyl)-1-[(3H-imidazol-4-yl)-ethyl]-methyl-amine

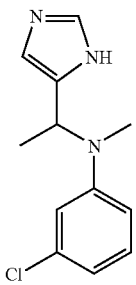 [SMILES: CC(c1cnc[nH]1)N(C)c1cccc(Cl)c1]

The title compound, MS (ISP): 236.1 ((M+H)$^+$.) was obtained in comparable yield analogous to the procedure described for Example 1 using (3-chlorophenyl)-methyl-amine instead of N-ethylaniline and 4-acetylimidazole instead of 4-formylimidazole.

Example 57

(4-Chloro-phenyl)-ethyl-(3H-imidazol-4-ylmethyl)-amine

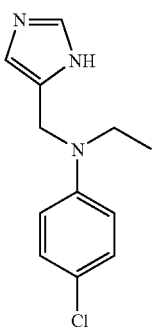 [SMILES: CCN(Cc1cnc[nH]1)c1ccc(Cl)cc1]

The title compound, MS (ISP): 236.1; 238.1 ((M+H)$^+$.) was obtained in comparable yield analogous to the procedure described for Example 1 using (4-chlorophenyl)-ethyl-amine instead of N-ethylaniline.

Example 58

(3,4-Difluoro-phenyl)-ethyl-(3H-imidazol-4-ylm-ethyl)-amine

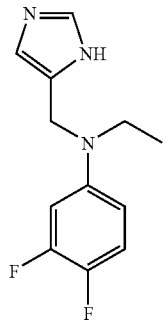

The title compound, MS (ISP): 238.1 ((M+H)$^+$.) was obtained in comparable yield analogous to the procedure described for Example 1 using (3,4-difluorophenyl)-ethyl-amine instead of N-ethylaniline.

Example 59

Benzo[1,3]dioxol-5-yl-ethyl-(3H-imidazol-4-ylm-ethyl)-amine

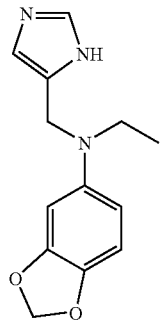 [SMILES: CCN(Cc1cnc[nH]1)c1ccc2c(c1)OCO2]

The title compound, MS (ISP): 246.1 ((M+H)$^+$.) was obtained in comparable yield analogous to the procedure described for Example 1 using (benzo[1,3]dioxol-5-yl)-ethyl-amine instead of N-ethylaniline.

Example 60

(2-Fluoro-phenyl)-(3H-imidazol-4-ylmethyl)-isopropyl-amine

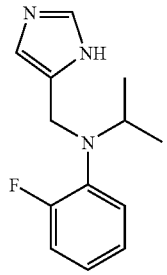

The title compound, MS (ISP): 234.1 ((M+H)$^+$.) was obtained in comparable yield analogous to the procedure described for Example 1 using (2-fluorophenyl)-isopropyl-amine instead of N-ethylaniline.

Example 61

(3-Fluoro-phenyl)-(3H-imidazol-4-ylmethyl)-isopropyl-amine

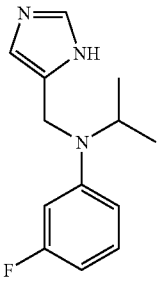 [SMILES: CC(C)N(Cc1cnc[nH]1)c1cccc(F)c1]

The title compound, MS (ISP): 234.1 ((M+H)$^+$.) was obtained in comparable yield analogous to the procedure described for Example 1 using (3-fluorophenyl)-isopropylamine instead of N-ethylaniline.

Example 62

(4-Fluoro-phenyl)-(3H-imidazol-4-ylmethyl)-isopropyl-amine

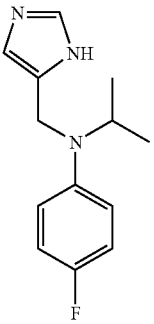 [SMILES: CC(C)N(Cc1cnc[nH]1)c1ccc(F)cc1]

The title compound, MS (ISP): 234.0 ((M+H)$^+$.) was obtained in comparable yield analogous to the procedure described for Example 1 using (4-fluorophenyl)-isopropylamine instead of N-ethylaniline.

Example 63

(3H-Imidazol-4-ylmethyl)-(2-methoxy-phenyl)-amine

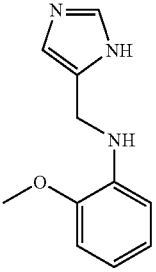

To a solution of 2-methoxyaniline (0.62 g, 5 mmol) in methanol (5 ml) was added 4-formylimidazole (0.48 g, 5 mmol). After stirring the mixture overnight at 60° C. the solution was cooled and sodium borohydride (0.28 g, 7.5 mmol) were added. The reaction mixture was stirred at room temperature for 4 hours. Then water was added and the mixture was extracted with ethyl acetate. The organic layer was separated, washed with water, dried over magnesium sulfate and evaporated. The residue was purified by recrystallisation from heptane/ethyl acetate to yield off-white crystals (0.85 mg, 84%); MS (ISP): 204.3 ((M+H)$^+$.).

Example 64

(3H-Imidazol-4-ylmethyl)-(3-methanesulfonyl-phenyl)-amine

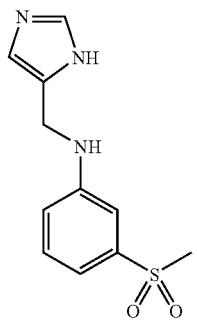 [SMILES: CS(=O)(=O)c1cccc(NCc2cnc[nH]2)c1]

The title compound, MS (ISP): 252.1 ((M+H)$^+$.) was obtained in comparable yield analogous to the procedure described for Example 63 using 3-methylsulfonyl-aniline instead of 2-methoxyaniline.

Example 65

(3H-Imidazol-4-ylmethyl)-quinolin-6-yl-amine

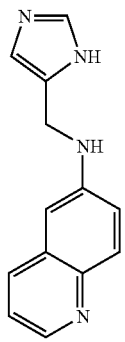

The title compound, MS (ISP): 225.1 ((M+H)$^+$.) was obtained in comparable yield analogous to the procedure described for Example 63 using 6-aminoquinoline instead of 2-methoxyaniline.

Example 66

(3H-Imidazol-4-ylmethyl)-(2-isopropyl-6-methyl-phenyl)-amine

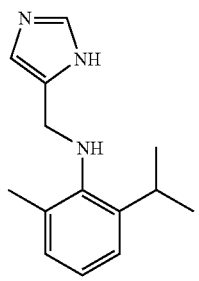 [SMILES: Cc1cccc(C(C)C)c1NCc1cnc[nH]1]

The title compound, MS (ISP): 230.4 ((M+H)⁺.) was obtained in comparable yield analogous to the procedure described for Example 63 using 2-isopropyl-6-methylaniline instead of 2-methoxyaniline.

Example 67

(3H-Imidazol-4-ylmethyl)-isopropyl-(4-trifluoromethoxy-phenyl)-amine

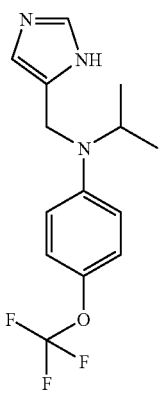 [SMILES: CC(C)N(Cc1cnc[nH]1)c1ccc(OC(F)(F)F)cc1]

a) (3H-Imidazol-4-ylmethyl)-(4-trifluoromethoxy-phenyl)-amine

To a solution of 4-trifluoromethoxyaniline (0.89 g, 5 mmol) in methanol (5 ml) was added 4-formylimidazole (0.48 g, 5 mmol). After stirring the mixture overnight at 60° C. the solution was cooled and sodium borohydride (0.28 g, 7.5 mmol) were added. The reaction mixture was stirred at room temperature for 4 hours. Then water was added and the mixture was extracted with ethyl acetate. The organic layer was separated, washed with water, dried over magnesium sulfate and evaporated. The residue was purified by column filtration (heptane/ethyl acetate=1:1) to yield a light yellow liquid (1.0 g, 78%); MS (ISP): 258.1 ((M+H)⁺.).

b) (3H-Imidazol-4-ylmethyl)-isopropyl-(4-trifluoromethoxy-phenyl)-amine

To a solution of (3H-imidazol-4-ylmethyl)-(4-trifluoromethoxy-phenyl)-amine (0.39 g, 1.5 mmol) in 1,2-dichloroethane (5 ml) were added successively 2-methoxypropene (0.16 g, 2.25 mmol), trifluoroacetic acid (0.26 g, 2.25 mmol) and sodium triacetoxyborohydride (0.48 g, 2.25 mmol). After stirring the mixture overnight at 60° C. 1 M sodium hydroxide solution (5 ml) was added and the mixture was extracted with dichloromethane. The organic layer was washed with brine, dried over magnesium sulfate and evaporated. The residue was purified by column chromatography (heptane/ethyl acetate=1:1) to yield a white solid (0.24 g, 53%); MS (ISP): 300.1 ((M+H)⁺.).

Example 68

(3H-Imidazol-4-ylmethyl)-isopropyl-(3-methoxymethyl-phenyl)-amine

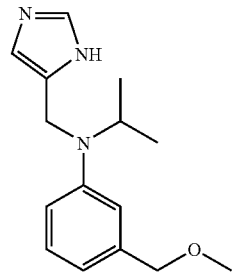 [SMILES: COCc1cccc(N(Cc2cnc[nH]2)C(C)C)c1]

The title compound, MS (ISP): 260.3 ((M+H)⁺.) was obtained in comparable yield analogous to the procedure described for Example 67 using 3-methoxymethyl-aniline instead of 4-trifluoromethoxyaniline in step a).

Example 69

(3H-Imidazol-4-ylmethyl)-isopropyl-(3-methanesulfonyl-phenyl)-amine

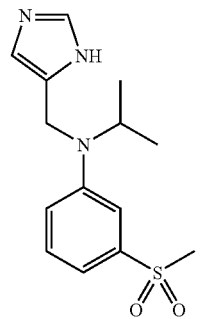 [SMILES: CC(C)N(Cc1cnc[nH]1)c1cccc(S(C)(=O)=O)c1]

The title compound, MS (ISP): 280.3 ((M-CH₃)⁺); 294.3 ((M+H)⁺.) was obtained in comparable yield analogous to the procedure described for Example 67 using 3-methanesulfonyl-aniline instead of 4-trifluoromethoxyaniline in step a).

Example 70

(3H-Imidazol-4-ylmethyl)-isopropyl-naphthalen-2-yl-amine

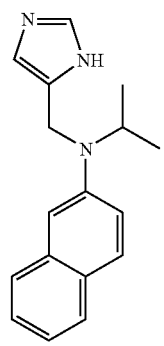 [SMILES: CC(C)N(Cc1cnc[nH]1)c1ccc2ccccc2c1]

The title compound, MS (ISP): 266.1 ((M+H)+.) was obtained in comparable yield analogous to the procedure described for Example 67 using 2-aminonaphthaline instead of 4-trifluoromethoxyaniline in step a).

Example 71

(3H-Imidazol-4-ylmethyl)-isopropyl-quinolin-6-yl-amine

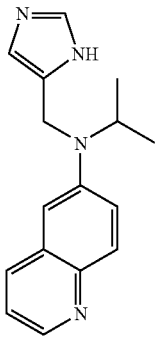 [SMILES: CC(C)N(Cc1cnc[nH]1)c1ccc2ncccc2c1]

The title compound, MS (ISP): 267.4 ((M+H)+.) was obtained in comparable yield analogous to the procedure described for Example 67 using 6-aminoquinoline instead of 4-trifluoromethoxyaniline in step a).

Example 72

(3H-Imidazol-4-ylmethyl)-isopropyl-(6-methoxy-pyridin-3-yl)-amine

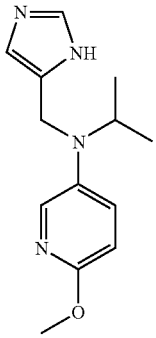

The title compound, MS (ISP): 247.3 ((M+H)+.) was obtained in comparable yield analogous to the procedure described for Example 67 using 5-amino-2-methoxypyridine instead of 4-trifluoromethoxyaniline in step a).

Example 73

(3H-Imidazol-4-ylmethyl)-indan-5-yl-isopropyl-amine

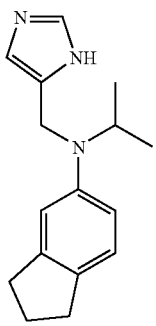 [SMILES: CC(C)N(Cc1cnc[nH]1)c1ccc2c(c1)CCC2]

The title compound, MS (ISP): 256.3 ((M+H)+.) was obtained in comparable yield analogous to the procedure described for Example 67 using indan-5-ylamine instead of 4-trifluoromethoxyaniline in step a).

Example 74

(3H-Imidazol-4-ylmethyl)-pyrazin-2-yl-amine

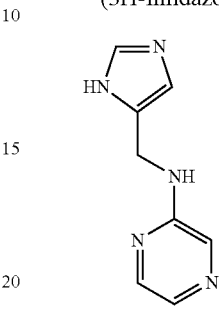

The title compound, MS (ISP): 176.0 ((M+H)+.) was obtained in comparable yield analogous to the procedure described for Example 63 using pyrazin-2-ylamine instead of 2-methoxyaniline.

Example 75

(2-Chloro-pyridin-3-yl)-(3H-imidazol-4-ylmethyl)-amine

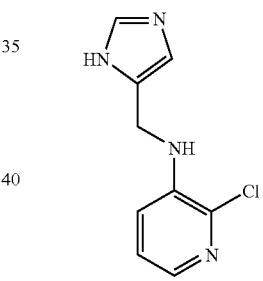

The title compound, MS (ISP): 208.8; 210.9 ((M+H)+.) was obtained in comparable yield analogous to the procedure described for Example 63 using 3-amino-2-chloro-pyridine instead of 2-methoxyaniline.

Example 76

(3-Chloro-5-fluoro-phenyl)-(3H-imidazol-4-ylmethyl)-isopropyl-amine

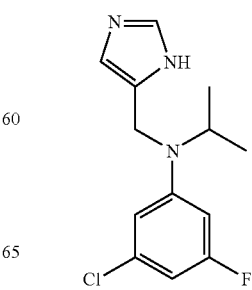

The title compound, MS (ISP): 268.3, 270.3 ((M+H)+.) was obtained in comparable yield analogous to the procedure described for Example 67 using 3-chloro-5-fluoroaniline instead of 4-trifluoromethoxyaniline in step a).

Example 77

(3,4-Difluoro-phenyl)-(3H-imidazol-4-ylmethyl)-isopropyl-amine

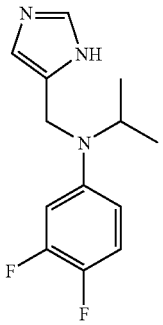

The title compound, MS (ISP): 252.3 ((M+H)+.) was obtained in comparable yield analogous to the procedure described for Example 67 using 3,4-difluoroaniline instead of 4-trifluoromethoxyaniline in step a).

Example 78

(5-Chloro-2-fluoro-phenyl)-(3H-imidazol-4-ylmethyl)-isopropyl-amine

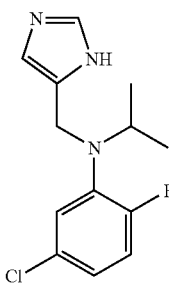

The title compound, MS (ISP): 268.1 ((M+H)+.) was obtained in comparable yield analogous to the procedure described for Example 67 using 5-chloro-2-fluoroaniline instead of 4-trifluoromethoxyaniline in step a).

Example 79

(4-Chloro-2-fluoro-phenyl)-(3H-imidazol-4-ylmethyl)-isopropyl-amine

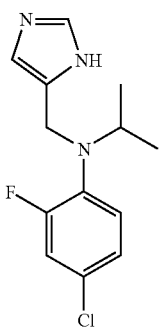 [SMILES: CC(C)N(Cc1cnc[nH]1)c1ccc(Cl)cc1F]

The title compound, MS (ISP): 268.4 ((M+H)+.) was obtained in comparable yield analogous to the procedure described for Example 67 using 4-chloro-2-fluoroaniline instead of 4-trifluoromethoxyaniline in step a).

Example 80

(3-Fluoro-4-methoxy-phenyl)-(3H-imidazol-4-ylmethyl)-isopropyl-amine

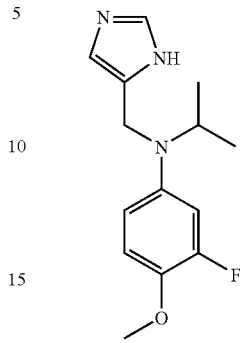

The title compound, MS (ISP): 264.3 ((M+H)+.) was obtained in comparable yield analogous to the procedure described for Example 67 using 3-fluoro-4-methoxyaniline instead of 4-trifluoromethoxyaniline in step a).

Example 81

(3-Chloro-2-fluoro-phenyl)-ethyl-(3H-imidazol-4-ylmethyl)-amine

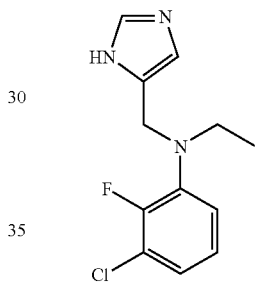

a) (3-Chloro-2-fluoro-phenyl)-(3H-imidazol-4-ylmethyl)-amine

To a solution of 3-chloro-2-fluoroaniline (0.44 g, 3 mmol) in methanol (5 ml) was added 4-formylimidazole (0.29 g, 3 mmol). After stirring the mixture overnight at 60° C. the solution was cooled and sodium borohydride (0.57 g, 15 mmol) was added. The reaction mixture was stirred at room temperature for 4 hours. Then water was added and the mixture was extracted with ethyl acetate. The organic layer was separated, washed with water, dried over magnesium sulfate and evaporated. The residue was purified by column filtration (heptane/ethyl acetate=1:1) to yield a light yellow liquid (0.55 mg, 81%); MS (ISP): 226.3 ((M+H)+.).

b) (3-Chloro-2-fluoro-phenyl)-ethyl-(3H-imidazol-4-ylmethyl)-amine (3-Chloro-2-fluoro-phenyl)-(3H-imidazol-4-ylmethyl)-amine (0.24 g, 1 mmol) was dissolved in methanol (15 ml). Then acetaldehyde (0.28 ml, 5 mmol), zinc chloride (0.55 g, 4 mmol) and sodium cyanoborohydride (0.19 g, 3 mmol) were added and the reaction mixture was allowed to stir at 40° C. overnight. After cooling, the reaction mixture was poured onto ammoniumchloride/ice and extracted with ethyl acetate (2 times 50 ml). The organic layer was dried over magnesium sulfate and evaporated. The residue was purified using flash chromatography (SiO$_2$; eluent: heptane/ethyl acetate=90:10) to yield a light yellow oil (0.16 g, 63%); MS (ISP): 254.1 ((M+H)+.).

Example 82

Ethyl-(3H-imidazol-4-ylmethyl)-naphthalen-2-yl-amine

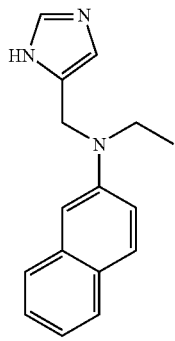 [SMILES: CCN(Cc1cnc[nH]1)c1ccc2ccccc2c1]

The title compound, MS (ISP): 252.1 ((M+H)$^+$.) was obtained in comparable yield analogous to the procedure described for Example 81 using 2-naphthylamine instead of 3-chloro-2-fluoroaniline in step a).

Example 83

(3H-Imidazol-4-ylmethyl)-isopropyl-(3-nitro-phenyl)-amine

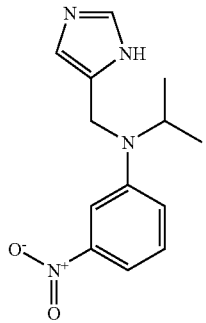 [SMILES: CC(C)N(Cc1cnc[nH]1)c1cccc([N+](=O)[O-])c1]

The title compound, MS (ISP): 261 ((M+H)$^+$.) was obtained in comparable yield analogous to the procedure described for Example 67 using 3-nitroaniline instead of 4-trifluoromethoxyaniline in step a).

Example 84

(2-Chloro-pyridin-3-yl)-ethyl-(3H-imidazol-4-ylmethyl)-amine

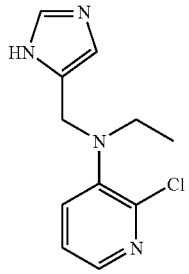 [SMILES: CCN(Cc1cnc[nH]1)c1cccnc1Cl]

The title compound, MS (ISP): 237.1 ((M+H)$^+$.) was obtained in comparable yield analogous to the procedure described for Example 81 using 3-amino-2-chloropyridine instead of 3-chloro-2-fluoroaniline in step a).

Example 85

Ethyl-(3H-imidazol-4-ylmethyl)-(2-methoxy-pyridin-3-yl)-amine

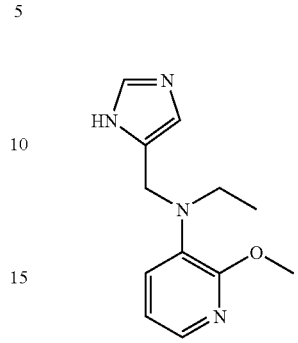

The title compound, MS (ISP): 233.3 ((M+H)$^+$.) was obtained in comparable yield analogous to the procedure described for Example 81 using 3-amino-2-methoxypyridine instead of 3-chloro-2-fluoroaniline in step a).

Example 86

(6-Chloro-pyridin-3-yl)-ethyl-(3H-imidazol-4-ylmethyl)-amine

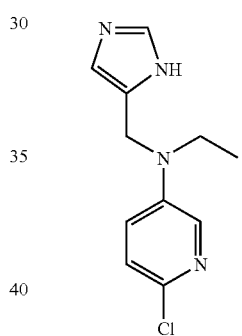

The title compound, MS (ISP): 236.8; 238.9 ((M+H)$^+$.) was obtained in comparable yield analogous to the procedure described for Example 81 using 5-amino-2-chloropyridine instead of 3-chloro-2-fluoroaniline in step a).

Example 87

(6-Chloro-pyridin-3-yl)-(3H-imidazol-4-ylmethyl)-isopropyl-amine

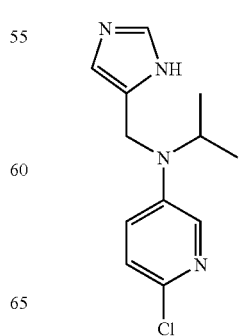

The title compound, MS (ISP): 250.9; 252.9 ((M+H)⁺.) was obtained analogous to the procedure described for Example 67 using 5-amino-2-chloropyridine instead of 4-trifluoromethoxyaniline in step a).

Example 88

(3H-Imidazol-4-ylmethyl)-isopropyl-pyridin-2-yl-amine

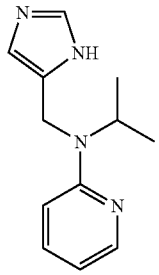 [SMILES: CC(C)N(Cc1cnc[nH]1)c1ccccn1]

The title compound, MS (ISP): 217.4 ((M+H)⁺.) was obtained analogous to the procedure described for Example 67 using 2-aminopyridine instead of 4-trifluoromethoxyaniline in step a).

Example 89

(3H-Imidazol-4-ylmethyl)-isopropyl-quinolin-8-yl-amine

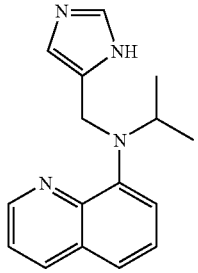 [SMILES: CC(C)N(Cc1cnc[nH]1)c1cccc2cccnc12]

The title compound, MS (ISP): 267.3 ((M+H)⁺.) was obtained analogous to the procedure described for Example 67 using 8-aminoquinoline instead of 4-trifluoromethoxyaniline in step a).

Example 90

N-(3H-Imidazol-4-ylmethyl)-N-isopropyl-benzene-1,3-diamine

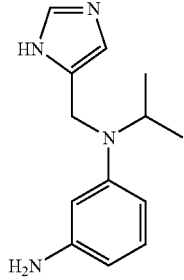 [SMILES: CC(C)N(Cc1cnc[nH]1)c1cccc(N)c1]

a) Isopropyl-(3-nitro-phenyl)-[3-(2-trimethylsilanyl-ethoxymethyl)-3H-imidazol-4-ylmethyl]-amine To sodium hydride (149 mg, 55% in mineral oil, 3.42 mmol) in tetrahydrofuran (240 ml) was added a solution of (3H-imidazol-4-ylmethyl)-isopropyl-(3-nitro-phenyl)-amine (685 mg, 2.63 mmol) in tetrahydrofuran (100 ml) and stirring was continued for 45 min at room temperature. The reaction mixture was cooled with an ice bath and 2-(trimethylsilyl)ethoxymethylchloride (439 mg, 2.63 mmol) was added. After stirring the suspension overnight the reaction was quenched with saturated sodium bicarbonate solution. Tetrahydrofuran was evaporated and the residue was extracted with ethyl acetate twice. The combined organic layers were washed with water, dried over magnesium sulphate and evaporated. The residue was purified using flash chromatography (SiO₂; eluent: heptane/ethyl acetate=80:20) to yield a light yellow oil, (0.20 g, 20%); MS (ISP): 391.3 ((M+H)⁺.).

b) N-(3H-Imidazol-4-ylmethyl)-N-isopropyl-benzene-1,3-diamine

Isopropyl-(3-nitro-phenyl)-[3-(2-trimethylsilanyl-ethoxymethyl)-3H-imidazol-4-ylmethyl]-amine (0.2 g, 0.51 mmol) was dissolved in ethanol, palladium on charcoal (20 mg, 10% Pd) was added and the mixture was hydrogenated overnight. The catalyst was filtered off and the solvent was evaporated. The residue was dissolved in ethyl acetate and filtered over silica gel. After evaporation the residue was dissolved in hydrochloric acid in ethanol (5M, 1 ml) and stirred at 60° C. for 2 hours. The solvent was evaporated and the residue was partitioned between sodium hydroxide solution (10%) and dichloromethane. After separation the aqueous layer was extracted again with dichloromethane. The combined organic layers were dried over magnesium sulphate and evaporated. The residue was purified using flash chromatography (column: Isolute® Flash-NH₂ from Separtis; eluent: ethyl acetate/methanol=90:10) to yield a light yellow gum, (0.054 g, 51%); MS (ISP): 231.4 ((M+H)⁺.).

Example 91

(5-Fluoro-2-methoxy-phenyl)-(1H-imidazol-4-ylmethyl)-isopropyl-amine

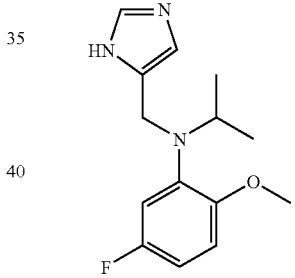

The title compound, MS (ISP): 263.9 ((M+H)⁺.) was obtained analogous to the procedure described for Example 67 using 5-fluoro-2-methoxy-aniline instead of 4-trifluoromethoxyaniline in step a).

Example 92

(2,5-Difluoro-phenyl)-(3H-imidazol-4-ylmethyl)-isopropyl-amine

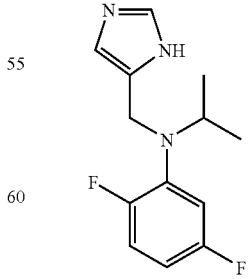

The title compound, MS (ISP): 251.9 ((M+H)⁺.) was obtained analogous to the procedure described for Example 67 using 2,5-difluoroaniline instead of 4-trifluoromethoxyaniline in step a).

Example 93

(4-Bromo-3-fluoro-phenyl)-(3H-imidazol-4-ylmethyl)-isopropyl-amine

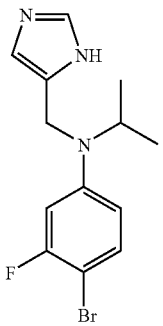 [SMILES: CC(C)N(Cc1cnc[nH]1)c1ccc(Br)c(F)c1]

The title compound, MS (ISP): 251.9 ((M+H)+.) was obtained analogous to the procedure described for Example 67 using 4-bromo-3-fluoroaniline instead of 4-trifluoromethoxyaniline in step a).

Example 94

(2-Chloro-phenyl)-ethyl-(2-methyl-3H-imidazol-4-ylmethyl)-amine

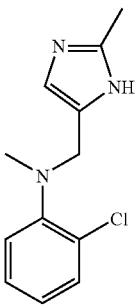 [SMILES: Cc1ncc(CN(C)c2ccccc2Cl)[nH]1]

The title compound, MS (ISP): 250.3; 252.3 ((M+H)+.) was obtained in comparable yield analogous to the procedure described for Example 81 using 2-chloroaniline instead of 3-chloro-2-fluoroaniline and 4-formyl-2-methyl-imidazole instead of 4-formylimidazole in step a).

Example 95

(4-Chloro-phenyl)-ethyl-(2-methyl-3H-imidazol-4-ylmethyl)-amine

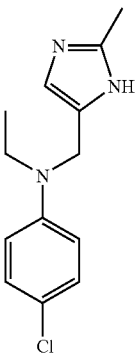

The title compound, MS (ISP): 250.1; 252.2 ((M+H)+.) was obtained in comparable yield analogous to the procedure described for Example 81 using 4-chloroaniline instead of 3-chloro-2-fluoroaniline and 4-formyl-2-methyl-imidazole instead of 4-formylimidazole in step a).

Example 96

Ethyl-(3-methoxy-phenyl)-(2-methyl-3H-imidazol-4-ylmethyl)-amine

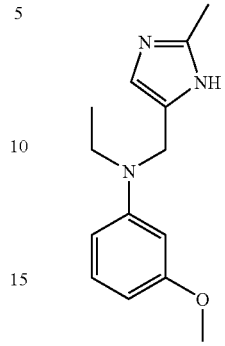

The title compound, MS (ISP): 246.3 ((M+H)+.) was obtained in comparable yield analogous to the procedure described for Example 81 using 3-methoxyaniline instead of 3-chloro-2-fluoroaniline and 4-formyl-2-methyl-imidazole instead of 4-formylimidazole in step a).

Example 97

Ethyl-(2-methyl-3H-imidazol-4-ylmethyl)-phenyl-amine

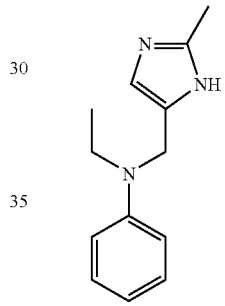

The title compound, MS (ISP): 216.3 ((M+H)+.) was obtained in comparable yield analogous to the procedure described for Example 81 using aniline instead of 3-chloro-2-fluoroaniline and 4-formyl-2-methyl-imidazole instead of 4-formylimidazole in step a).

Example 98

(4-Chloro-phenyl)-isopropyl-(2-methyl-3H-imidazol-4-ylmethyl)-amine

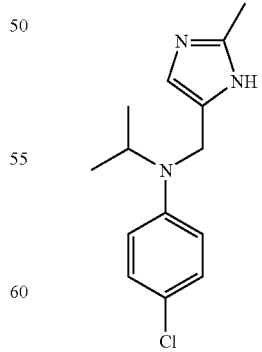

The title compound, MS (ISP): 264.0 ((M+H)+.) was obtained analogous to the procedure described for Example 67 using 4-chloroaniline instead of 4-trifluoromethoxyaniline and 4-formyl-2-methyl-imidazole instead of 4-formylimidazole in step a).

Example 99

Isopropyl-(2-methyl-3H-imidazol-4-ylmethyl)-phenyl-amine

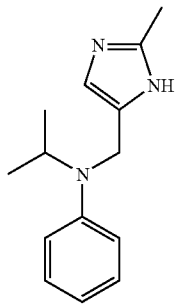 [SMILES: Cc1ncc(CN(c2ccccc2)C(C)C)[nH]1]

The title compound, MS (ISP): 230.3 ((M+H)$^+$.) was obtained analogous to the procedure described for Example 67 using aniline instead of 4-trifluoromethoxyaniline and 4-formyl-2-methyl-imidazole instead of 4-formylimidazole in step a).

Example 100

Isopropyl-(3-methoxy-phenyl)-(2-methyl-3H-imidazol-4-ylmethyl)-amine

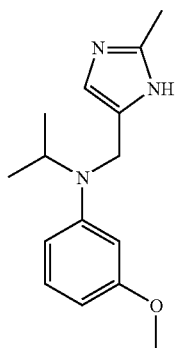 [SMILES: COc1cccc(N(Cc2cnc(C)[nH]2)C(C)C)c1]

The title compound, MS (ISP): 260.3 ((M+H)$^+$.) was obtained analogous to the procedure described for Example 67 using 3-methoxyaniline instead of 4-trifluoromethoxyaniline and 4-formyl-2-methyl-imidazole instead of 4-formylimidazole in step a).

Example 101

(3,5-Difluoro-phenyl)-(3H-imidazol-4-ylmethyl)-isopropyl-amine

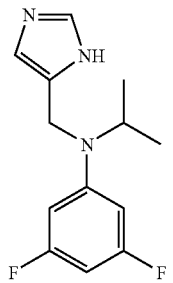

The title compound, MS (ISP): 252.3 ((M+H)$^+$.) was obtained analogous to the procedure described for Example 67 using 3,5-difluoroaniline instead of 4-trifluoromethoxyaniline in step a).

Example 102

(2,4-Difluoro-3-methoxy-phenyl)-(3H-imidazol-4-ylmethyl)-isopropyl-amine

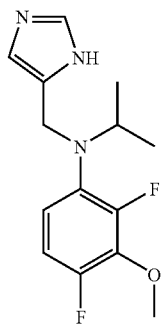 [SMILES: COc1c(F)ccc(N(Cc2cnc[nH]2)C(C)C)c1F]

The title compound, MS (ISP): 282.4 ((M+H)$^+$.) was obtained analogous to the procedure described for Example 67 using 2,4-difluoro-3-methoxyaniline instead of 4-trifluoromethoxyaniline in step a).

Example 103

(3-Fluoro-4-trifluoromethyl-phenyl)-(3H-imidazol-4-ylmethyl)-isopropyl-amine

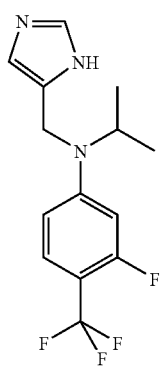 [SMILES: CC(C)N(Cc1cnc[nH]1)c1ccc(C(F)(F)F)c(F)c1]

The title compound, MS (ISP): 302.4 ((M+H)$^+$.) was obtained analogous to the procedure described for Example 67 using 3-fluoro-4-trifluoromethyl-aniline instead of 4-trifluoromethoxyaniline in step a).

Example 104

(2-Chloro-phenyl)-(3H-imidazol-4-ylmethyl)-isopropyl-amine

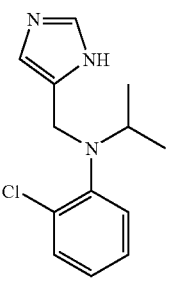 [SMILES: CC(C)N(Cc1cnc[nH]1)c1ccccc1Cl]

The title compound, MS (ISP): 250.1 ((M+H)$^+$.) was obtained analogous to the procedure described for Example 67 using 2-chloroaniline instead of 4-trifluoromethoxyaniline in step a).

Example 105

(4-Chloro-phenyl)-ethyl-(5-methyl-3H-imidazol-4-ylmethyl)-amine

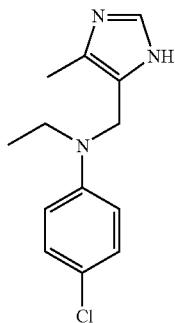 [SMILES: CCN(Cc1[nH]cnc1C)c1ccc(Cl)cc1]

The title compound, MS (ISP): 249.9 ((M+H)⁺.) was obtained analogous to the procedure described for Example 81 using 4-chloroaniline instead of 3-chloro-2-fluoroaniline and 4-formyl-5-methyl-imidazole instead of 4-formylimidazole in step a).

Example 106

Isopropyl-(5-methyl-3H-imidazol-4-ylmethyl)-phenyl-amine

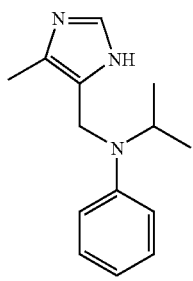 [SMILES: Cc1nc[nH]c1CN(c1ccccc1)C(C)C]

The title compound, MS (ISP): 230.0 ((M+H)⁺.) was obtained analogous to the procedure described for Example 67 using aniline instead of 4-trifluoromethoxyaniline and 4-formyl-5-methyl-imidazole instead of 4-formylimidazole in step a).

Example 107

Isopropyl-(3-methoxy-phenyl)-(5-methyl-3H-imidazol-4-ylmethyl)-amine

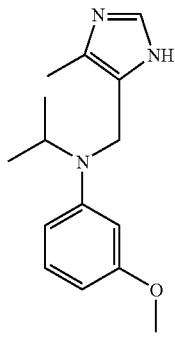 [SMILES: COc1cccc(N(Cc2[nH]cnc2C)C(C)C)c1]

The title compound, MS (ISP): 260.0 ((M+H)⁺.) was obtained analogous to the procedure described for Example 67 using 3-methoxyaniline instead of 4-trifluoromethoxyaniline and 4-formyl-5-methyl-imidazole instead of 4-formylimidazole in step a).

Example 108

(3H-Imidazol-4-ylmethyl)-isopropyl-(2,3,4-trifluoro-phenyl)-amine

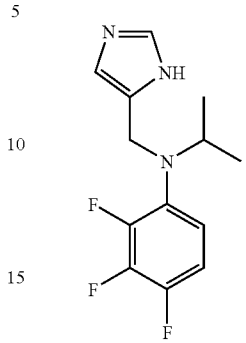

The title compound, MS (ISP): 270.4 ((M+H)⁺.) was obtained analogous to the procedure described for Example 67 using 2,3,4-trifluoroaniline instead of 4-trifluoromethoxyaniline in step a).

Example 109

(4-Fluoro-3-methyl-phenyl)-(3H-imidazol-4-ylmethyl)-isopropyl-amine

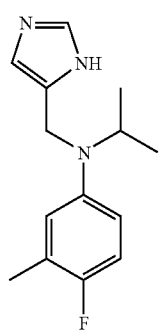 [SMILES: Cc1cc(N(Cc2cnc[nH]2)C(C)C)ccc1F]

The title compound, MS (ISP): 248.2 ((M+H)⁺.) was obtained analogous to the procedure described for Example 67 using 4-trifluoro-3-methylaniline instead of 4-trifluoromethoxyaniline in step a).

Example 110

(3H-Imidazol-4-ylmethyl)-(3-isopropoxy-phenyl)-isopropyl-amine

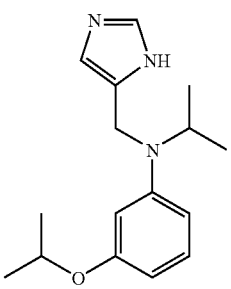 [SMILES: CC(C)Oc1cccc(N(Cc2cnc[nH]2)C(C)C)c1]

The title compound, MS (ISP): 274.4 ((M+H)⁺.) was obtained analogous to the procedure described for Example 67 using 3-isopropoxyaniline instead of 4-trifluoromethoxyaniline in step a).

Example 111

N-{3-[(3H-Imidazol-4-ylmethyl)-isopropyl-amino]-phenyl}-acetamide

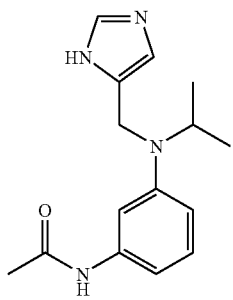 [SMILES: CC(=O)Nc1cccc(N(Cc2cnc[nH]2)C(C)C)c1]

Isopropyl-(3-nitro-phenyl)-[3-(2-trimethylsilanyl-ethoxymethyl)-3H-imidazol-4-ylmethyl]-amine (0.055 g, 0.14 mmol) was dissolved in ethanol, palladium on charcoal (20 mg, 10% Pd) was added and the mixture was hydrogenated overnight. The catalyst was filtered off and the solvent was evaporated. The residue was dissolved in ethyl acetate and filtered over silica gel. After evaporation the residue was dissolved in toluene (1.5 ml) and tetrahydrofuran (3 ml), acetic anhydride (0.015 mg, 0.14 mmol) was added and the mixture was stirred overnight. The solvents were evaporated and the residue was partitioned between sodium bicarbonate solution and ethyl acetate. The organic layer was dried over magnesium sulphate and evaporated. The residue was dissolved in tetrahydrofuran (5 ml) and tetrabutylammonium fluoride solution (0.3 ml, 1M) in tetrahydrofuran was added. After stirring the mixture at 65° C. overnight the solvent was evaporated and the residue was purified by flash chromatography (column: Isolute® Flash-NH$_2$ from Separtis; eluent: ethyl acetate/methanol=95:5) to yield a white gum, (0.005 g, 34%); MS (ISP): 273.2 ((M+H)$^+$.).

Example 112

(3H-Imidazol-4-ylmethyl)-isopropyl-(2-methoxy-pyridin-4-yl)-amine

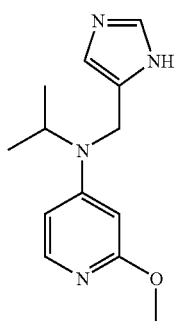 [SMILES: COc1cc(N(Cc2cnc[nH]2)C(C)C)ccn1]

The title compound, MS (ISP): 247.3 ((M+H)$^+$.) was obtained analogous to the procedure described for Example 67 using 4-amino-2-methoxypyridine instead of 4-trifluoromethoxyaniline in step a).

Example 113

(3H-Imidazol-4-ylmethyl)-isopropyl-(6-methoxy-pyridin-2-yl)-amine

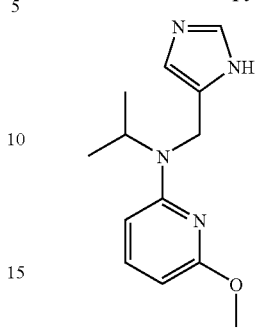

The title compound, MS (ISP): 247.3 ((M+H)$^+$.) was obtained analogous to the procedure described for Example 67 using 2-amino-6-methoxypyridine instead of 4-trifluoromethoxyaniline in step a).

Example 114

(3-Benzyloxy-phenyl)-(3H-imidazol-4-ylmethyl)-isopropyl-amine

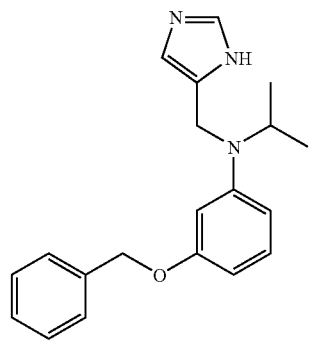 [SMILES: CC(C)N(Cc1cnc[nH]1)c1cccc(OCc2ccccc2)c1]

The title compound, MS (ISP): 322.3 ((M+H)$^+$.) was obtained analogous to the procedure described for Example 67 using 3-benzyloxy-aniline instead of 4-trifluoromethoxyaniline in step a).

Example 115

(3H-Imidazol-4-ylmethyl)-isopropyl-(3-trifluoromethoxy-phenyl)-amine

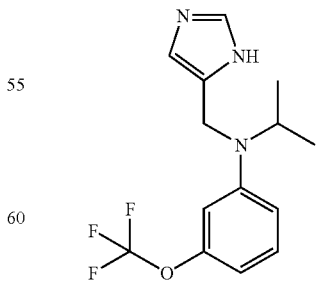

The title compound, MS (ISP): 300.1 ((M+H)$^+$.) was obtained analogous to the procedure described for Example 67 using 3-trifluoromethoxyaniline instead of 4-trifluoromethoxyaniline in step a).

Example 116

Isopropyl-(3-methoxy-phenyl)-(3-methyl-3H-imidazol-4-ylmethyl)-amine

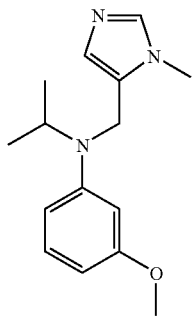 [SMILES: COc1cccc(N(Cc2cncn2C)C(C)C)c1]

The title compound, MS (ISP): 260.0 ((M+H)+.) was obtained analogous to the procedure described for Example 67 using 3-methoxyaniline instead of 4-trifluoromethoxyaniline and 4-formyl-1-methyl-imidazole instead of 4-formylimidazole in step a).

Example 117

(4-Fluoro-3-methoxy-phenyl)-(3H-imidazol-4-ylmethyl)-isopropyl-amine

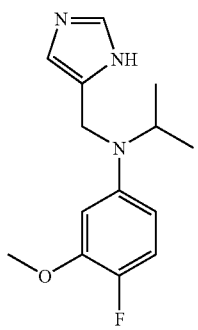 [SMILES: COc1cc(N(Cc2cnc[nH]2)C(C)C)ccc1F]

The title compound, MS (ISP): 264.0 ((M+H)+.) was obtained analogous to the procedure described for Example 67 using 4-fluoro-3-methoxyaniline instead of 4-trifluoromethoxyaniline in step a).

Example 118

(3,5-Dimethoxy-phenyl)-(3H-imidazol-4-ylmethyl)-isopropyl-amine

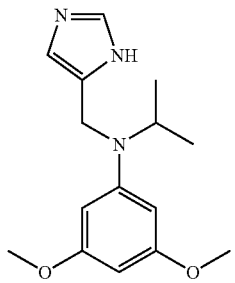

The title compound, MS (ISP): 276.4 ((M+H)+.) was obtained analogous to the procedure described for Example 67 using 3,5-dimethoxyaniline instead of 4-trifluoromethoxyaniline in step a).

Example 119

3-[(3H-Imidazol-4-ylmethyl)-isopropyl-amino]-phenol

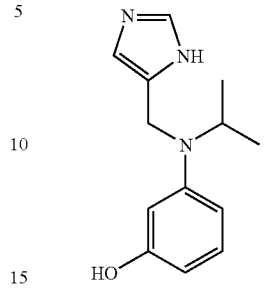

(3-Benzyloxy-phenyl)-(3H-imidazol-4-ylmethyl)-isopropyl-amine (0.109 g, 0.34 mmol) was dissolved in ethanol (10 ml), palladium on charcoal (10 mg, 10% Pd) was added and the mixture was hydrogenated overnight at room temperature. The catalyst was filtered off and the solvent was evaporated. The residue was purified by flash chromatography (column: Isolute® Flash-NH$_2$ from Separtis; eluent: ethyl acetate/methanol=95:5) to yield a white foam, (0.042 g, 53%); MS (ISP): 232.1 ((M+H)+.).

Example 120

3-[Ethyl-(3H-imidazol-4-ylmethyl)-amino]-N-methyl-benzamide

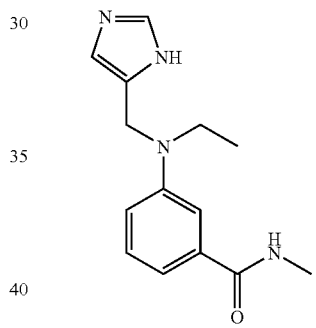

The title compound, MS (ISP): 259.3 ((M+H)+.) was obtained in comparable yield analogous to the procedure described for Example 81 using 3-amino-benzoylmethylamide instead of 3-chloro-2-fluoroaniline in step a).

Example 121

{3-[(3H-Imidazol-4-ylmethyl)-isopropyl-amino]-phenyl}-methanol

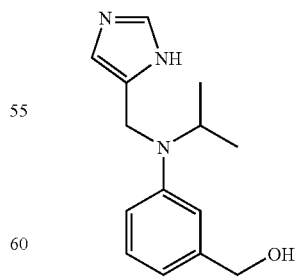

a) [3-tert-Butyl-dimethyl-silanyloxymethyl]phenyl]-(3H-imidazol-4-ylmethyl)-isopropyl-amine

[3-tert-Butyl-dimethyl-silanyloxymethyl]phenyl]-(3H-imidazol-4-ylmethyl)-isopropyl-amine, MS (ISP): 228.4

((M-TBDMSO)$^+$.), 360.5 ((M+H)$^+$.) was obtained analogous to the procedure described for Example 67 using 3-(tert-butyl-dimethylsilanyloxymethyl)-phenylamine instead of 4-trifluoromethoxyaniline in step a).

b) {3-[(3H-Imidazol-4-ylmethyl)-isopropyl-amino]-phenyl}-methanol

[3-tert-Butyl-dimethyl-silanyloxymethyl]phenyl]-(3H-imidazol-4-ylmethyl)-isopropyl-amine (0.724 g, 2 mmol) was dissolved in tetrahydrofuran (20 ml) and tetrabutylammonium fluoride solution (4 ml, 1M) in tetrahydrofuran was added. After stirring the mixture at room temperature overnight the solvent was evaporated and the residue was purified by flash chromatography (SiO2, eluent: ethyl acetate) to yield a colourless gum, (0.252 g, 51%); MS (ISP): 246.4 ((M+H)$^+$.).

Example 122

(3-Ethoxy-phenyl)-(3H-imidazol-4-ylmethyl)-isopropyl-amine

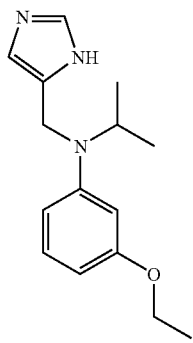 [SMILES: CCOc1cccc(N(Cc2cnc[nH]2)C(C)C)c1]

The title compound, MS (ISP): 260.1 ((M+H)$^+$.) was obtained analogous to the procedure described for Example 67 using 3-ethoxyaniline instead of 4-trifluoromethoxyaniline in step a).

Example 123

(3H-Imidazol-4-ylmethyl)-isopropyl-(3-phenoxy-phenyl)-amine

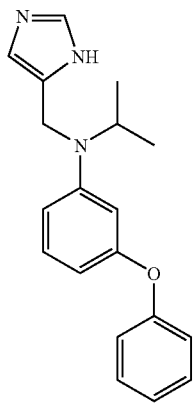 [SMILES: CC(C)N(Cc1cnc[nH]1)c1cccc(Oc2ccccc2)c1]

The title compound, MS (ISP): 308.4 ((M+H)$^+$.) was obtained analogous to the procedure described for Example 67 using 3-phenoxyaniline instead of 4-trifluoromethoxyaniline in step a).

Example 124

((3-Difluoromethoxy-phenyl)-(3H-imidazol-4-ylmethyl)-isopropyl-amine

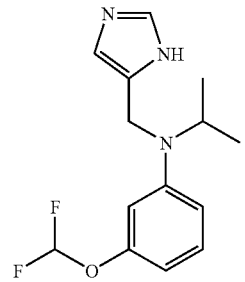 [SMILES: CC(C)N(Cc1cnc[nH]1)c1cccc(OC(F)F)c1]

The title compound, MS (ISP): 282.4 ((M+H)$^+$.) was obtained analogous to the procedure described for Example 67 using 3-difluoromethoxyaniline instead of 4-trifluoromethoxyaniline in step a).

Example 125

(3H-Imidazol-4-ylmethyl)-isopropyl-[3-(1,1,2,2-tetrafluoro-ethoxy)-phenyl]-amine

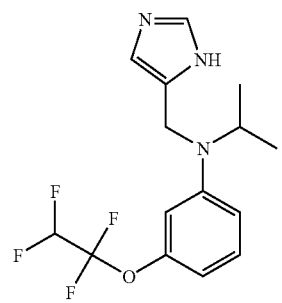 [SMILES: CC(C)N(Cc1cnc[nH]1)c1cccc(OC(F)(F)C(F)F)c1]

The title compound, MS (ISP): 332.3 ((M+H)$^+$.) was obtained analogous to the procedure described for Example 67 using 1,1,2,2-tetrafluoro-ethoxy-aniline instead of 4-trifluoromethoxyaniline in step a).

Example 126

(3-Chloro-4-morpholin-4-yl-phenyl)-ethyl-(1H-imidazol-4-ylmethyl)-amine

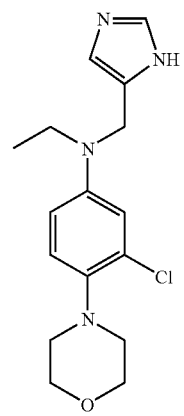 [SMILES: CCN(Cc1cnc[nH]1)c1ccc(N2CCOCC2)c(Cl)c1]

The title compound, MS (ISP): 321.1 ((M+H)$^+$.) was obtained in comparable yield analogous to the procedure described for Example 81 using 3-chloro-4-morpholin-4-yl-phenylamine instead of 3-chloro-2-fluoroaniline in step a).

Example 127

(3-Chloro-4-morpholin-4-yl-phenyl)-(1H-imidazol-4-ylmethyl)-isopropyl-amine

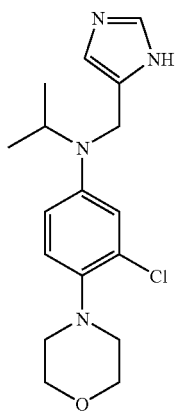 [SMILES: CC(C)N(Cc1cnc[nH]1)c1ccc(N2CCOCC2)c(Cl)c1]

The title compound, MS (ISP): 335.4 ((M+H)+.) was obtained analogous to the procedure described for Example 67 using 3-chloro-4-morpholin-4-yl-phenylamine instead of 4-trifluoromethoxyaniline in step a).

Example 128

(3-Chloro-4-methyl-phenyl)-(1H-imidazol-4-ylmethyl)-isopropyl-amine

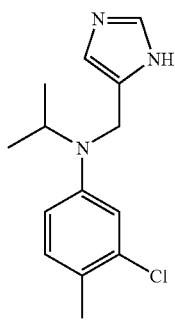 [SMILES: Cc1ccc(N(Cc2cnc[nH]2)C(C)C)cc1Cl]

The title compound, MS (ISP): 264.0 ((M+H)+.) was obtained analogous to the procedure described for Example 67 using 3-chloro-4-methylaniline instead of 4-trifluoromethoxyaniline in step a).

Example 129

(2-Fluoro-3-methoxy-phenyl)-(3H-imidazol-4-ylmethyl)-isopropyl-amine

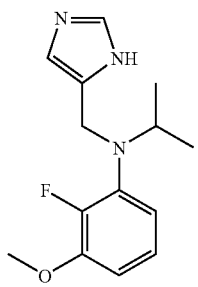 [SMILES: COc1cccc(N(Cc2cnc[nH]2)C(C)C)c1F]

The title compound, MS (ISP): 264.0 ((M+H)+.) was obtained analogous to the procedure described for Example 67 using 2-fluoro-3-methoxy-aniline instead of 4-trifluoromethoxyaniline in step a).

Example 130

(3,4-Dimethyl-phenyl)-ethyl-(1H-imidazol-4-ylmethyl)-amine

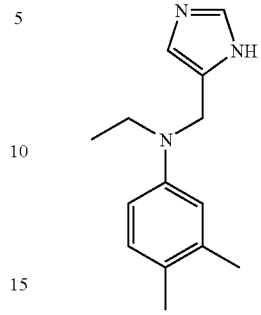

The title compound, MS (ISP): 230.3 ((M+H)+.) was obtained analogous to the procedure described for Example 81 using 3,4-dimethylaniline instead of 3-chloro-2-fluoroaniline in step a).

Example 131

1-{4-[Ethyl-(1H-imidazol-4-ylmethyl)-amino]-3-fluoro-phenyl}-1H-pyridin-2-one

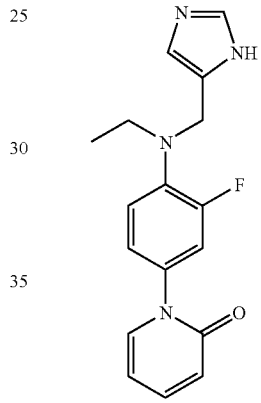

The title compound, MS (ISP): 313.3 ((M+H)+.) was obtained analogous to the procedure described for Example 81 using 1-(4-amino-3-fluoro-phenyl)-1H-pyridin-2-one instead of 3-chloro-2-fluoroaniline in step a).

Example 132

1-{3-Fluoro-4-[(H-imidazol-4-ylmethyl)-isopropyl-amino]-phenyl}-1H-pyridin-2-one

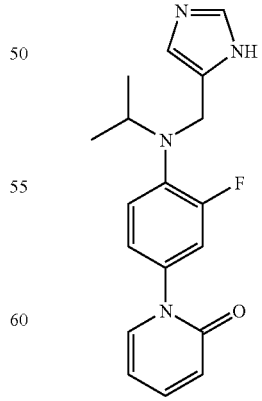

The title compound, MS (ISP): 327.3 ((M+H)+.) was obtained analogous to the procedure described for Example 67 using 1-(4-amino-3-fluoro-phenyl)-1H-pyridin-2-one instead of 4-trifluoromethoxyaniline in step a).

Example 133

(4-Benzyloxy-3-chloro-phenyl)-(1H-imidazol-4-ylmethyl)-isopropyl-amine

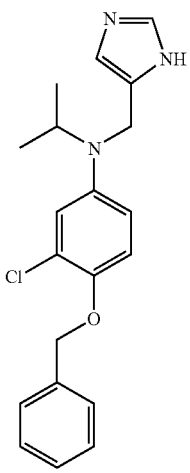 [SMILES: CC(C)N(Cc1cnc[nH]1)c1ccc(OCc2ccccc2)c(Cl)c1]

The title compound, MS (ISP): 356.5 ((M+H)$^+$.) was obtained analogous to the procedure described for Example 67 using 4-benzyloxy-3-chloroaniline instead of 4-trifluoromethoxyaniline in step a).

Example 134

(4-Benzyloxy-3-chloro-phenyl)-ethyl-(1H-imidazol-4-ylmethyl)-amine

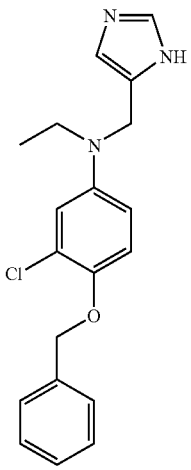 [SMILES: CCN(Cc1cnc[nH]1)c1ccc(OCc2ccccc2)c(Cl)c1]

The title compound, MS (ISP): 342.1 ((M+H)$^+$.) was obtained analogous to the procedure described for Example 81 using 4-benzyloxy-3-chloroaniline instead of 3-chloro-2-fluoroaniline in step a).

Example 135

(3H-Imidazol-4-ylmethyl)-isopropyl-[3-(pyridin-3-yloxy)-phenyl]-amine

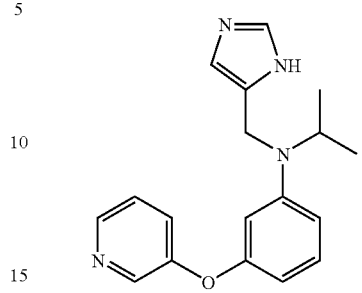

The title compound, MS (ISP): 309.6 ((M+H)$^+$.) was obtained analogous to the procedure described for Example 67 using 3-(pyridine-3-yloxy)-phenylamine instead of 4-trifluoromethoxyaniline in step a).

Example 136

(3H-Imidazol-4-ylmethyl)-isopropyl-(4-phenoxy-phenyl)-amine

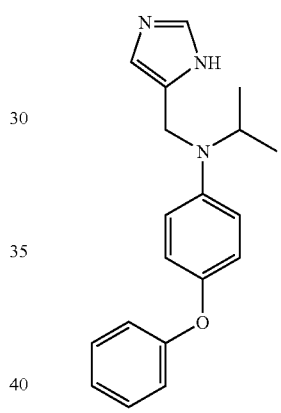

The title compound, MS (ISP): 308.3 ((M+H)$^+$.) was obtained analogous to the procedure described for Example 67 using 4-phenoxyaniline instead of 4-trifluoromethoxyaniline in step a).

Example 137

(3H-Imidazol-4-ylmethyl)-isopropyl-[2-methoxy-5-(1-methyl-1-phenyl-ethyl)-phenyl]-amine

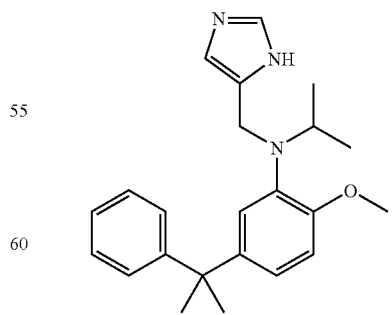

The title compound, MS (ISP): 364.2 ((M+H)$^+$.) was obtained analogous to the procedure described for Example 67 using 2-methoxy-5-(1-methyl-1-phenyl-ethyl)-phenylamine instead of 4-trifluoromethoxyaniline in step a).

Example 138

[3-Chloro-4-(4-chloro-phenoxy)-phenyl]-(1H-imidazol-4-ylmethyl)-isopropyl-amine

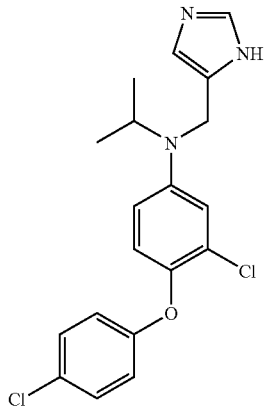 [SMILES: CC(C)N(Cc1cnc[nH]1)c1ccc(Oc2ccc(Cl)cc2)c(Cl)c1]

The title compound, MS (ISP): 376.1 ((M+H)+.) was obtained analogous to the procedure described for Example 67 using 3-chloro-4-(4-chloro-phenoxy)-phenylamine instead of 4-trifluoromethoxyaniline in step a).

Example 139

[3-Chloro-4-(4-chloro-phenoxy)-phenyl]-ethyl-(1H-imidazol-4-ylmethyl)-amine

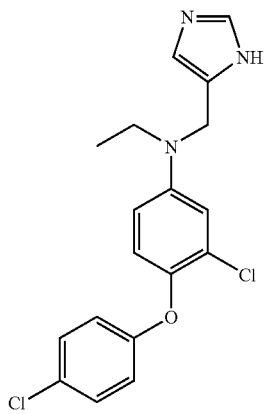 [SMILES: CCN(Cc1cnc[nH]1)c1ccc(Oc2ccc(Cl)cc2)c(Cl)c1]

The title compound, MS (ISP): 362.3 ((M+H)+.) was obtained analogous to the procedure described for Example 81 using 3-chloro-4-(4-chloro-phenoxy)-phenylamine instead of 3-chloro-2-fluoroaniline in step a).

Example 140

(3H-Imidazol-4-ylmethyl)-isopropyl-[3-(2-methoxy-phenoxy)-phenyl]-amine

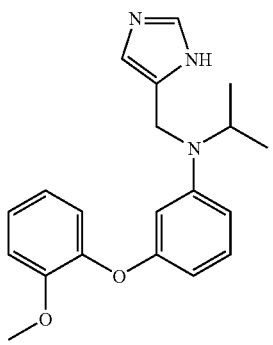 [SMILES: COc1ccccc1Oc1cccc(N(Cc2cnc[nH]2)C(C)C)c1]

The title compound, MS (ISP): 338.4 ((M+H)+.) was obtained analogous to the procedure described for Example 67 using 3-(2-methoxy-phenoxy)-phenylamine instead of 4-trifluoromethoxyaniline in step a).

Example 141

(3-Benzyl-phenyl)-(3H-imidazol-4-ylmethyl)-isopropyl-amine

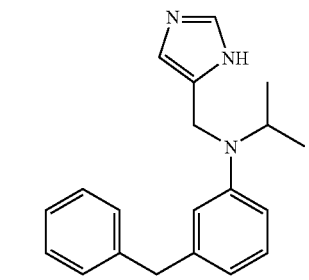 [SMILES: CC(C)N(Cc1cnc[nH]1)c1cccc(Cc2ccccc2)c1]

The title compound, MS (ISP): 306.4 ((M+H)+.) was obtained analogous to the procedure described for Example 67 using 3-benzylaniline instead of 4-trifluoromethoxyaniline in step a).

Example 142

Biphenyl-3-yl-(3H-imidazol-4-ylmethyl)-isopropyl-amine

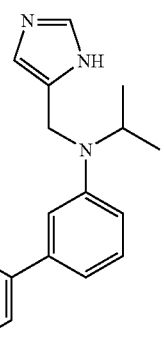

The title compound, MS (ISP): 292.4 ((M+H)+.) was obtained analogous to the procedure described for Example 67 using 3-aminobiphenyl instead of 4-trifluoromethoxyaniline in step a).

Example 143

(3H-Imidazol-4-ylmethyl)-(2-phenoxy-pyridin-4-yl)-amine

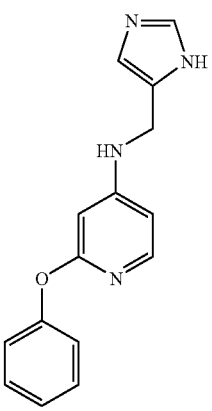 [SMILES: c1ccc(Oc2cc(NCc3cnc[nH]3)ccn2)cc1]

The title compound, MS (ISP): 267.1 ((M+H)+.) was obtained in comparable yield analogous to the procedure described for Example 1 using 2-phenoxy-pyridin-4-yl-amine instead of N-ethylaniline.

Example 144

[6-(4-Chloro-phenoxy)-pyridin-3-yl]-(3H-imidazol-4-ylmethyl)-amine

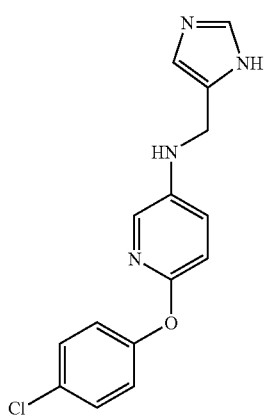 [SMILES: Clc1ccc(Oc2ccc(NCc3cnc[nH]3)cn2)cc1]

The title compound, MS (ISP): 301.1; 303.0 ((M+H)+.) was obtained in comparable yield analogous to the procedure described for Example 1 using 6-(4-chloro-phenoxy-pyridin-3-yl-amine instead of N-ethylaniline.

Example 145

[6-(4-Chloro-phenoxy)-pyridin-3-yl]-ethyl-(3H-imidazol-4-ylmethyl)-amine

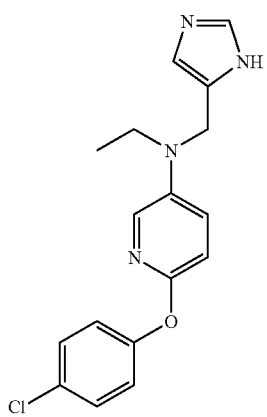 [SMILES: CCN(Cc1cnc[nH]1)c1ccc(Oc2ccc(Cl)cc2)nc1]

The title compound, MS (ISP): 329.1; 331.1 ((M+H)+.) was obtained analogous to the procedure described for Example 81 using 6-(4-chloro-phenoxy-pyridin-3-yl-amine instead of 3-chloro-2-fluoroaniline in step a).

Example 146

(3H-Imidazol-4-ylmethyl)-isopropyl-[4-(4-trifluoromethyl-phenoxy)-phenyl]-amine

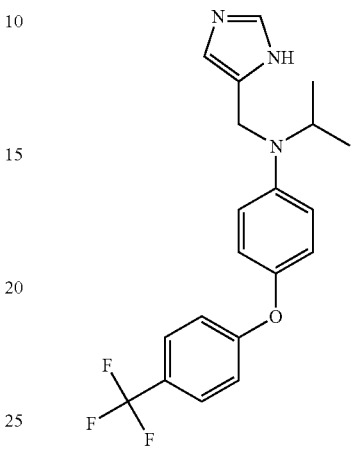

The title compound, MS (ISP): 376.3 ((M+H)+.) was obtained analogous to the procedure described for Example 67 using 4-(4-trifluoromethoxy-phenoxy)-aniline instead of 4-trifluoromethoxyaniline in step a).

Example 147

(3H-Imidazol-4-ylmethyl)-isopropyl-[4-(4-methoxy-phenoxy)-phenyl]-amine

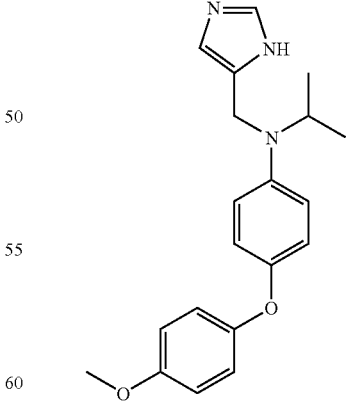

The title compound, MS (ISP): 338.5 ((M+H)+.) was obtained analogous to the procedure described for Example 67 using 4-(4-methoxy-phenoxy)-aniline instead of 4-trifluoromethoxyaniline in step a).

Example 148

(3H-Imidazol-4-ylmethyl)-isopropyl-[4-(2-methoxy-phenoxy)-phenyl]-amine

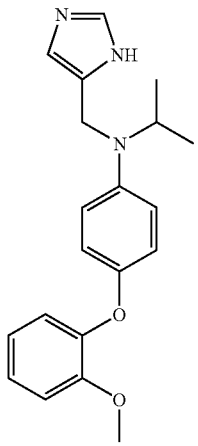 [SMILES: COc1ccccc1Oc1ccc(N(Cc2cnc[nH]2)C(C)C)cc1]

The title compound, MS (ISP): 338.4 ((M+H)$^+$.) was obtained analogous to the procedure described for Example 67 using 4-(2-methoxy-phenoxy)-aniline instead of 4-trifluoromethoxyaniline in step a).

Example 149

[3-(4-Chloro-phenoxy)-phenyl]-(3H-imidazol-4-ylmethyl)-isopropyl-amine

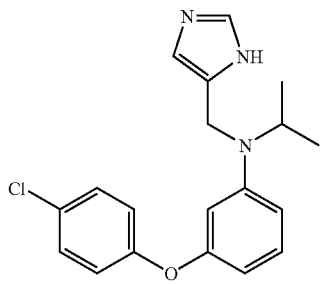 [SMILES: CC(C)N(Cc1cnc[nH]1)c1cccc(Oc2ccc(Cl)cc2)c1]

The title compound, MS (ISP): 342.1 ((M+H)$^+$.) was obtained analogous to the procedure described for Example 67 using 3-(4-chloro-phenoxy)-aniline instead of 4-trifluoromethoxyaniline in step a).

Example 150

(3H-Imidazol-4-ylmethyl)-isopropyl-(4-phenylsulfanyl-phenyl)-amine

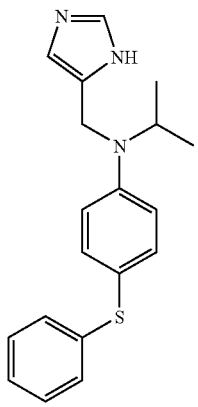 [SMILES: CC(C)N(Cc1cnc[nH]1)c1ccc(Sc2ccccc2)cc1]

The title compound, MS (ISP): 324.5 ((M+H)$^+$.) was obtained analogous to the procedure described for Example 67 using 4-phenylsulfanyl-phenylamine instead of 4-trifluoromethoxyaniline in step a).

Example 151

[4-(3,4-Dichloro-phenoxy)-phenyl]-(3H-imidazol-4-ylmethyl)-isopropyl-amine

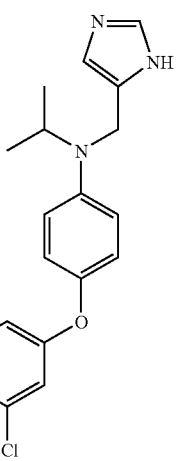

The title compound, MS (ISP): 376.2; 378.1 ((M+H)$^+$.) was obtained analogous to the procedure described for Example 67 using 4-(3,4-dichloro-phenoxy)-phenylamine instead of 4-trifluoromethoxyaniline in step a).

Example 152

[4-(4-Chloro-phenoxy)-phenyl]-(3H-imidazol-4-ylmethyl)-isopropyl-amine

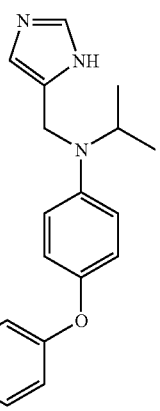

The title compound, MS (ISP): 342.0 ((M+H)$^+$.) was obtained analogous to the procedure described for Example 67 using 4-(4-chloro-phenoxy)-phenylamine instead of 4-trifluoromethoxyaniline in step a).

Example 153

[4-(2-Chloro-phenoxy)-phenyl]-(3H-imidazol-4-ylmethyl)-isopropyl-amine

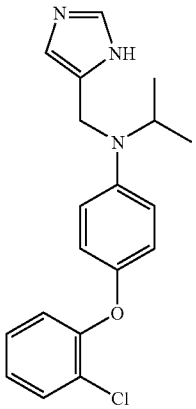 [SMILES: CC(C)N(Cc1cnc[nH]1)c1ccc(Oc2ccccc2Cl)cc1]

The title compound, MS (ISP): 342.1 ((M+H)+.) was obtained analogous to the procedure described for Example 67 using 4-(2-chloro-phenoxy)-phenylamine instead of 4-trifluoromethoxyaniline in step a).

Example 154

{3-[(3H-Imidazol-4-ylmethyl)-isopropyl-amino]-phenyl}-phenyl-methanol

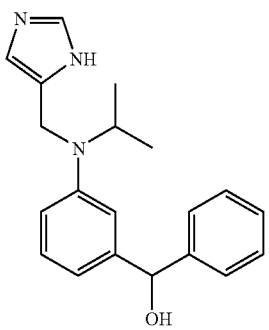 [SMILES: CC(C)N(Cc1cnc[nH]1)c1cccc(C(O)c2ccccc2)c1]

The title compound, MS (ISP): 322.4 ((M+H)+.) was obtained analogous to the procedure described for Example 67 using 3-amino-benzophenone instead of 4-trifluoromethoxyaniline in step a).

Example 155

N-(1H-Imidazol-4-ylmethyl)-N'-phenyl-benzene-1,4-diamine

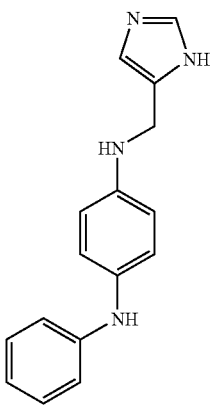 [SMILES: c1ccc(Nc2ccc(NCc3cnc[nH]3)cc2)cc1]

The title compound, MS (ISP): 265.1 ((M+H)+.) was obtained in comparable yield analogous to the procedure described for Example 81 using 4-aminodiphenylamine instead of 3-chloro-2-fluoroaniline in step a).

Example 156

(4-Benzyloxy-phenyl)-ethyl-(1H-imidazol-4-ylmethyl)-amine

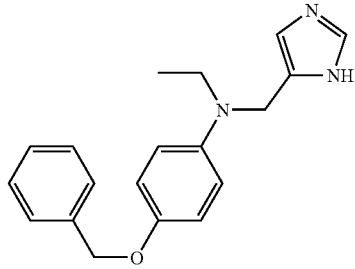 [SMILES: CCN(Cc1cnc[nH]1)c1ccc(OCc2ccccc2)cc1]

The title compound, MS (ISP): 308.4 ((M+H)+.) was obtained in comparable yield analogous to the procedure described for Example 81 using 4-benzyloxyaniline instead of 3-chloro-2-fluoroaniline in step a).

Example 157

{4-[2-(4-Chloro-phenyl)-ethyl]-phenyl}-(1H-imidazol-4-ylmethyl)-isopropyl-amine

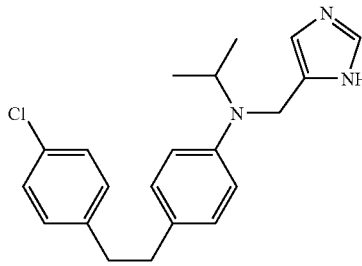

The title compound, MS (ISP): 354.3 ((M+H)+.) was obtained in comparable yield analogous to the procedure described for Example 67 using 4-[2-(4-chloro-phenyl)-ethyl]-phenylamine instead of 4-trifluoromethoxyaniline in step a).

Example 158

(4-Benzyloxy-phenyl)-(1H-imidazol-4-ylmethyl)-isopropyl-amine

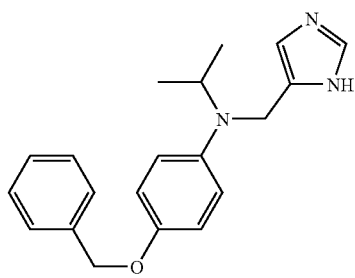 [SMILES: CC(C)N(Cc1cnc[nH]1)c1ccc(OCc2ccccc2)cc1]

The title compound, MS (ISP): 322.4 ((M+H)+.) was obtained in comparable yield analogous to the procedure described for Example 67 using 4-benzyloxyaniline instead of 4-trifluoromethoxyaniline in step a).

Example 159

N-(1H-Imidazol-4-ylmethyl)-N-isopropyl-N-phenyl-benzene-1,4-diamine

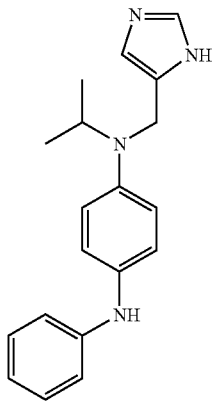 [SMILES: CC(C)N(Cc1cnc[nH]1)c1ccc(Nc2ccccc2)cc1]

The title compound, MS (ISP): 307.3 ((M+H)⁺.) was obtained in comparable yield analogous to the procedure described for Example 67 using 4-aminodiphenylamine instead of 4-trifluoromethoxyaniline in step a).

Example 160

1-{4-[(H-Imidazol-4-ylmethyl)-isopropyl-amino]-benzyl}-pyrrolidin-2-one

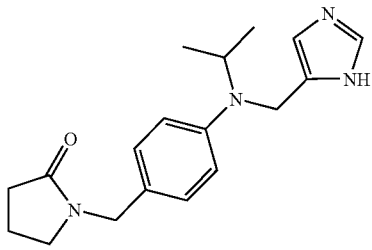 [SMILES: CC(C)N(Cc1cnc[nH]1)c1ccc(CN2CCCC2=O)cc1]

The title compound, MS (ISP): 313.4 ((M+H)⁺.) was obtained in comparable yield analogous to the procedure described for Example 67 using 1-(4-amino-benzyl)-pyrrolidin-2-one instead of 4-trifluoromethoxyaniline in step a).

Example 161

{4-[2-(4-Chloro-phenyl)-ethyl]-phenyl}-ethyl-(1H-imidazol-4-ylmethyl)-amine

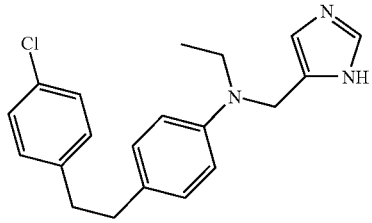 [SMILES: CCN(Cc1cnc[nH]1)c1ccc(CCc2ccc(Cl)cc2)cc1]

The title compound, MS (ISP): 304.5 ((M+H)⁺.) was obtained in comparable yield analogous to the procedure described for Example 81 using 4-[2-(4-chloro-phenyl)-ethyl]-phenylamine instead of 3-chloro-2-fluoroaniline in step a).

Example 162

1-{4-[Ethyl-(1H-imidazol-4-ylmethyl)-amino]-benzyl}-pyrrolidin-2-one

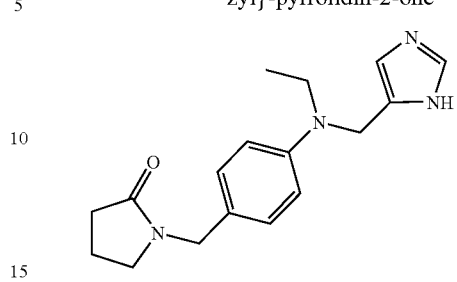

The title compound, MS (ISP): 299.4 ((M+H)⁺.) was obtained in comparable yield analogous to the procedure described for Example 81 using 1-(4-amino-benzyl)-pyrrolidin-2-one instead of 3-chloro-2-fluoroaniline in step a).

Example 163

(1H-Imidazol-4-ylmethyl)-isopropyl-(4-pyridin-4-ylmethyl-phenyl)-amine

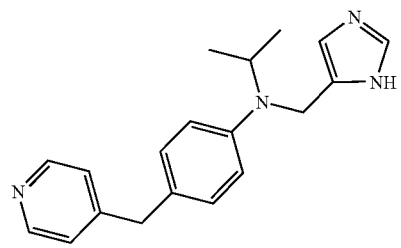 [SMILES: CC(C)N(Cc1cnc[nH]1)c1ccc(Cc2ccncc2)cc1]

The title compound, MS (ISP): 307.3 ((M+H)⁺.) was obtained in comparable yield analogous to the procedure described for Example 67 using 4-pyridin-4-ylmethyl-phenylamine instead of 4-trifluoromethoxyaniline in step a).

Example 164

N,N'-Diethyl-N-(1H-imidazol-4-ylmethyl)-N'-phenyl-benzene-1,4-diamine

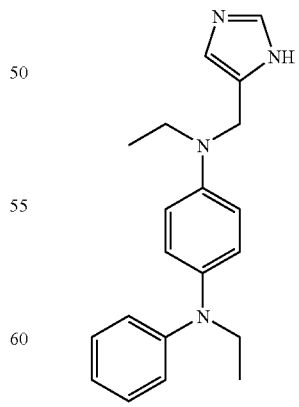

The title compound, MS (ISP): 321.1 ((M+H)⁺.) was obtained in comparable yield analogous to the procedure described for Example 81 using 4-aminodiphenylamine instead of 3-chloro-2-fluoroaniline in step a).

Example 165

[3-Chloro-4-(2-chloro-phenoxy)-phenyl]-(1H-imidazol-4-ylmethyl)-isopropyl-amine

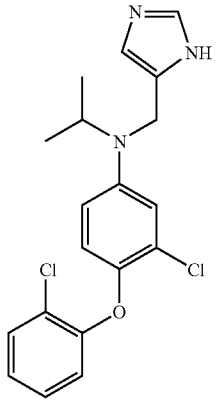 [SMILES: CC(C)N(Cc1cnc[nH]1)c1ccc(Oc2ccccc2Cl)c(Cl)c1]

The title compound, MS (ISP): 376.4 ((M+H)+.) was obtained in comparable yield analogous to the procedure described for Example 67 using 3-chloro-4-(2-chloro-phenoxy)-phenylamine instead of 4-trifluoromethoxyaniline in step a).

Example 166

[3-Chloro-4-(2-chloro-phenoxy)-phenyl]-ethyl-(1H-imidazol-4-ylmethyl)-amine

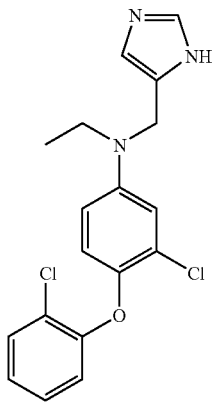 [SMILES: CCN(Cc1cnc[nH]1)c1ccc(Oc2ccccc2Cl)c(Cl)c1]

The title compound, MS (ISP): 362.4 ((M+H)+.) was obtained in comparable yield analogous to the procedure described for Example 81 using 3-chloro-4-(2-chloro-phenoxy)-phenylamine instead of 3-chloro-2-fluoroaniline in step a).

Example 167

C-{4-[(1H-Imidazol-4-ylmethyl)-isopropyl-amino]-phenyl}-N-methyl-methanesulfonamide

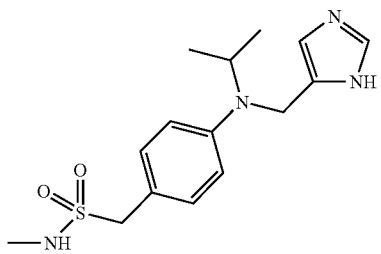 [SMILES: CNS(=O)(=O)Cc1ccc(N(Cc2cnc[nH]2)C(C)C)cc1]

The title compound, MS (ISP): 323.1 ((M+H)+.) was obtained in comparable yield analogous to the procedure described for Example 67 using C-(4-amino-phenyl)-N-methyl-methanesulfonamide instead of 4-trifluoromethoxyaniline in step a).

Example 168

C-{4-[Ethyl-(1H-imidazol-4-ylmethyl)-amino]-phenyl}-N-methyl-methanesulfonamide

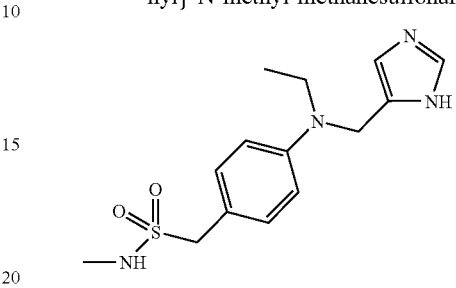

The title compound, MS (ISP): 309.5 ((M+H)+.) was obtained in comparable yield analogous to the procedure described for Example 81 using C-(4-amino-phenyl)-N-methyl-methanesulfonamide instead of 3-chloro-2-fluoroaniline in step a).

Example 169

[3-Chloro-4-(pyrimidin-2-yloxy)-phenyl]-(1H-imidazol-4-ylmethyl)-isopropyl-amine

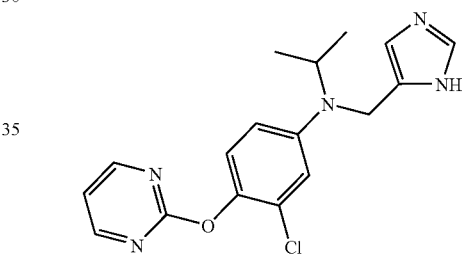

The title compound, MS (ISP): 344.3 ((M+H)+.) was obtained in comparable yield analogous to the procedure described for Example 67 using 3-chloro-4-(2-pyrimidinyloxy)phenylamine instead of 4-trifluoromethoxyaniline in step a).

Example 170

(3-Bromo-4-fluoro-phenyl)-(3H-imidazol-4-ylmethyl)-isopropyl-amine

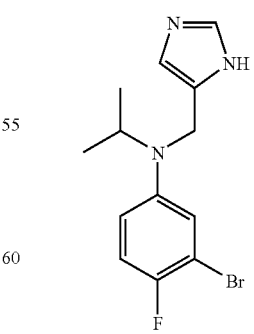

The title compound, MS (ISP): 311.9; 314.0 ((M+H)+.) was obtained analogous to the procedure described for Example 67 using 3-bromo-4-fluoroaniline instead of 4-trifluoromethoxyaniline in step a).

Example 171

(3H-Imidazol-4-ylmethyl)-isopropyl-(3-pyrimidin-5-yl-phenyl)-amine

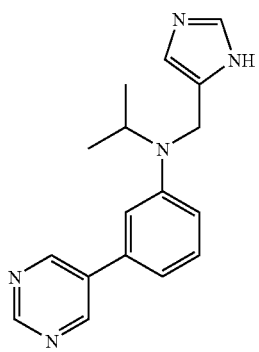 [SMILES: CC(C)N(Cc1cnc[nH]1)c1cccc(-c2cncnc2)c1]

The title compound, MS (ISP): 294.2 ((M+H)+.) was obtained analogous to the procedure described for Example 67 using 3-pyrimidin-5-yl-phenyl-amine instead of 4-trifluoromethoxyaniline in step a).

Example 172

(4-Benzyl-phenyl)-(1H-imidazol-4-ylmethyl)-isopropyl-amine

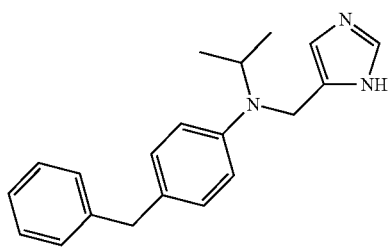 [SMILES: CC(C)N(Cc1cnc[nH]1)c1ccc(Cc2ccccc2)cc1]

The title compound, MS (ISP): 306.5 ((M+H)+.) was obtained in comparable yield analogous to the procedure described for Example 67 using 4-benzylaniline instead of 4-trifluoromethoxyaniline in step a).

Example 173

(4-Benzyl-phenyl)-ethyl-(1H-imidazol-4-ylmethyl)-amine

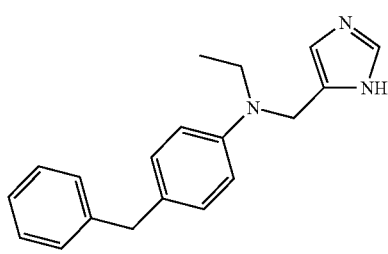 [SMILES: CCN(Cc1cnc[nH]1)c1ccc(Cc2ccccc2)cc1]

The title compound, MS (ISP): 292.3 ((M+H)+.) was obtained in comparable yield analogous to the procedure described for Example 81 using 4-benzylaniline instead of 3-chloro-2-fluoroaniline in step a).

Example 174

(3H-Imidazol-4-ylmethyl)-(3-phenoxy-phenyl)-amine

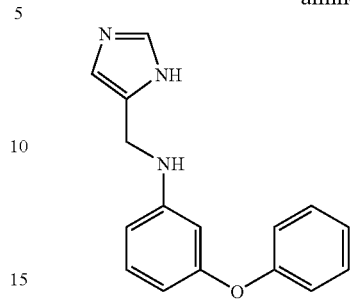

The title compound, MS (ISP): 266.1 ((M+H)+.) was obtained in comparable yield analogous to the procedure described for Example 63 using 3-phenoxy-aniline instead of 2-methoxyaniline.

Example 175

(3H-Imidazol-4-ylmethyl)-methyl-(3-phenoxy-phenyl)-amine

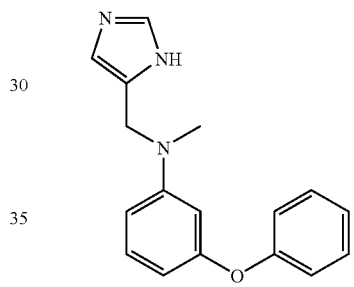

The title compound, MS (ISP): 280.5 ((M+H)+.) was obtained analogous to the procedure described for Example 81 using 3-phenoxyaniline instead of 3-chloro-2-fluoroaniline in step a) and formaldehyde instead of acetaldehyde in step b).

Example 176

(3-Benzyloxy-phenyl)-(3H-imidazol-4-ylmethyl)-amine

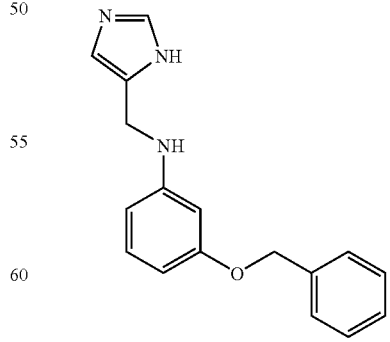

The title compound, MS (ISP): 280.3 ((M+H)+.) was obtained in comparable yield analogous to the procedure described for Example 63 using 3-benzyloxy-aniline instead of 2-methoxyaniline.

Example 177

(3H-Imidazol-4-ylmethyl)-(3-methoxy-phenyl)-amine

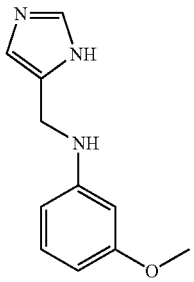

The title compound, MS (ISP): 204.1 ((M+H)+.) was obtained in comparable yield analogous to the procedure described for Example 63 using 3-methoxy-aniline instead of 2-methoxyaniline.

Example 178

[3-Chloro-4-(pyridin-4-yloxy)-phenyl]-(1H-imidazol-4-ylmethyl)-isopropyl-amine

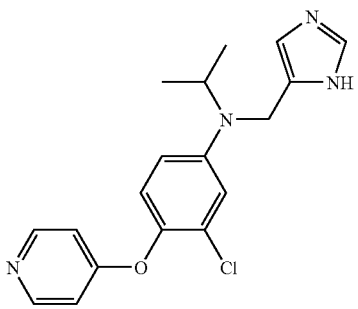 [SMILES: CC(C)N(Cc1cnc[nH]1)c1ccc(Oc2ccncc2)c(Cl)c1]

The title compound, MS (ISP): 343.0 ((M+H)+.) was obtained in comparable yield analogous to the procedure described for Example 67 using 3-chloro-4-(pyridin-4-yloxy)-phenylamine instead of 4-trifluoromethoxyaniline in step a).

Example 179

(3-Chloro-5-fluoro-phenyl)-(1H-imidazol-4-ylmethyl)-amine

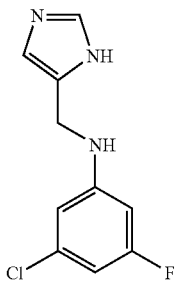 [SMILES: Fc1cc(Cl)cc(NCc2cnc[nH]2)c1]

The title compound, MS (ISP): 228.1 ([37Cl M+H]+.), 226.1 ([35Cl M+H]+.), was obtained in comparable yield analogous to the procedure described for Example 63 using 3-chloro-5-fluoro-aniline instead of 2-methoxyaniline.

Example 180

(3,4-Difluoro-phenyl)-(1H-imidazol-4-ylmethyl)-amine

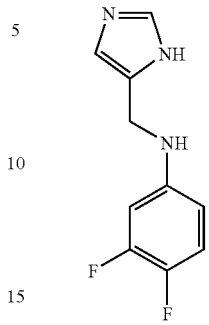

To a solution of 3,4-difluoroaniline (0.60 g, 4.65 mmol) in 1,2-dichloroethane (5 ml) were added 4-formylimidazole (0.67 g, 6.97 mmol), sodium triacetoxyborohydride (1.97 g, 9.29 mmol) and acetic acid (0.05 ml). The reaction mixture was stirred at 50° C. for 4 h. The reaction mixture was then concentrated in vacuo and the residue was purified using flash chromatography (column: Isolute® Flash-NH$_2$ (Separtis); eluent: methanol/dichloromethane gradient) to yield an off-white solid (284 mg, 29%); MS (ISP): 210.1 ((M+H)+.).

Example 181

(4-Bromo-3-fluoro-phenyl)-(1H-imidazol-4-ylmethyl)-amine

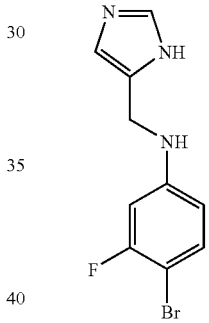

The title compound, MS (ISP): 272.1 ([81Br M+H]+), 270.1 ([79Br M+H]+), was obtained in comparable yield analogous to the procedure described for Example 180 using 4-bromo-3-fluoro-aniline instead of 3,4-difluoro-aniline.

Example 182

{3-[Ethyl-(3H-imidazol-4-ylmethyl)-amino]-2,6-difluoro-phenyl}-methanol

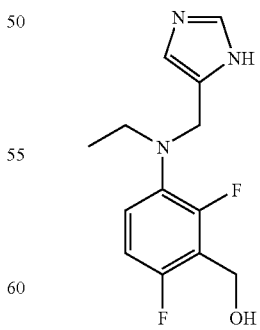

a) 5-[(3-[1,3]-Dioxolan-2-yl-2,4-difluoro-phenylamino)-methyl]-imidazole-1-sulfonic acid dimethylamide To a stirred solution of 3-[1,3]dioxolan-2-yl-2,4-difluoro-phenylamine (0.41 g, 1.94 mmol) in methanol (10 ml) was added 4-formyl-imidazole-1-sulfonic acid dimethylamide (0.46 g, 2.24 mmol) and the mixture was heated at 60° C. for 18 h. After cooling to room temperature sodium borohydride (0.39 g, 10.3 mmol) was added and the mixture stirred at room temperature for 2 h. The mixture was concentrated in vacuo and the residue was purified by flash chromatography (column: Isolute® Flash-NH$_2$ (Separtis); eluent: ethyl acetate/cyclohexane gradient) to yield a light brown gum (604 mg, 76%); MS (ISP): 389.1 ((M+H)$^+$.).

b) 5-[(3-[1,3]-Dioxolan-2-yl-2,4-difluoro-phenylamino)-methyl]-imidazole-1-sulfonic acid dimethylamide To a stirred solution of 5-[(3-[1,3]dioxolan-2-yl-2,4-difluoro-phenylamino)-methyl]-imidazole-1-sulfonic acid dimethylamide (0.60 g, 1.53 mmol) in methanol (20 ml) were added acetaldehyde (0.43 ml, 7.61 mmol), zinc chloride (6.13 mmol) and sodium cyanoborohydride (0.29 g, 4.60 mmol) and the mixture was heated at 40° C. for 18 h. The mixture was then concentrated in vacuo and the residue taken up in ethyl acetate and washed with saturated aq. ammonium chloride solution. The layers were separated and the aqueous phase was back extracted twice with ethyl acetate. The combined organic phases were washed sequentially with water and with saturated brine, then dried over magnesium sulfate and concentrated in vacuo. The residue was purified by flash chromatography (column: Isolute® Flash-NH$_2$ (Separtis); eluent: ethyl acetate/cyclohexane gradient) to yield a colourless viscous oil (538 mg, 84%); MS (ISP): 417.3 ((M+H)$^+$.).

c) (3-[1,3]Dioxolan-2-yl-2,4-difluoro-phenyl)-ethyl-(3H-imidazol-4-ylmethyl)-amine To a stirred solution of 5-[(3-[1,3]dioxolan-2-yl-2,4-difluoro-phenylamino)-methyl]-imidazole-1-sulfonic acid dimethylamide (0.53 g, 1.27 mmol) in tetrahydrofuran (10 ml) was added a 4 N solution of hydrogen chloride in dioxane (3.87 ml, 15.5 mmol) and the mixture was stirred at room temperature for 24 h. The mixture was then concentrated in vacuo and the residue taken up in dichloromethane/methanol (95:5) and washed with 1 N aq. sodium hydroxide solution. The layers were separated and the aqueous phase was back extracted twice with dichloromethane/methanol (95:5). The combined organic phases were washed with saturated brine, then dried over magnesium sulfate and concentrated in vacuo. The residue was purified by flash chromatography (column: Isolute® Flash-NH$_2$ (Separtis); eluent: methanol/dichloromethane gradient) to yield a colourless gum (225 mg, 57%); MS (ISP): 310.3 ((M+H)$^+$.).

d) 3-[Ethyl-(3H-imidazol-4-ylmethyl)-amino]-2,6-difluoro-benzaldehyde

To a stirred solution of (3-[1,3]dioxolan-2-yl-2,4-difluoro-phenyl)-ethyl-(3H-imidazol-4-ylmethyl)-amine (0.22 g, 0.70 mmol) in tetrahydrofuran (5 ml) was added a 3 N aqueous solution of hydrochloric acid (0.93 ml, 2.79 mmol) and the mixture was stirred at room temperature for 48 h. The mixture was then concentrated in vacuo and the residue taken up in ethyl acetate and washed with 1 N aq. sodium hydroxide solution. The layers were separated and the aqueous phase was back extracted twice with ethyl acetate. The combined organic phases were washed with saturated brine, then dried over magnesium sulfate and concentrated in vacuo. The residue was purified by flash chromatography (column: Isolute® Flash-NH$_2$ (Separtis); eluent: methanol/dichloromethane gradient) to yield a yellow gum (111 mg, 48%); MS (ISP): 266.0 ((M+H)$^+$.).

e) {3-[Ethyl-(3H-imidazol-4-ylmethyl)-amino]-2,6-difluoro-phenyl}-methanol

To a stirred solution of 3-[ethyl-(3H-imidazol-4-ylmethyl)-amino]-2,6-difluoro-benzaldehyde (0.10 g, 0.39 mmol) in methanol (3 ml) was added sodium borohydride (0.06 g, 1.56 mmol) and the mixture was stirred at room temperature for 5 h. The mixture was concentrated in vacuo and the residue was purified by flash chromatography (column: Isolute® Flash-NH$_2$ (Separtis); eluent: methanol/dichloromethane gradient) to yield a colourless gum (604 mg, 76%); MS (ISP): 268.3 ((M+H)$^+$.).

Example 183

(3-Bromo-4-fluoro-phenyl)-(3H-imidazol-4-ylmethyl)-amine

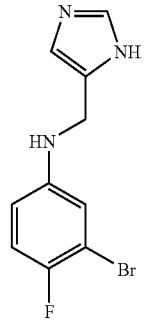 [SMILES: Fc1ccc(NCc2cnc[nH]2)cc1Br]

The title compound, MS (ISP): 272.1 ([$^{81}$Br M+H]$^+$), 270.1 ([$^{79}$Br M+H]$^+$), was obtained in comparable yield analogous to the procedure described for Example 180 using 3-bromo-4-fluoro-aniline instead of 3,4-difluoro-aniline.

Example 184

(3-Difluoromethoxy-phenyl)-(3H-imidazol-4-ylmethyl)-amine

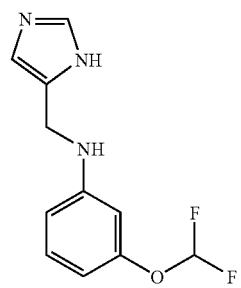 [SMILES: FC(F)Oc1cccc(NCc2cnc[nH]2)c1]

The title compound, MS (ISP): 240.1 ([M+H]$^+$.), was obtained in comparable yield analogous to the procedure described for Example 63 using 3-(difluoromethoxy)-aniline instead of 2-methoxyaniline.

Example 185

(4-Fluoro-3-methoxy-phenyl)-(3H-imidazol-4-ylmethyl)-amine

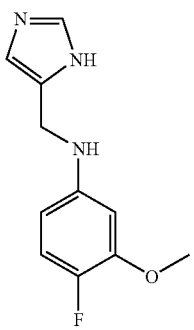 [SMILES: COc1cc(NCc2cnc[nH]2)ccc1F]

The title compound, MS (ISP): 222.1 ([M+H]⁺.), was obtained in comparable yield analogous to the procedure described for Example 63 using 4-fluoro-3-methoxy-aniline instead of 2-methoxyaniline.

Example 186

(3H-Imidazol-4-ylmethyl)-(3-methoxy-phenyl)-methyl-amine

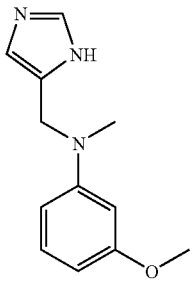 [SMILES: COc1cccc(N(C)Cc2cnc[nH]2)c1]

a) (3H-Imidazol-4-ylmethyl)-(3-methoxy-phenyl)-amine

To a solution of m-anisidine (0.91 ml, 8.12 mmol) in methanol (25 ml) was added 4-formylimidazole (0.86 g, 8.93 mmol). After stirring the mixture overnight at room temperature sodium borohydride (0.46 g, 12.2 mmol) was added. The reaction mixture was then concentrated in vacuo. The residue was purified using flash chromatography (column: Isolute® Flash-NH₂ from Separtis; eluent: methanol/dichloromethane 9:1) to yield a white solid (1.34 g, 18%); MS (ISP): 204.1 ([M+H]⁺).

b) (3H-Imidazol-4-ylmethyl)-(3-methoxy-phenyl)-methyl-amine (3H-Imidazol-4-ylmethyl)-(3-methoxy-phenyl)-amine (0.070 g, 0.34 mmol) was dissolved in acetonitrile (10 ml). Then formaldehyde (0.0.06 ml, 0.86 mmol, 37% aqueous solution) and sodium cyanoborohydride (0.065 g, 1.03 mmol) were added and the reaction mixture was allowed to stir at room temperature for 10 minutes. The reaction mixture was then acidified to pH 2-3 by dropwise addition of concentrated hydrochloric acid whereupon precipitation occurred. The mixture was stirred for a further 1 h at room temperature before being concentrated in vacuo. The residue was taken up in ethyl acetate, washed with 1 M aqueous sodium hydroxide solution and the organic layer was dried over magnesium sulfate and concentrated in vacuo. The residue was purified using flash chromatography (column: Isolute® Flash-NH₂ from Separtis; eluent: methanol/dichloromethane gradient) to yield a white solid (0.056 g, 75%); MS (ISP): 218.3 ([M+H]⁺).

Example 187

(1H-Imidazol-4-ylmethyl)-isopropyl-[4-(2-pyridin-4-yl-ethyl)-phenyl]-amine

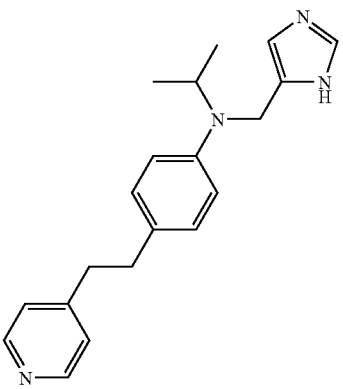 [SMILES: CC(C)N(Cc1cnc[nH]1)c1ccc(CCc2ccncc2)cc1]

The title compound, MS (ISP): 321.1 ((M+H)⁺.) was obtained in comparable yield analogous to the procedure described for Example 67 using 4-(2-pyridin-4-yl-ethyl)-phenylamine instead of 4-trifluoromethoxyaniline in step a).

Example 188

Ethyl-(3H-imidazol-4-ylmethyl)-(3-phenoxy-phenyl)-amine

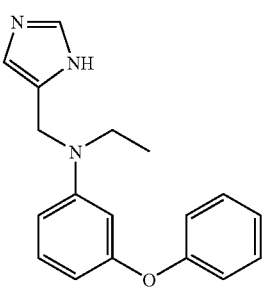 [SMILES: CCN(Cc1cnc[nH]1)c1cccc(Oc2ccccc2)c1]

The title compound, MS (ISP): 294.1 ([M+H]⁺.) was obtained in comparable yield analogous to the procedure described for Example 81 using 3-phenoxyaniline instead of 3-chloro-2-fluoroaniline in step a).

Example 189

(3-Difluoromethoxy-phenyl)-(3H-imidazol-4-ylm-ethyl)-methyl-amine

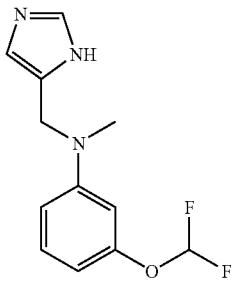 [SMILES: CN(Cc1cnc[nH]1)c1cccc(OC(F)F)c1]

The title compound, MS (ISP): 254.3 ((M+H)⁺.) was obtained analogous to the procedure described for Example 186 using 3-(difluoromethoxy)aniline instead of m-anisidine in step a).

Example 190

(3-Benzyloxy-phenyl)-(3H-imidazol-4-ylmethyl)-methyl-amine

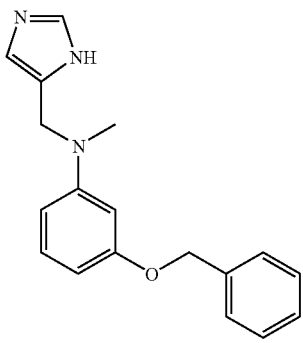 [SMILES: CN(Cc1cnc[nH]1)c1cccc(OCc2ccccc2)c1]

The title compound, MS (ISP): 294.1 ((M+H)⁺.) was obtained analogous to the procedure described for Example 186 using 3-benzyloxyaniline instead of m-anisidine in step a).

Example 191

(4-Fluoro-3-methoxy-phenyl)-(3H-imidazol-4-ylm-ethyl)-methyl-amine

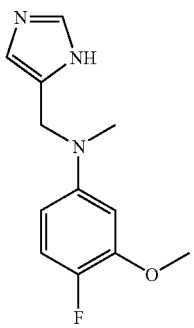 [SMILES: COc1cc(N(C)Cc2cnc[nH]2)ccc1F]

The title compound, MS (ISP): 236.1 ((M+H)⁺.) was obtained analogous to the procedure described for Example 186 using 4-fluoro-3-methoxyaniline instead of m-anisidine in step a).

Example 192

(3-Benzyloxy-phenyl)-ethyl-(3H-imidazol-4-ylm-ethyl)-amine

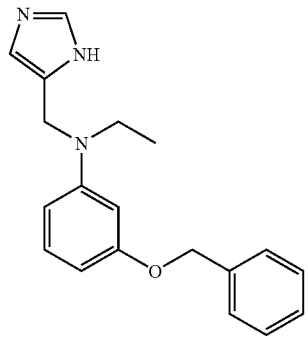 [SMILES: CCN(Cc1cnc[nH]1)c1cccc(OCc2ccccc2)c1]

The title compound, MS (ISP): 308.4 ([M+H]⁺.) was obtained in comparable yield analogous to the procedure described for Example 81 using 3-benzyloxyaniline instead of 3-chloro-2-fluoroaniline in step a).

Example 193

Ethyl-(3H-imidazol-4-ylmethyl)-(3-methoxy-phenyl)-amine

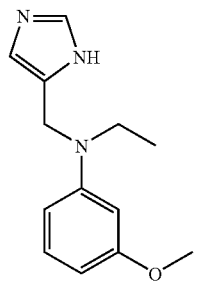 [SMILES: CCN(Cc1cnc[nH]1)c1cccc(OC)c1]

The title compound, MS (ISP): 232.1 ([M+H]⁺.) was obtained in comparable yield analogous to the procedure described for Example 81 using 3-methoxyaniline instead of 3-chloro-2-fluoroaniline in step a).

Example 194

Ethyl-(4-fluoro-3-methoxy-phenyl)-(3H-imidazol-4-ylmethyl)-amine

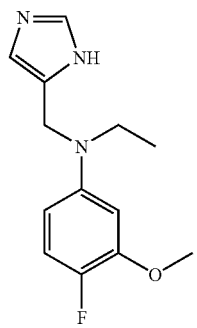 [SMILES: CCN(Cc1cnc[nH]1)c1ccc(F)c(OC)c1]

The title compound, MS (ISP): 250.1 ([M+H]⁺.) was obtained in comparable yield analogous to the procedure described for Example 81 using 4-fluoro-3-methoxyaniline instead of 3-chloro-2-fluoroaniline in step a).

Example 195

(3-Difluoromethoxy-phenyl)-ethyl-(3H-imidazol-4-ylmethyl)-amine

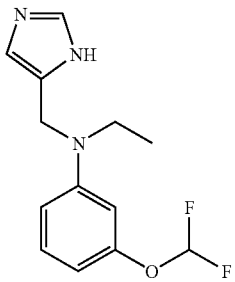 [SMILES: CCN(Cc1cnc[nH]1)c1cccc(OC(F)F)c1]

The title compound, MS (ISP): 268.3 ([M+H]+.) was obtained in comparable yield analogous to the procedure described for Example 81 using 3-(difluoromethoxy)aniline instead of 3-chloro-2-fluoroaniline in step a).

Example 196

(3H-Imidazol-4-ylmethyl)-isopropyl-[3-(1-methyl-piperidin-4-yloxy)-phenyl]-amine

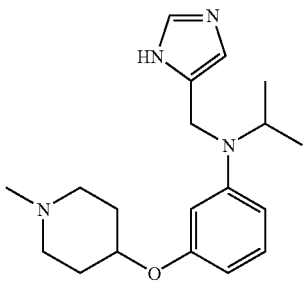 [SMILES: CC(C)N(Cc1cnc[nH]1)c1cccc(OC2CCN(C)CC2)c1]

The title compound, MS (ISP): 459.4 ((M+H)+.) was obtained in comparable yield analogous to the procedure described for Example 67 using 3-[(1-methyl-4-(piperidinyl)oxy)]-phenylamine instead of 4-trifluormethoxyaniline in step a).

Example 197

Ethyl-(1H-imidazol-4-ylmethyl)-[4-(2-pyridin-4-yl-ethyl)-phenyl]-amine

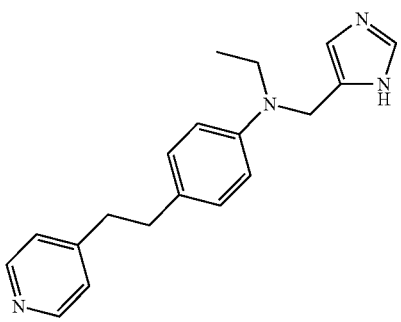 [SMILES: CCN(Cc1cnc[nH]1)c1ccc(CCc2ccncc2)cc1]

The title compound, MS (ISP): 307.3 ((M+H)+.) was obtained in comparable yield analogous to the procedure described for Example 81 using 4-(2-pyridin-4-yl-ethyl)-phenylamine instead of 3-chloro-2-fluoroaniline in step a).

Example 198

(3H-Imidazol-4-ylmethyl)-(3-methoxy-phenyl)-pyridin-4-ylmethyl-amine

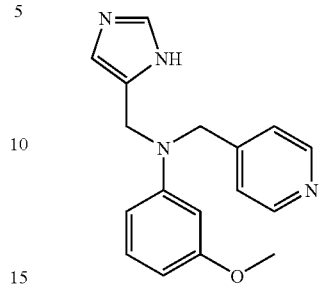

To a solution of (3H-imidazol-4-ylmethyl)-(3-methoxy-phenyl)-amine (0.05 g, 0.25 mmol, Example 186 step a) in 1,2-dichloroethane (2 ml) were added pyridine-4-carbaldehyde (0.06 ml, 0.64 mmol) and sodium triacetoxyborohydride (0.21 g, 0.98 mmol). The reaction mixture was stirred at 40° C. for 72 h. The reaction mixture was then concentrated in vacuo and the residue was purified using flash chromatography (column: Isolute® Flash-NH$_2$ (Separtis); eluent: methanol/dichloromethane gradient) to yield a yellow oil (7 mg, 10%); MS (ISP): 295.3 ((M+H)+.).

Example 199

(4-Chloro-3-methoxy-phenyl)-(1H-imidazol-4-ylmethyl)-amine

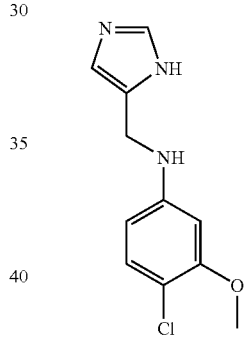

The title compound, MS (ISP): 240.1 ([$^{37}$Cl M+H]+), 238.1 ([$^{35}$Cl M+H]+), was obtained in comparable yield analogous to the procedure described for Example 180 using 4-chloro-3-methoxy-aniline instead of 3,4-difluoro-aniline.

Example 200

[3-(3-Chloro-phenoxy)-phenyl]-(3H-imidazol-4-ylmethyl)-amine

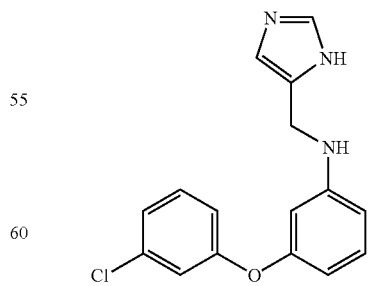

The title compound, MS (ISP): 300.4 ((M+H)+.) was obtained in comparable yield analogous to the procedure described for Example 63 using 3-chloro-phenoxy-aniline instead of 2-methoxyaniline.

Example 201

(3H-Imidazol-4-ylmethyl)-(3-phenoxymethyl-phenyl)-amine

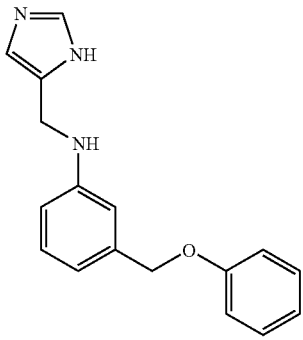

The title compound, MS (ISP): 280.3 ((M+H)+.) was obtained in comparable yield analogous to the procedure described for Example 63 using 3-phenoxymethyl-aniline instead of 2-methoxyaniline.

Example 202

(4-Fluoro-3-phenoxy-phenyl)-(3H-imidazol-4-ylmethyl)-amine

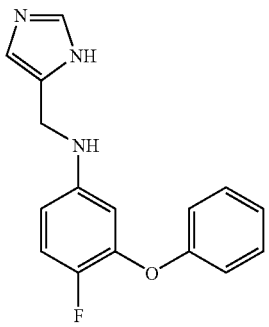 [SMILES: Fc1ccc(NCc2cnc[nH]2)cc1Oc1ccccc1]

The title compound, MS (ISP): 284.1 ((M+H)+.) was obtained in comparable yield analogous to the procedure described for Example 63 using 4-fluoro-3-phenoxy-aniline instead of 2-methoxyaniline.

Example 203

(3H-Imidazol-4-ylmethyl)-(2-methoxy-pyridin-4-yl)-amine

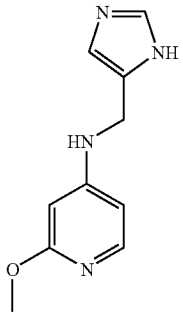

The title compound, MS (ISP): 205.0 ((M+H)+.) was obtained in comparable yield analogous to the procedure described for Example 63 using 4-amino-2-methoxypyridine instead of 2-methoxyaniline.

Example 204

(4-Chloro-3-methoxy-phenyl)-(3H-imidazol-4-ylmethyl)-isopropyl-amine

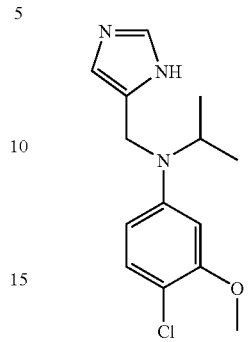

The title compound, MS (ISP): 280.1 ((M+H)+.) was obtained in comparable yield analogous to the procedure described for Example 67 using 4-chloro-3-methoxy-phenylamine instead of 4-trifluormethoxyaniline in step a).

Example 205

(2,2-Dioxo-2,3-dihydro-1H-benzo[c]thiophen-5-yl)-(3H-imidazol-4-ylmethyl)-isopropyl-amine

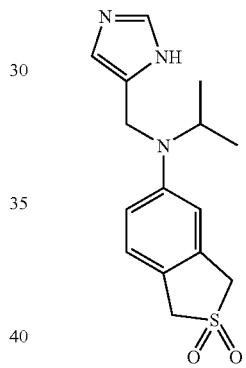

The title compound, MS (ISP): 306.1 ((M+H)+.) was obtained in comparable yield analogous to the procedure described for Example 67 using 5-amino-1,3-dihydrobenzo[c]thiophene 2,2-dioxide instead of 4-trifluormethoxyaniline in step a).

Example 206

[3-(3-Chloro-phenoxy)-phenyl]-(3H-imidazol-4-ylmethyl)-isopropyl-amine

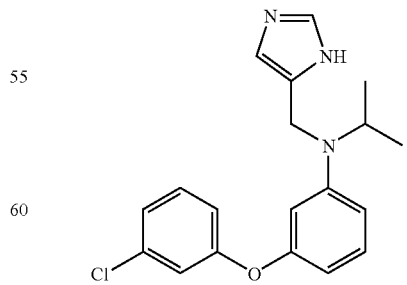

The title compound, MS (ISP): 342.1 ((M+H)+.) was obtained in comparable yield analogous to the procedure described for Example 67 using 3-(3-chloro-phenoxy)-phenylamine instead of 4-trifluormethoxyaniline in step a).

Example 207

(3H-Imidazol-4-ylmethyl)-isopropyl-(3-phenoxymethyl-phenyl)-amine

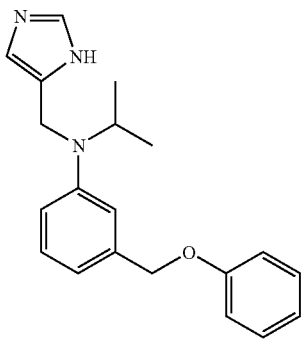 [SMILES: CC(C)N(Cc1cnc[nH]1)c1cccc(COc2ccccc2)c1]

The title compound, MS (ISP): 322.5 ((M+H)$^+$.) was obtained in comparable yield analogous to the procedure described for Example 67 using 3-phenoxymethyl-phenylamine instead of 4-trifluormethoxyaniline in step a).

Example 208

(4-Fluoro-3-phenoxy-phenyl)-(3H-imidazol-4-ylmethyl)-isopropyl-amine

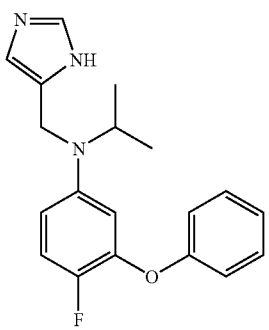 [SMILES: CC(C)N(Cc1cnc[nH]1)c1ccc(F)c(Oc2ccccc2)c1]

The title compound, MS (ISP): 326.3 ((M+H)$^+$.) was obtained in comparable yield analogous to the procedure described for Example 67 using 4-fluoro-3-phenoxy-phenylamine instead of 4-trifluormethoxyaniline in step a).

Example 209

(3-Benzyloxy-phenyl)-(6-bromo-pyridin-2-ylmethyl)-(3H-imidazol-4-ylmethyl)-amine

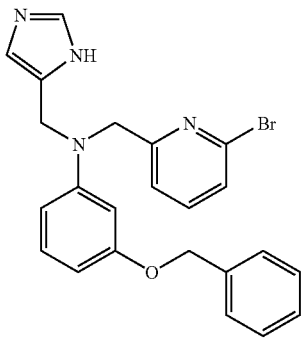 [SMILES: Brc1cccc(CN(Cc2cnc[nH]2)c2cccc(OCc3ccccc3)c2)n1]

a) (3-Benzyloxy-phenyl)-(6-bromo-pyridin-2-ylmethyl)-amine

To a solution of 3-benzyloxyaniline (0.70 g, 3.51 mmol) in 1,2-dichloroethane (10 ml) were added 6-bromo-pyridine-2-carboxaldehyde (0.65 g, 3.51 mmol), sodium triacetoxyborohydride (1.49 g, 7.03 mmol) and acetic acid (0.80 ml, 14.1 mmol). The reaction mixture was shaken at 40° C. overnight. For work-up dichloromethane (100 ml) and 1 M sodium bicarbonate solution (40 ml) were added and the mixture was shaken. The organic layer was separated, dried over magnesium sulfate and evaporated. The residue was purified using flash chromatography (heptane/ethyl acetate=3:1) to yield an orange oil (1.03 g, 80%); MS (ISP): 371.1 ([$^{81}$Br M+H]$^+$), 369.1 ([$^{79}$Br M+H]$^+$).

b) (3-Benzyloxy-phenyl)-(6-bromo-pyridin-2-ylmethyl)-(3H-imidazol-4-ylmethyl)-amine (3-Benzyloxy-phenyl)-(6-bromo-pyridin-2-ylmethyl)-amine (0.10 g, 0.27 mmol) was dissolved in methanol (2 ml). Then 4-formylimidazole (0.13 g, 1.35 mmol), zinc chloride (0.15 g, 1.08 mmol) and sodium cyanoborohydride (0.05 g, 0.81 mmol) were added and the reaction mixture was allowed to stir at 40° C. overnight. After cooling, the reaction mixture was poured onto ammoniumchloride/ice and extracted with ethyl acetate (2 times 50 ml). The organic layer was dried over magnesium sulfate and evaporated. The residue was purified using flash chromatography (SiO$_2$; eluent: methanol/dichloromethane=1:9) to yield an off-white gum (0.11 g, 94%); MS (ISP): 451.1 ([$^{81}$Br M+H]$^+$), 449.1 ([$^{79}$Br M+H]$^+$).

Example 210

Ethyl-(3H-imidazol-4-ylmethyl)-(4-methoxy-pyrimidin-2-yl)-amine

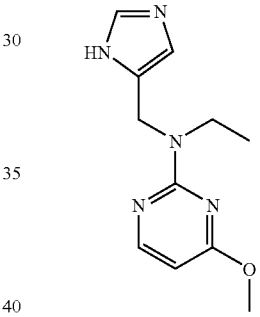

5-Ethylaminomethyl-imidazole-1-sulfonic acid dimethylamide

To a saturated solution of ethylamine in methanol (40 ml) was added 4-formyl-imidazole-1-sulfonic acid dimethylamide (2.5 g, 12.3 mmol) and the mixture was stirred overnight. Sodium borohydride (0.70 g, 18.5 mmol) was added and the mixture was stirred at room temperature for 3 h. Water was added and the solution was extracted three times with ethyl acetate. The combined organic layers were dried over magnesium sulfate and evaporated. The residue was purified by flash chromatography (SiO2: dichloromethane/methanol=9:1) to yield a light yellow oil (0.785 g, 27%); MS (ISP): 233.1 ((M+H)$^+$.).

4{[Ethyl-(4-methoxy-pyrimidin-2-yl)-amino]-methyl}-imidazole-1-sulfonic acid dimethylamide A solution of 5-ethylaminomethyl-imidazole-1-sulfonic acid dimethylamide (0.527 g, 2.25 mmol), 2-chloro-4-methoxy-pyrimidine (0.217 g; 1.5 mmol) and N,N-diisopropyl ethyl amine (0.51 ml, 3.0 mmol) in isopropanol (2 ml) was heated in a sealed vessel in a microwave oven for 20 min at 160° C. Ethyl acetate (20 ml) and silica gel (1 g) was added and the mixture was evaporated. The residue was purified by flash chromatography, column: Isolute® Flash-NH$_2$ (Separtis); eluent: heptane/ethyl acetate=8:2) to yield a white solid, (0.265 g, 52%); MS (ISP): 341.0 ((M+H)$^+$.).

Ethyl-(3H-imidazol-4-ylmethyl)-(4-methoxy-pyrimidin-2-yl)-amine

4-{[Ethyl-(4-methoxy-pyrimidin-2-yl)-amino]-methyl}-imidazole-1-sulfonic acid dimethylamide (0.265 g, 0.78 mmol) was dissolved in aqueous hydrochloric acid (4 N, 2 ml) and the mixture was stirred at 100° C. for 2 hours. After cooling concentrated sodium hydroxide solution was added slowly until basic pH. The mixture was extracted three times with ethyl acetate. The combined organic layers were dried over magnesium sulfate and evaporated. The residue was purified by flash chromatography, column: Isolute® Flash-NH$_2$ (Separtis); eluent: heptane/ethyl acetate=1:1) to yield a colorless liquid, (0.10 g, 55%); MS (ISP): 234.3 ((M+H)$^+$.).

Example 211

(3H-Imidazol-4-ylmethyl)-isopropyl-[3-(1,2,3,4-tetrahydro-naphthalen-1-yloxy)-phenyl]-amine

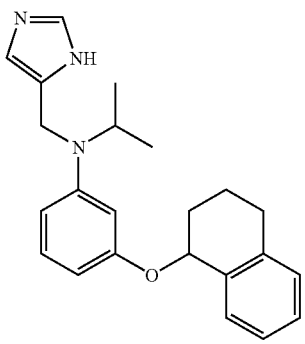 [SMILES: CC(C)N(Cc1cnc[nH]1)c1cccc(OC2CCCc3ccccc32)c1]

The title compound, MS (ISP): 362.4 ((M+H)$^+$.) was obtained in comparable yield analogous to the procedure described for Example 67 using 3-(1,2,3,4-tetrahydro-naphthalen-1-yloxy)-phenylamine (synthesized in analogy to its 2-chloro derivative as published in WO2007046392) instead of 4-trifluormethoxyaniline in step a).

Example 212

Ethyl-(3H-imidazol-4-ylmethyl)-(4-phenoxy-pyrimidin-2-yl)-amine

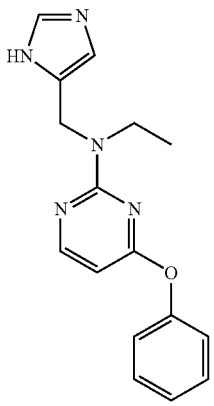 [SMILES: CCN(Cc1cnc[nH]1)c1nccc(Oc2ccccc2)n1]

The title compound, MS (ISP): 296.3 ((M+H)$^+$.) was obtained in comparable yield analogous to the procedure described for Example 210 using 2-chloro-4-phenoxy-pyrimidine instead of 2-chloro-4-methoxy-pyrimidine in step b).

Example 213

(3-Benzyloxy-phenyl)-(2-methyl-1H-imidazol-4-ylmethyl)-amine

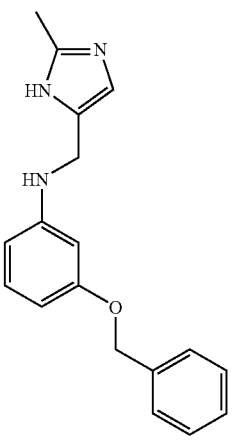 [SMILES: Cc1ncc(CNc2cccc(OCc3ccccc3)c2)[nH]1]

The title compound, MS (ISP): 294.0 ((M+H)$^+$.) was obtained in comparable yield analogous to the procedure described for Example 63 using 4-formyl-2-methylimidazole instead of 4-formyl-imidazole and 3-benzyloxyaniline instead of 2-methoxyaniline.

Example 214

(2-Benzyl-6-chloro-pyrimidin-4-yl)-ethyl-(3H-imidazol-4-ylmethyl)-amine

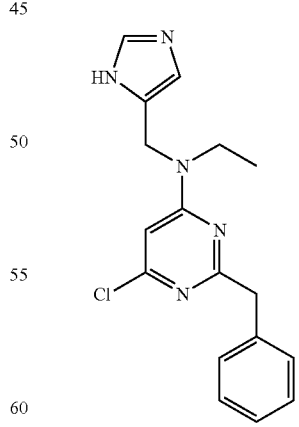

The title compound, MS (ISP): 328.3 ((M+H)$^+$.) was obtained in comparable yield analogous to the procedure described for Example 210 using 2-benzyl-4,6-dichloro-pyrimidine instead of 2-chloro-4-methoxy-pyrimidine in step b).

Example 215

(2-Benzyl-pyrimidin-4-yl)-ethyl-(3H-imidazol-4-ylmethyl)-amine

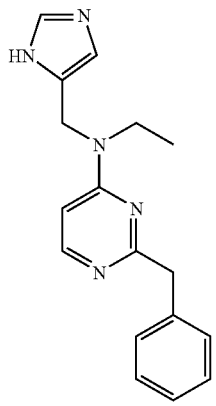 [SMILES: CCN(Cc1cnc[nH]1)c1ccnc(Cc2ccccc2)n1]

(2-Benzyl-6-chloro-pyrimidin-4-yl)-ethyl-(3H-imidazol-4-ylmethyl)-amine (0.164 g, 0.5 mmol) was dissolved in methanol (3 ml), ammonium formate (0.315 g, 0.5 mmol) and palladium on charcoal (0.164 g, 10% Pd) was added and the mixture was refluxed for one hour. After cooling the catalyst was filtered off and the solvent was evaporated. The residue was purified by flash chromatography (column: Isolute® Flash-NH$_2$ from Separtis; eluent: ethyl acetate/methanol=95:5) to yield a white solid, (0.03 g, 21%); MS (ISP): 294.4 ((M+H)$^+$.).

Example 216

Ethyl-(3H-imidazol-4-ylmethyl)-(6-phenoxy-pyrimidin-4-yl)-amine

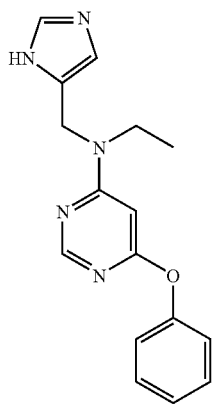 [SMILES: CCN(Cc1cnc[nH]1)c1cc(Oc2ccccc2)ncn1]

The title compound, MS (ISP): 296.3 ((M+H)$^+$.) was obtained in comparable yield analogous to the procedure described for Example 210 using 2-chloro-6-phenoxy-pyrimidine instead of 2-chloro-4-methoxy-pyrimidine in step b).

Example 217

(4-Chloro-pyrimidin-2-yl)-ethyl-(3H-imidazol-4-ylmethyl)-amine

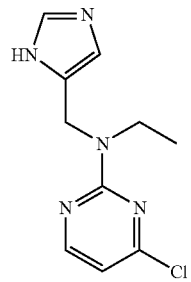 [SMILES: CCN(Cc1cnc[nH]1)c1nccc(Cl)n1]

The title compound, MS (ISP): 238.0 ((M+H)$^+$.) was obtained in comparable yield analogous to the procedure described for Example 210 using 2,4-dichloro-pyrimidine instead of 2-chloro-4-methoxy-pyrimidine in step b) and chromatographic separation from the 2-chloro-pyrimidin-4-yl isomer before step c).

Example 218

(2-Chloro-pyrimidin-4-yl)-ethyl-(3H-imidazol-4-ylmethyl)-amine

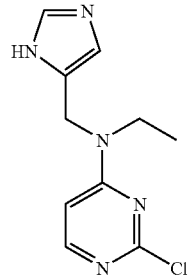 [SMILES: CCN(Cc1cnc[nH]1)c1ccnc(Cl)n1]

The title compound, MS (ISP): 238.1 ((M+H)$^+$.) was obtained in comparable yield analogous to the procedure described for Example 210 using 2,4-dichloro-pyrimidine instead of 2-chloro-4-methoxy-pyrimidine in step b) and chromatographic separation from the 4-chloro-pyrimidin-2-yl isomer before step c).

Example 219

(4,6-Dichloro-pyrimidin-2-yl)-(1H-imidazol-4-ylmethyl)-amine

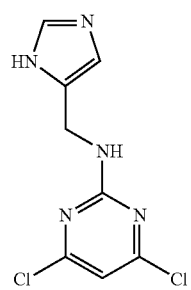 [SMILES: Clc1cc(Cl)nc(NCc2cnc[nH]2)n1]

To a solution of 2-amino-4,6-dichloropyrimidine (1.00 g, 7.72 mmol) in dichloromethane (8 ml) were added 4-formylimidazole (0.74 g, 7.72 mmol) and tetraisopropyl orthotitanate (2.86 ml, 9.65 mmol). After stirring the mixture at 40° C. overnight ethanol (8 ml) and sodium borohydride (0.38 g, 10.0 mmol) were added. The reaction mixture was stirred 40° C. for 7 hours. Then mixture was concentrated in vacuo and the residue was purified by flash chromatography (methanol/dichloromethane gradient) to yield white crystals (43 mg, 26%); MS (EI): 247.1 ($^{37}$Cl M$^+$.), 245.1 ($^{37}$Cl$^{35}$Cl M$^+$.), 243.1 ($^{35}$Cl M$^+$.).

Example 220

(1H-Imidazol-4-ylmethyl)-(4-methyl-pyrimidin-2-yl)-amine

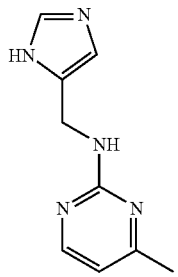

The title compound, MS (ISP): 190.4 ([M+H]$^+$), was obtained in comparable yield analogous to the procedure described for Example 219 using 2-amino-4-methylpyrimidine instead of 2-amino-4,6-dichloropyrimidine.

Example 221

(4-Cyclopropyl-phenyl)-(1H-imidazol-4-ylmethyl)-amine

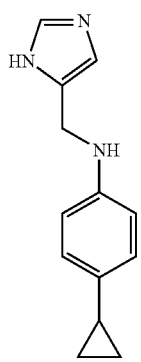 [SMILES: c1ncc(CNc2ccc(C3CC3)cc2)[nH]1]

The title compound, MS (ISP): 214.1 ([M+H]$^+$), was obtained in comparable yield analogous to the procedure described for Example 180 using 4-cyclopropyl-aniline instead of 3,4-difluoro-aniline.

Example 222

(3-Cyclopropyl-phenyl)-(1H-imidazol-4-ylmethyl)-amine

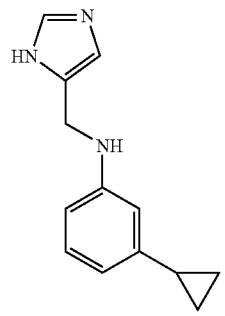 [SMILES: c1cc(NCc2cnc[nH]2)cc(C2CC2)c1]

The title compound, MS (ISP): 214.1 ([M+H]$^+$), was obtained in comparable yield analogous to the procedure described for Example 180 using 3-cyclopropyl-aniline instead of 3,4-difluoro-aniline.

Example 223

(4-Cyclopropyl-phenyl)-(1H-imidazol-4-ylmethyl)-isopropyl-amine

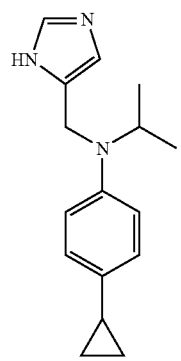 [SMILES: CC(C)N(Cc1cnc[nH]1)c1ccc(C2CC2)cc1]

The title compound, MS (ISP): 256.3 ([M+H]$^+$.) was obtained analogous to the procedure described for Example 67 step b) using (4-cyclopropyl-phenyl)-(1H-imidazol-4-yl-methyl)-amine (Example 221) instead of (3H-imidazol-4-ylmethyl)-(4-trifluoromethoxy-phenyl)-amine.

Example 224

(3-Cyclopropyl-phenyl)-(1H-imidazol-4-ylmethyl)-isopropyl-amine

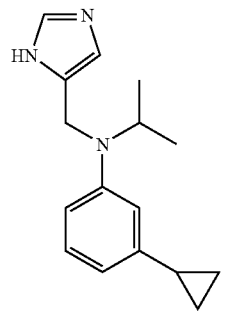 [SMILES: CC(C)N(Cc1cnc[nH]1)c1cccc(C2CC2)c1]

The title compound, MS (ISP): 256.3 ([M+H]+.) was obtained analogous to the procedure described for Example 67 step b) using (3-cyclopropyl-phenyl)-(1H-imidazol-4-yl-methyl)-amine (Example 222) instead of (3H-imidazol-4-ylmethyl)-(4-trifluoromethoxy-phenyl)-amine.

Example 225

(3-Bromo-phenyl)-(3H-imidazol-4-ylmethyl)-amine

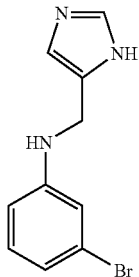

The title compound, MS (ISP): 252.2, 254.1 ((M+H)+.) was obtained in comparable yield analogous to the procedure described for Example 63 using 3-bromoaniline instead of 2-methoxyaniline.

Example 226

(3-Bromo-5-trifluoromethyl-phenyl)-(3H-imidazol-4-ylmethyl)-amine

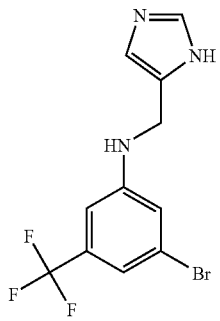 [SMILES: FC(F)(F)c1cc(Br)cc(NCc2cnc[nH]2)c1]

The title compound, MS (ISP): 320.1; 322.2 ((M+H)+.) was obtained in comparable yield analogous to the procedure described for Example 63 using 3-bromo-5-trifluoromethyl-aniline instead of 2-methoxyaniline.

Example 227

3-[(3H-Imidazol-4-ylmethyl)-amino]-benzonitrile

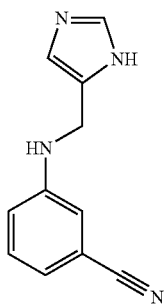 [SMILES: N#Cc1cccc(NCc2cnc[nH]2)c1]

The title compound, MS (ISP): 199.3 ((M+H)+.) was obtained in comparable yield analogous to the procedure described for Example 63 using 3-amino-benzonitrile instead of 2-methoxyaniline.

Example 228

(3H-Imidazol-4-ylmethyl)-(3-isopropyl-phenyl)-amine

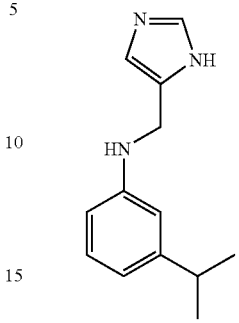

The title compound, MS (ISP): 216.3 ((M+H)+.) was obtained in comparable yield analogous to the procedure described for Example 63 using 3-isopropylaniline instead of 2-methoxyaniline.

Example 229

Ethyl-(1H-imidazol-4-ylmethyl)-(2-phenoxy-pyrimidin-4-yl)-amine

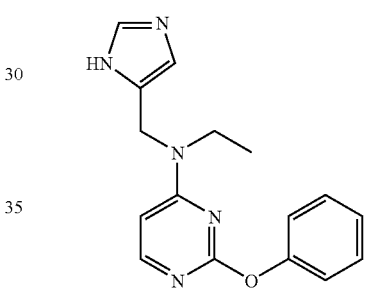

4-{[(2-Chloro-pyrimidin-4-yl)-ethyl-amino]-methyl}-imidazole-1-sulfonic acid dimethylamide The title compound, MS (ISP): 345.1 ((M+H)+.) was obtained in comparable yield analogous to the procedure described for Example 210 using 2,4-dichloro-pyrimidine instead of 2-chloro-4-methoxy-pyrimidine in step b) and chromatographic separation from the 4-chloro-pyrimidin-2-yl isomer without performing step c) at the end.

4-{[Ethyl-(2-phenoxy-pyrimidin-4-yl)-amino]-methyl}-imidazole-1-sulfonic acid dimethylamide To sodium hydride (0.194 g, 55% in mineral oil, 4.4 mmol) in dimethylformamide (1.5 ml) was added phenol (0.418 g, 4.4 mmol) and stirring was continued for 15 min at room temperature. To this reaction mixture 4-{[(2-chloro-pyrimidin-4-yl)-ethyl-amino]-methyl}-imidazole-1-sulfonic acid dimethylamide (0.153 g, 0.44 mmol) was added. After stirring and heating to 80° C. overnight the solvent was evaporated. Water was added (5 ml) and the mixture was extracted with ethyl acetate (20 ml) twice. The combined organic layers were washed with water, dried over magnesium sulphate and evaporated. The residue was purified using flash chromatography (SiO2; eluent: heptane/ethyl acetate=95:5) to yield the title compound as a colourless gum, MS (ISP): 403.4 ((M+H)+.).

Ethyl-(1H-imidazol-4-ylmethyl)-(2-phenoxy-pyrimidin-4-yl)-amine

To remove the dimethylaminosulfonyl protecting group 4-{[ethyl-(2-phenoxy-pyrimidin-4-yl)-amino]-methyl}-imidazole-1-sulfonic acid dimethylamide (65 mg, 0.16 mmol) was dissolved in hydrochloric acid in ethanol (5 N, 1 ml) and the mixture was stirred at 100° C. for 2 hours. For workup aqueous sodium hydroxide solution (0.5 ml, 1 N) was added to basic pH and the mixture was extracted three times with dichloromethane. The combined organic layers were dried over magnesium sulfate and evaporated. The residue was purified by flash chromatography (SiO$_2$; ethyl acetate/methanol=95:5) to yield a white solid, (0.022 g, 46%); MS (ISP): 296.3 ((M+H)$^+$.).

Example 230

(2-Chloro-5-fluoro-pyrimidin-4-yl)-ethyl-(1H-imidazol-4-ylmethyl)-amine

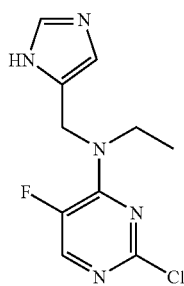

The title compound, MS (ISP): 256.3 ((M+H)$^+$.) was obtained in comparable yield analogous to the procedure described for Example 210 using 2,4-dichloro-5-fluoro-pyrimidine instead of 2-chloro-4-methoxy-pyrimidine in step b).

Example 231

Ethyl-(1H-imidazol-4-ylmethyl)-pyrimidin-2-yl-amine

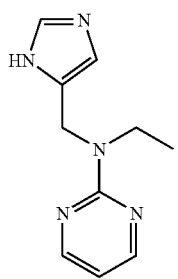

The title compound, MS (ISP): 204.1 ((M+H)$^+$.) was obtained in comparable yield analogous to the procedure described for Example 210 using 2-chloro-pyrimidine instead of 2-chloro-4-methoxy-pyrimidine in step b).

Example 232

(6-Chloro-pyrimidin-4-yl)-ethyl-(1H-imidazol-4-ylmethyl)-amine

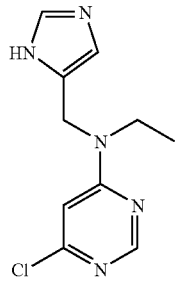 [SMILES: CCN(Cc1cnc[nH]1)c1cc(Cl)ncn1]

The title compound, MS (ISP): 238.0 ((M+H)$^+$.) was obtained in comparable yield analogous to the procedure described for Example 210 using 4,6-dichloro-pyrimidine instead of 2-chloro-4-methoxy-pyrimidine in step b).

Example 233

(6-Chloro-2-methyl-pyrimidin-4-yl)-ethyl-(1H-imidazol-4-ylmethyl)-amine

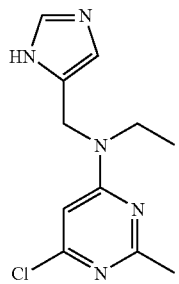 [SMILES: CCN(Cc1cnc[nH]1)c1cc(Cl)nc(C)n1]

The title compound, MS (ISP): 252.1 ((M+H)$^+$.) was obtained in comparable yield analogous to the procedure described for Example 210 using 4,6-dichloro-2-methyl-pyrimidine instead of 2-chloro-4-methoxy-pyrimidine in step b).

Example 234

Ethyl-(1H-imidazol-4-ylmethyl)-(4-trifluoromethyl-pyrimidin-2-yl)-amine

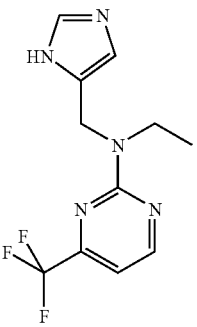 [SMILES: CCN(Cc1cnc[nH]1)c1nccc(C(F)(F)F)n1]

The title compound, MS (ISP): 272.3 ((M+H)$^+$.) was obtained in comparable yield analogous to the procedure described for Example 210 using 2-chloro-4-(trifluoromethyl)-pyrimidine instead of 2-chloro-4-methoxy-pyrimidine in step b).

Example 235

Ethyl-(1H-imidazol-4-ylmethyl)-pyrimidin-4-yl-amine

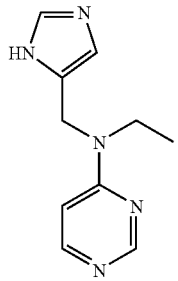

The title compound, MS (ISP): 204.2 ((M+H)+.) was obtained in comparable yield analogous to the procedure described for Example 215 using (6-chloro-pyrimidin-4-yl)-ethyl-(1H-imidazol-4-ylmethyl)-amine instead of (2-benzyl-6-chloro-pyrimidin-4-yl)-ethyl-(3H-imidazol-4-ylmethyl)-amine.

Example 236

Ethyl-(1H-imidazol-4-ylmethyl)-(2-methyl-pyrimidin-4-yl)-amine

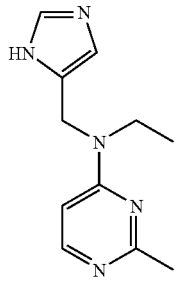

The title compound, MS (ISP): 218.4 ((M+H)+.) was obtained in comparable yield analogous to the procedure described for Example 215 using (6-chloro-2-methyl-pyrimidin-4-yl)-ethyl-(1H-imidazol-4-ylmethyl)-amine instead of (2-benzyl-6-chloro-pyrimidin-4-yl)-ethyl-(3H-imidazol-4-ylmethyl)-amine.

Example 237

(4,6-Dichloro-pyrimidin-2-yl)-ethyl-(1H-imidazol-4-ylmethyl)-amine

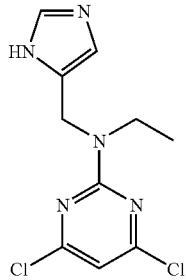 [SMILES: CCN(Cc1cnc[nH]1)c1nc(Cl)cc(Cl)n1]

The title compound, MS (ISP): 272.5 ((M+H)+.) was obtained in comparable yield analogous to the procedure described for Example 210 using 2,4,6-trichloro-pyrimidine instead of 2-chloro-4-methoxy-pyrimidine in step b) and chromatographic separation from the 2,6-dichloro-pyrimidin-2-yl isomer before step c).

Example 238

(2,6-Dichloro-pyrimidin-4-yl)-ethyl-(1H-imidazol-4-ylmethyl)-amine

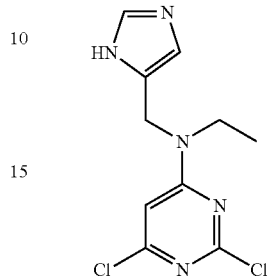

The title compound, MS (ISP): 272.8 ((M+H)+.) was obtained in comparable yield analogous to the procedure described for Example 210 using 2,4,6-trichloro-pyrimidine instead of 2-chloro-4-methoxy-pyrimidine in step b) and chromatographic separation from the 4,6-dichloro-pyrimidin-2-yl isomer before step c).

Example 239

(1H-Imidazol-4-ylmethyl)-isopropyl-(4-methoxy-pyrimidin-2-yl)-amine

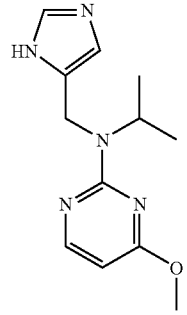

The title compound, MS (ISP): 248.1 ((M+H)+.) was obtained in comparable yield analogous to the procedure described for Example 210 using isopropylamine instead of ethylamine in step a).

Example 240

(6-Bromo-pyridin-2-yl)-(3H-imidazol-4-ylmethyl)-amine

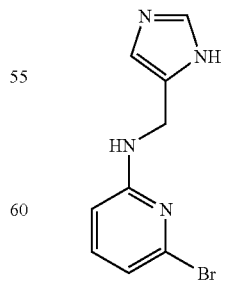

The title compound, MS (ISP): 253.0; 255.0 ((M+H)+.) was obtained in comparable yield analogous to the procedure described for Example 63 using 2-amino-6-bromopyridine instead of 2-methoxyaniline.

Example 241

(3H-Imidazol-4-ylmethyl)-(4-methyl-pyridin-2-yl)-amine

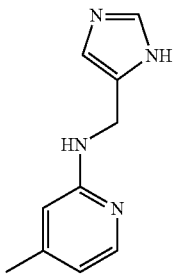

The title compound, MS (ISP): 189.4 ((M+H)+.) was obtained in comparable yield analogous to the procedure described for Example 63 using 2-amino-4-methylpyridine instead of 2-methoxyaniline.

Example 242

(3-Bromo-phenyl)-(3H-imidazol-4-ylmethyl)-isopropyl-amine

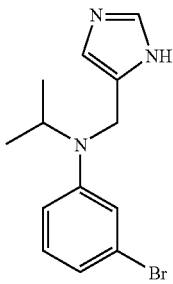 [SMILES: CC(C)N(Cc1cnc[nH]1)c1cccc(Br)c1]

The title compound, MS (ISP): 294.1; 296.2 ((M+H)+.) was obtained in comparable yield analogous to the procedure described for Example 67 using 3-bromoaniline instead of 4-trifluormethoxyaniline in step a).

Example 243

(3-Bromo-5-trifluoromethyl-phenyl)-(3H-imidazol-4-ylmethyl)-isopropyl-amine

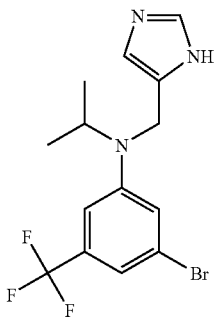 [SMILES: CC(C)N(Cc1cnc[nH]1)c1cc(Br)cc(C(F)(F)F)c1]

The title compound, MS (ISP): 362.1; 364.1 ((M+H)+.) was obtained in comparable yield analogous to the procedure described for Example 67 using 3-bromo-5-trifluoromethyl-aniline instead of 4-trifluormethoxyaniline in step a).

Example 244

(6-Bromo-pyridin-2-yl)-(3H-imidazol-4-ylmethyl)-isopropyl-amine

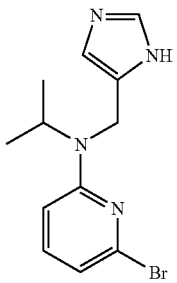

The title compound, MS (ISP): 295.1; 297.2 ((M+H)+.) was obtained in comparable yield analogous to the procedure described for Example 67 using 2-amino-6-bromopyridine instead of 4-trifluormethoxyaniline in step a).

Example 245

(3H-Imidazol-4-ylmethyl)-isopropyl-(3-isopropyl-phenyl)-amine

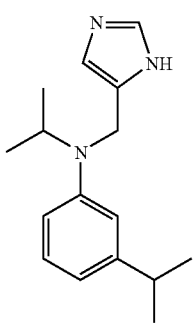 [SMILES: CC(C)c1cccc(N(Cc2cnc[nH]2)C(C)C)c1]

The title compound, MS (ISP): 258.1 ((M+H)+.) was obtained in comparable yield analogous to the procedure described for Example 67 using 3-isopropylaniline instead of 4-trifluormethoxyaniline in step a).

Example 246

(3H-Imidazol-4-ylmethyl)-isopropyl-(4-methyl-pyridin-2-yl)-amine

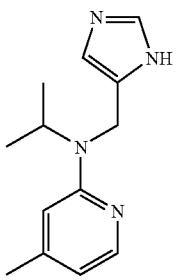 [SMILES: Cc1ccnc(N(Cc2cnc[nH]2)C(C)C)c1]

The title compound, MS (ISP): 231.4 ((M+H)+.) was obtained in comparable yield analogous to the procedure described for Example 67 using 2-amino-4-methylpyridine instead of 4-trifluormethoxyaniline in step a).

Example 247

(3,4-Dichloro-phenyl)-ethyl-(1H-imidazol-4-ylmethyl)-amine

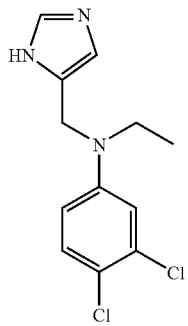 [SMILES: CCN(Cc1cnc[nH]1)c1ccc(Cl)c(Cl)c1]

The title compound, MS (ISP): 274.1 ([$^{37}$Cl M+H]$^+$.), 272.1 ([$^{37}$Cl$^{35}$Cl M+H]$^+$.), 270.2 ([$^{35}$Cl M+H]$^+$.), was obtained in comparable yield analogous to the procedure described for Example 81 using 3,4-dichloroaniline instead of 3-chloro-2-fluoroaniline in step a).

Example 248

(4-Chloro-3-methoxy-phenyl)-(1H-imidazol-4-ylmethyl)-methyl-amine

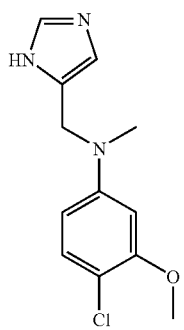

The title compound, MS (ISP): 254.1 ([$^{37}$Cl M+H]$^+$.), 252.1 ([$^{35}$Cl M+H]$^+$.), was obtained analogous to the procedure described for Example 186 using 4-chloro-3-methoxyaniline instead of m-anisidine in step a).

Example 249

Ethyl-(5-fluoro-2-methoxy-pyrimidin-4-yl)-(1H-imidazol-4-ylmethyl)-amine

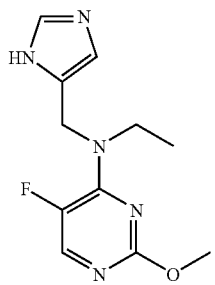 [SMILES: CCN(Cc1cnc[nH]1)c1nc(OC)ncc1F]

The title compound, MS (ISP): 252.1 ((M+H)$^+$.) was obtained in comparable yield analogous to the procedure described for Example 229 using 2,4-dichloro-5-fluoro-pyrimidine instead of 2,4-dichloro-pyrimidine in step a) and sodium methoxide in 1,2-dimethoxyethane instead of sodium hydride/phenol in dimethylformamide in step b).

Example 250

(1H-Imidazol-4-ylmethyl)-isopropyl-(2-methoxy-pyrimidin-4-yl)-amine

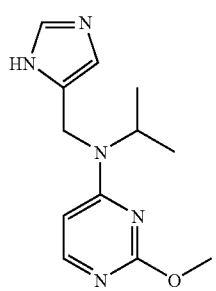 [SMILES: COc1nccc(N(Cc2cnc[nH]2)C(C)C)n1]

The title compound, MS (ISP): 247.9 ((M+H)$^+$.) was obtained in comparable yield analogous to the procedure described for Example 229 using sodium methoxide in 1,2-dimethoxyethane instead of sodium hydride/phenol in dimethylformamide in step b).

Example 251

Ethyl-(1H-imidazol-4-ylmethyl)-(6-trifluoromethyl-pyridin-2-yl)-amine

The title compound, MS (ISP): 271.1 ((M+H)$^+$.) was obtained in comparable yield analogous to the procedure described for Example 210 using 2-bromo-6-(trifluoromethyl)-pyridine instead of 2-chloro-4-methoxy-pyrimidine in step b).

Example 252

(1H-Imidazol-4-ylmethyl)-(3-morpholin-4-yl-phenyl)-amine

The title compound, MS (ISP): 259.3 ([M+H]$^+$.), was obtained in comparable yield analogous to the procedure described for Example 63 using 3-morpholin-4-yl-phenylamine instead of 2-methoxyaniline.

Example 253

3-[(3H-Imidazol-4-ylmethyl)-isopropyl-amino]-benzonitrile

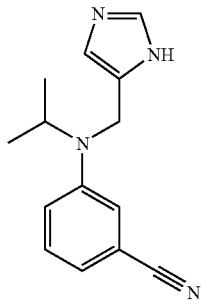 [SMILES: CC(C)N(Cc1cnc[nH]1)c1cccc(C#N)c1]

The title compound, MS (ISP): 241.2 ((M+H)+.) was obtained in comparable yield analogous to the procedure described for Example 67 using 3-aminobenzonitrile instead of 4-trifluormethoxyaniline in step a).

Example 254

(4,6-Dimethyl-pyrimidin-2-yl)-(1H-imidazol-4-ylmethyl)-isopropyl-amine

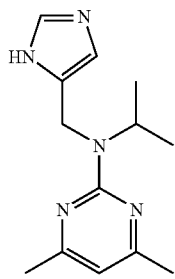

The title compound, MS (ISP): 246.4 ((M+H)+.) was obtained in comparable yield analogous to the procedure described for Example 210 using isopropylamine instead of ethylamine in step a) and 4,6-dimethyl-2-chloro-pyrimidine instead of 2-chloro-4-methoxy-pyrimidine in step b).

Example 255

(4-Chloro-6,7-dihydro-5H-cyclopentapyrimidin-2-yl)-(1H-imidazol-4-ylmethyl)-isopropyl-amine

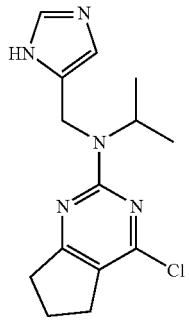 [SMILES: CC(C)N(Cc1cnc[nH]1)c1nc(Cl)c2c(n1)CCC2]

The title compound, MS (ISP): 292.2 ((M+H)+.) was obtained in comparable yield analogous to the procedure described for Example 210 using isopropylamine instead of ethylamine in step a) and 2,4-dichloro-6,7-dihydro-5H-cyclopentapyrimidine instead of 2-chloro-4-methoxy-pyrimidine in step b).

Example 256

(1H-Imidazol-4-ylmethyl)-isopropyl-(4-methyl-6-phenyl-pyrimidin-2-yl)-amine

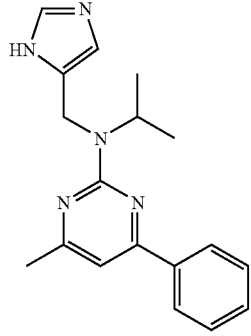 [SMILES: Cc1cc(-c2ccccc2)nc(N(Cc2cnc[nH]2)C(C)C)n1]

The title compound, MS (ISP): 308.4 ((M+H)+.) was obtained in comparable yield analogous to the procedure described for Example 210 using isopropylamine instead of ethylamine in step a) and 2-chloro-4-methyl-6-phenyl-pyrimidine instead of 2-chloro-4-methoxy-pyrimidine in step b).

Example 257

(1H-Imidazol-4-ylmethyl)-isopropyl-[2-(4-methoxy-phenyl)-6-methyl-pyrimidin-4-yl]-amine

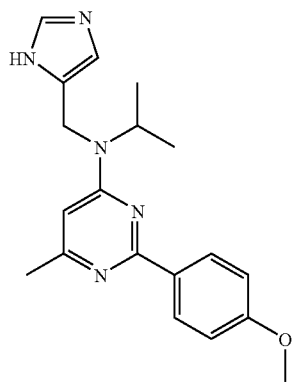

The title compound, MS (ISP): 338.3 ((M+H)+.) was obtained in comparable yield analogous to the procedure described for Example 210 using isopropylamine instead of ethylamine in step a) and 4-chloro-2-(4-methoxy-phenyl)-6-methyl-pyrimidine instead of 2-chloro-4-methoxy-pyrimidine in step b).

Example 258

{2-[(E)-2-(3-Fluoro-phenyl)-vinyl]-6-methyl-pyrimidin-4-yl}-(1H-imidazol-4-ylmethyl)-isopropyl-amine

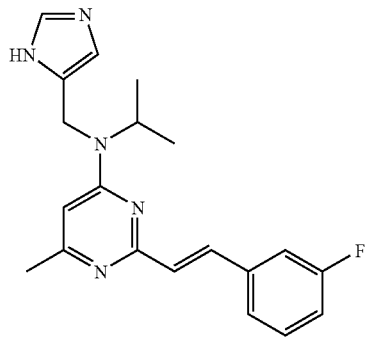 [SMILES: Cc1cc(N(Cc2cnc[nH]2)C(C)C)nc(/C=C/c2cccc(F)c2)n1]

The title compound, MS (ISP): 352.3 ((M+H)+.) was obtained in comparable yield analogous to the procedure described for Example 210 using isopropylamine instead of ethylamine in step a) and 4-chloro-2-[(1E)-2-(3-fluoro-phenyl)-vinyl]-6-methyl-pyrimidine instead of 2-chloro-4-methoxy-pyrimidine in step b).

Example 259

(4-Chloro-6-trifluoromethyl-pyrimidin-2-yl)-(1H-imidazol-4-ylmethyl)-isopropyl-amine

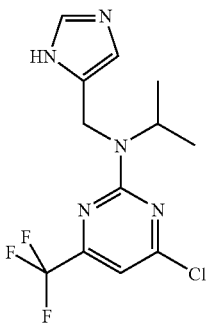 [SMILES: CC(C)N(Cc1cnc[nH]1)c1nc(Cl)cc(C(F)(F)F)n1]

The title compound, MS (ISP): 320.0 ((M+H)+.) was obtained in comparable yield analogous to the procedure described for Example 210 using isopropylamine instead of ethylamine in step a) and 2,4-dichloro-6-trifluoromethyl-pyrimidine instead of 2-chloro-4-methoxy-pyrimidine in step b) and chromatographic separation from the 2-chloro-6-trifluoromethyl-pyrimidin-4-yl isomer before step c).

Example 260

(2-Chloro-6-trifluoromethyl-pyrimidin-4-yl)-(1H-imidazol-4-ylmethyl)-isopropyl-amine

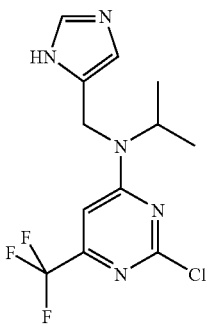 [SMILES: CC(C)N(Cc1cnc[nH]1)c1cc(C(F)(F)F)nc(Cl)n1]

The title compound, MS (ISP): 320.1 ((M+H)+.) was obtained in comparable yield analogous to the procedure described for Example 210 using isopropylamine instead of ethylamine in step a) and 2,4-dichloro-6-trifluoromethyl-pyrimidine instead of 2-chloro-4-methoxy-pyrimidine in step b) and chromatographic separation from the 4-chloro-6-trifluoromethyl-pyrimidin-2-yl isomer before step c).

Example 261

1-{3-[(1H-Imidazol-4-ylmethyl)-amino]-phenyl}-pyrrolidin-2-one

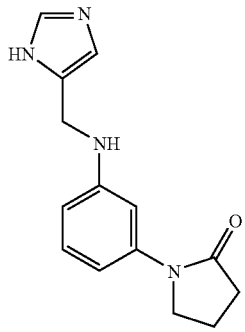

The title compound, MS (ISP): 257.1 ([M+H]+.), was obtained in comparable yield analogous to the procedure described for Example 63 using 1-(3-amino-phenyl)-pyrrolidin-2-one instead of 2-methoxyaniline.

Example 262

(4-Cyclopropyl-phenyl)-(1H-imidazol-4-ylmethyl)-methyl-amine

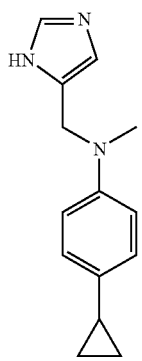 [SMILES: CN(Cc1cnc[nH]1)c1ccc(C2CC2)cc1]

The title compound, MS (ISP): 228.1 ([M+H]+.), was obtained analogous to the procedure described for Example 186 using 4-cyclopropyl-aniline instead of m-anisidine in step a).

Example 263

(3-Cyclopropyl-phenyl)-(1H-imidazol-4-ylmethyl)-methyl-amine

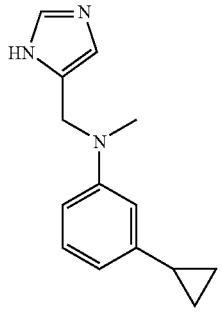 [SMILES: CN(Cc1cnc[nH]1)c1cccc(C2CC2)c1]

The title compound, MS (ISP): 228.1 ([M+H]+.), was obtained analogous to the procedure described for Example 186 using 3-cyclopropyl-aniline instead of m-anisidine in step a).

Example 264

(1H-Imidazol-4-ylmethyl)-(3-pyrrol-1-yl-phenyl)-amine

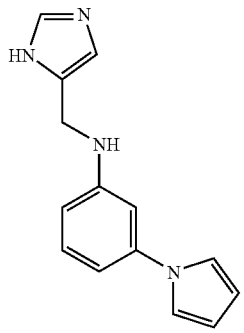 [SMILES: c1cc(NCc2cnc[nH]2)cc(-n2cccc2)c1]

The title compound, MS (ISP): 239.3 ([M+H]$^+$.), was obtained in comparable yield analogous to the procedure described for Example 63 using 3-pyrrol-1-yl-phenylamine instead of 2-methoxyaniline.

Example 265

(1H-Imidazol-4-ylmethyl)-(3-imidazol-1-yl-phenyl)-amine

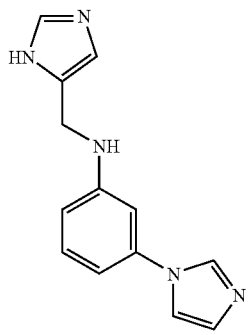 [SMILES: c1cc(NCc2cnc[nH]2)cc(-n2ccnc2)c1]

The title compound, MS (ISP): 240.1 ([M+H]$^+$.), was obtained in comparable yield analogous to the procedure described for Example 63 using 3-(1H-imidazol-1-yl)benzenamine instead of 2-methoxyaniline.

Example 266

(1H-Imidazol-4-ylmethyl)-(3-pyrrolidin-1-yl-phenyl)-amine

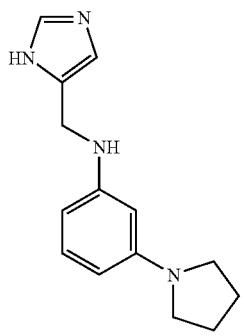 [SMILES: c1cc(NCc2cnc[nH]2)cc(N2CCCC2)c1]

The title compound, MS (ISP): 243.3 ([M+H]$^+$.), was obtained in comparable yield analogous to the procedure described for Example 63 using 3-pyrrolidin-1-yl-phenylamine instead of 2-methoxyaniline.

Example 267

(1H-Imidazol-4-ylmethyl)-isopropyl-(4-morpholin-4-yl-phenyl)-amine

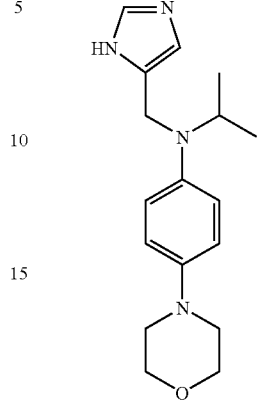

The title compound, MS (ISP): 301.3 ((M+H)$^+$.) was obtained in comparable yield analogous to the procedure described for Example 67 using 4-morpholinoaniline instead of 4-trifluoromethoxyaniline in step a).

Example 268

1-{3-[(1H-Imidazol-4-ylmethyl)-isopropyl-amino]-phenyl}-pyrrolidin-2-one

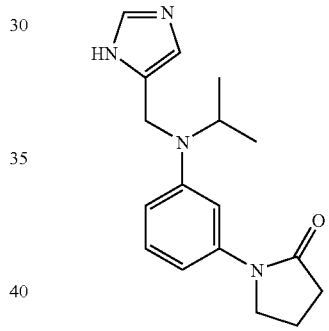

The title compound, MS (ISP): 299.3 ((M+H)$^+$.) was obtained in comparable yield analogous to the procedure described for Example 67 using 1-(3-amino-phenyl)-pyrrolidin-2-one instead of 4-trifluoromethoxyaniline in step a).

Example 269

(1H-Imidazol-4-ylmethyl)-isopropyl-(3-pyrrol-1-yl-phenyl)-amine

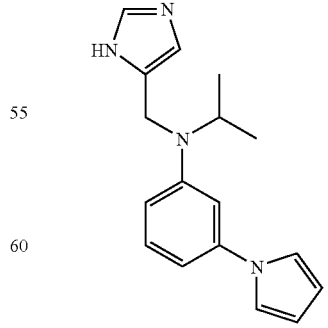

The title compound, MS (ISP): 281.1 ((M+H)$^+$.) was obtained in comparable yield analogous to the procedure described for Example 67 using 3-pyrrol-1-yl-phenylamine instead of 4-trifluoromethoxyaniline in step a).

Example 270

(1H-Imidazol-4-ylmethyl)-(3-imidazol-1-yl-phenyl)-isopropyl-amine

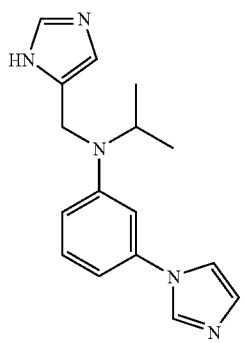 [SMILES: CC(C)N(Cc1cnc[nH]1)c1cccc(-n2ccnc2)c1]

The title compound, MS (ISP): 282.0 ((M+H)⁺.) was obtained in comparable yield analogous to the procedure described for Example 67 using 3-(1H-imidazol-1-yl)benzenamine instead of 4-trifluoromethoxyaniline in step a).

Example 271

(1H-Imidazol-4-ylmethyl)-isopropyl-(3-pyrrolidin-1-yl-phenyl)-amine

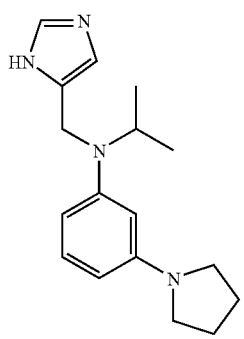 [SMILES: CC(C)N(Cc1cnc[nH]1)c1cccc(N2CCCC2)c1]

The title compound, MS (ISP): 285.0 ((M+H)⁺.) was obtained in comparable yield analogous to the procedure described for Example 67 using 3-pyrrolidin-1-yl-phenylamine instead of 4-trifluoromethoxyaniline in step a).

Example 272

2-[Biphenyl-3-yl-(3H-imidazol-4-ylmethyl)-amino]-ethanol

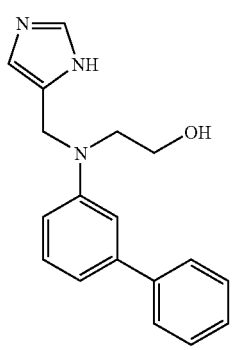 [SMILES: OCCN(Cc1cnc[nH]1)c1cccc(-c2ccccc2)c1]

The title compound, MS (ISP): 294.1 ((M+H)⁺.) was obtained in comparable yield analogous to the procedure described for Example 1 using 2-(biphenyl-3-ylamino)-ethanol instead of N-ethylaniline.

Example 273

(4-Ethoxy-pyrimidin-2-yl)-(3H-imidazol-4-ylmethyl)-isopropyl-amine

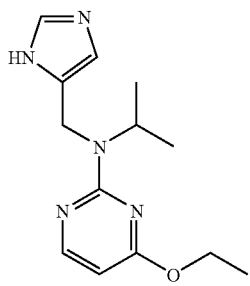 [SMILES: CCOc1ccnc(N(Cc2cnc[nH]2)C(C)C)n1]

The title compound, MS (ISP): 262.1 ((M+H)⁺.) was obtained in comparable yield analogous to the procedure described for Example 229 using the 4-chloro-pyrimidin-2-yl isomer and sodium ethoxide in 1,2-dimethoxyethane instead of sodium hydride/phenol in dimethylformamide in step b).

Example 274

(2-Ethoxy-pyrimidin-4-yl)-(3H-imidazol-4-ylmethyl)-isopropyl-amine

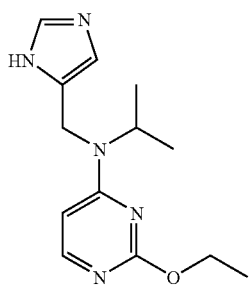 [SMILES: CCOc1nccc(N(Cc2cnc[nH]2)C(C)C)n1]

The title compound, MS (ISP): 262.1 ((M+H)⁺.) was obtained in comparable yield analogous to the procedure described for Example 229 using the 2-chloro-pyrimidin-4-yl isomer and sodium ethoxide in 1,2-dimethoxyethane instead of sodium hydride/phenol in dimethylformamide in step b).

Example 275

(3-Bromo-phenyl)-ethyl-(3H-imidazol-4-ylmethyl)-amine

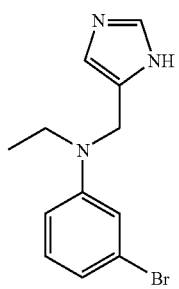 [SMILES: CCN(Cc1cnc[nH]1)c1cccc(Br)c1]

The title compound, MS (ISP): 280.1; 282.2 ((M+H)⁺.) was obtained in comparable yield analogous to the procedure described for Example 81 using 3-bromoaniline instead of 3-chloro-2-fluoroaniline in step a).

Example 276

(4-Fluoro-phenyl)-(1H-imidazol-4-ylmethyl)-amine

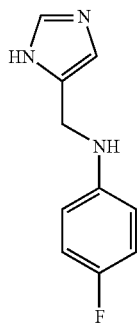 [SMILES: Fc1ccc(NCc2cnc[nH]2)cc1]

The title compound, MS (ISP): 192.3 ([M+H]$^+$.), was obtained in comparable yield analogous to the procedure described for Example 180 using 4-fluoro-aniline instead of 3,4-difluoro-aniline.

Example 277

(3,5-Difluoro-phenyl)-(1H-imidazol-4-ylmethyl)-amine

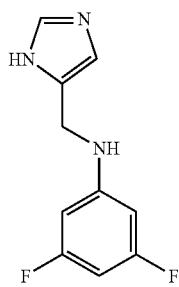 [SMILES: Fc1cc(F)cc(NCc2cnc[nH]2)c1]

The title compound, MS (ISP): 210.3 ([M+H]$^+$.), was obtained in comparable yield analogous to the procedure described for Example 180 using 3,5-difluoro-aniline instead of 3,4-difluoro-aniline.

Example 278

(2,2-Difluoro-benzo[1,3]dioxol-5-yl)-(1H-imidazol-4-ylmethyl)-amine

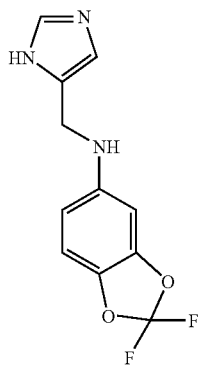 [SMILES: FC1(F)Oc2ccc(NCc3cnc[nH]3)cc2O1]

The title compound, MS (ISP): 254.3 ([M+H]$^+$.), was obtained in comparable yield analogous to the procedure described for Example 180 using 2,2-difluoro-5-aminobenzodioxole instead of 3,4-difluoro-aniline.

Example 279

(3,4-Dibromo-phenyl)-(1H-imidazol-4-ylmethyl)-amine

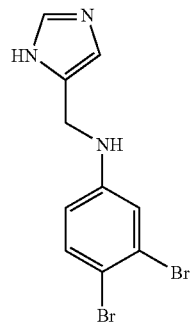

The title compound, MS (ISP): 334.3 ($^{81}$Br$^{81}$Br [M+H]$^+$.), 332.3 ($^{81}$Br$^{79}$Br [M+H]$^+$.), 330.3 ($^{79}$Br$^{79}$Br [M+H]$^+$.), was obtained in comparable yield analogous to the procedure described for Example 180 using 3,4-dibromoaniline instead of 3,4-difluoro-aniline.

Example 280

(1H-Imidazol-4-ylmethyl)-(2,2,3,3-tetrafluoro-2,3-dihydro-benzo[1,4]dioxin-6-yl)-amine

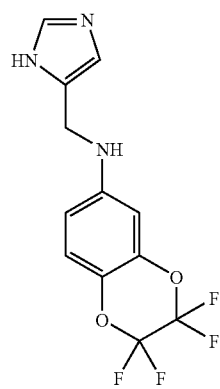 [SMILES: FC1(F)Oc2ccc(NCc3cnc[nH]3)cc2OC1(F)F]

The title compound, MS (ISP): 304.0 ([M+H]$^+$.), was obtained in comparable yield analogous to the procedure described for Example 180 using 2,2,3,3-tetrafluoro-6-aminobenzodioxene instead of 3,4-difluoro-aniline.

Example 281

(3-Chloro-4-fluoro-phenyl)-(1H-imidazol-4-ylmethyl)-amine

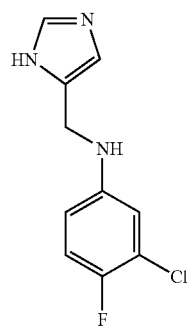 [SMILES: Fc1ccc(NCc2cnc[nH]2)cc1Cl]

The title compound, MS (ISP): 228.1 ($^{37}$Cl [M+H]$^+$.), 226.1 ($^{35}$Cl [M+H]$^+$.), was obtained in comparable yield analogous to the procedure described for Example 180 using 3-chloro-4-fluoro-aniline instead of 3,4-difluoro-aniline.

Example 282

(3,5-Bis-trifluoromethyl-phenyl)-(1H-imidazol-4-ylmethyl)-amine

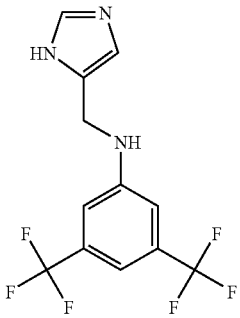

The title compound, MS (ISP): 310.3 ([M+H]⁺.), was obtained in comparable yield analogous to the procedure described for Example 180 using 3,5-bis(trifluoromethyl)-aniline instead of 3,4-difluoro-aniline.

Example 283

(4-Chloro-pyrimidin-2-yl)-(3H-imidazol-4-ylmethyl)-isopropyl-amine

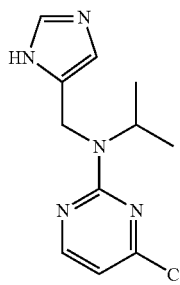

The title compound, MS (ISP): 252.1 ((M+H)⁺.) was obtained in comparable yield analogous to the procedure described for Example 210 using isopropylamine instead of ethylamine in step a) and 2,4-dichloro-pyrimidine instead of 2-chloro-4-methoxy-pyrimidine in step b) and chromatographic separation from the 2-chloro-pyrimidin-4-yl isomer before step c).

Example 284

(3-Bromo-phenyl)-(3H-imidazol-4-ylmethyl)-methyl-amine

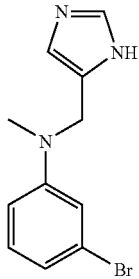

The title compound, MS (ISP): 266.0; 268.1 ((M+H)⁺.) was obtained in comparable yield analogous to the procedure described for Example 81 using 3-bromoaniline instead of 3-chloro-2-fluoroaniline in step a) and formaldehyde solution (40% in water) instead of acetaldehyde in step b).

Example 285

(3-Chloro-4-methoxy-phenyl)-(1H-imidazol-4-ylmethyl)-amine

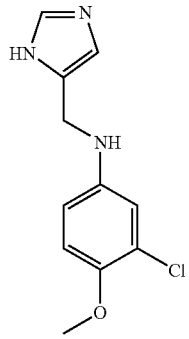 [SMILES: COc1ccc(NCc2cnc[nH]2)cc1Cl]

The title compound, MS (ISP): 240.1 ($^{37}$Cl [M+H]⁺.), 238.0 ($^{35}$Cl [M+H]⁺.), was obtained in comparable yield analogous to the procedure described for Example 63 using 3-chloro-4-methoxy-aniline instead of 2-methoxyaniline.

Example 286

(4-Chloro-3-fluoro-phenyl)-(1H-imidazol-4-ylmethyl)-amine

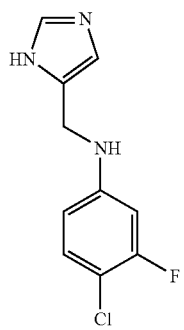 [SMILES: Fc1cc(NCc2cnc[nH]2)ccc1Cl]

The title compound, MS (ISP): 228.1 ($^{37}$Cl [M+H]⁺.), 226.1 ($^{35}$Cl [M+H]⁺.), was obtained in comparable yield analogous to the procedure described for Example 63 using 3-chloro-4-fluoro-aniline instead of 2-methoxyaniline.

Example 287

(3,4-Difluoro-phenyl)-(1H-imidazol-4-ylmethyl)-methyl-amine

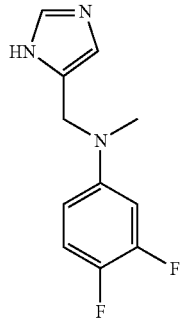 [SMILES: CN(Cc1cnc[nH]1)c1ccc(F)c(F)c1]

The title compound, MS (ISP): 224.4 ([M+H]⁺.), was obtained analogous to the procedure described for Example 186 using 3,4-difluoro-aniline instead of m-anisidine in step a).

Example 288

(3,4-Dichloro-phenyl)-(1H-imidazol-4-ylmethyl)-methyl-amine

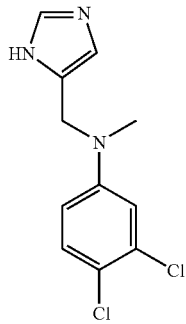 [SMILES: CN(Cc1cnc[nH]1)c1ccc(Cl)c(Cl)c1]

The title compound, MS (ISP): 260.0 ($^{37}$Cl [M+H]$^+$.), 257.9 ($^{37}$Cl $^{35}$Cl [M+H]$^+$.), 256.1 ($^{35}$Cl [M+H]$^+$.), was obtained analogous to the procedure described for Example 186 using 3,4-dichloro-aniline instead of m-anisidine in step a).

Example 289

(4-Fluoro-phenyl)-(1H-imidazol-4-ylmethyl)-methyl-amine

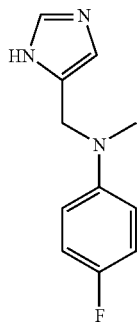

The title compound, MS (ISP): 206.1 ([M+H]$^+$.), was obtained analogous to the procedure described for Example 186 using 4-fluoro-aniline instead of m-anisidine in step a).

Example 290

(4-Bromo-phenyl)-(1H-imidazol-4-ylmethyl)-methyl-amine

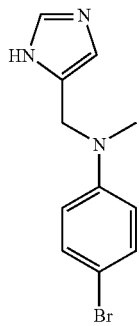

The title compound, MS (ISP): 268.0 ($^{81}$Br [M+H]$^+$.), 266.1 ($^{79}$Br [M+H]$^+$.), was obtained analogous to the procedure described for Example 186 using 4-bromo-aniline instead of m-anisidine in step a).

Example 291

(3,5-Dichloro-phenyl)-(1H-imidazol-4-ylmethyl)-methyl-amine

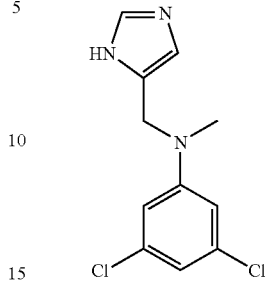

The title compound, MS (ISP): 259.8 ($^{37}$Cl [M+H]$^+$.), 258.0 ($^{37}$Cl $^{35}$Cl [M+H]$^+$.), 256.1 ($^{35}$Cl [M+H]$^+$.), was obtained analogous to the procedure described for Example 186 using 3,5-dichloro-aniline instead of m-anisidine in step a).

Example 292

(3,5-Difluoro-phenyl)-(1H-imidazol-4-ylmethyl)-methyl-amine

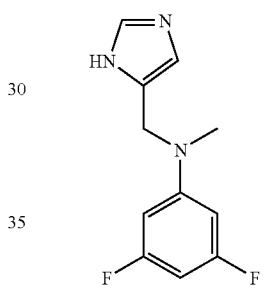

The title compound, MS (ISP): 224.4 ([M+H]$^+$.), was obtained analogous to the procedure described for Example 186 using 3,5-difluoro-aniline instead of m-anisidine in step a).

Example 293

(2,2-Difluoro-benzo[1,3]dioxol-5-yl)-(1H-imidazol-4-ylmethyl)-methyl-amine

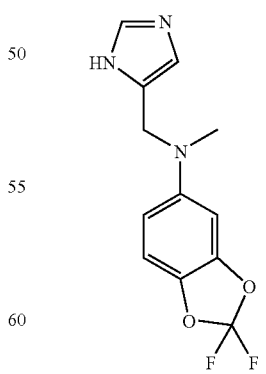

The title compound, MS (ISP): 268.1 ([M+H]$^+$.), was obtained analogous to the procedure described for Example 186 using 2,2-difluoro-5-amino-benzodioxole instead of m-anisidine in step a).

Example 294

(3-Chloro-4-fluoro-phenyl)-(1H-imidazol-4-ylm-ethyl)-methyl-amine

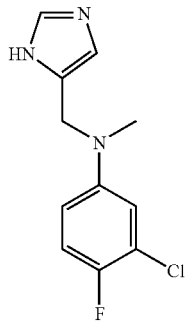 [SMILES: CN(Cc1cnc[nH]1)c1ccc(F)c(Cl)c1]

The title compound, MS (ISP): MS (ISP): 242.2 ([$^{37}$Cl M+H]$^+$.), 240.1 ([$^{35}$Cl M+H]$^+$.), was obtained analogous to the procedure described for Example 186 using 3-chloro-4-fluoro-aniline instead of m-anisidine in step a).

Example 295

(3-Chloro-5-fluoro-phenyl)-(1H-imidazol-4-ylm-ethyl)-methyl-amine

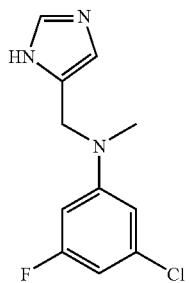 [SMILES: CN(Cc1cnc[nH]1)c1cc(F)cc(Cl)c1]

The title compound, MS (ISP): MS (ISP): 242.2 ([$^{37}$Cl M+H]$^+$.), 240.1 ([$^{35}$Cl M+H]$^+$.), was obtained analogous to the procedure described for Example 186 using 3-chloro-5-fluoro-aniline instead of m-anisidine in step a).

Example 296

(4-Bromo-phenyl)-(1H-imidazol-4-ylmethyl)-isopropyl-amine

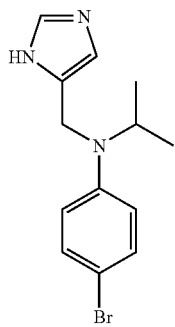 [SMILES: CC(C)N(Cc1cnc[nH]1)c1ccc(Br)cc1]

The title compound, MS (ISP): 296.1 ([$^{81}$Br M+H]$^+$.), 294.0 ([$^{79}$Br M+H]$^+$.), was obtained in comparable yield analogous to the procedure described for Example 67 using 4-bromo-aniline instead of 4-trifluoromethoxyaniline in step a).

Example 297

(3,4-Dibromo-phenyl)-(1H-imidazol-4-ylmethyl)-isopropyl-amine

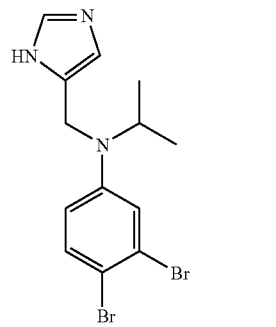

4-Bromo-phenyl)-(1H-imidazol-4-ylmethyl)-amine

The title compound, MS (ISP): 334.1 ([$^{81}$Br M+H]$^+$.), 331.9 ([$^{81}$Br$^{79}$Br M+H]$^+$), 329.9 ([$^{79}$Br M+H]$^+$.), was obtained in comparable yield analogous to the procedure described for Example 180 using 3,4-dibromoaniline instead of 3,4-difluoroaniline.

(3,4-Dibromo-phenyl)-(1H-imidazol-4-ylmethyl)-isopropyl-amine

The title compound, MS (ISP): 376.1 ([$^{81}$Br M+H]$^+$.), 374.1 ([$^{81}$Br$^{79}$Br M+H]$^+$.), 372.0 ([$^{79}$Br M+H]$^+$.), was obtained analogous to the procedure described for Example 67 step b).

Example 298

(1H-Imidazol-4-ylmethyl)-isopropyl-(2,2,3,3-tetrafluoro-2,3-dihydro-benzo[1,4]dioxin-6-yl)-amine

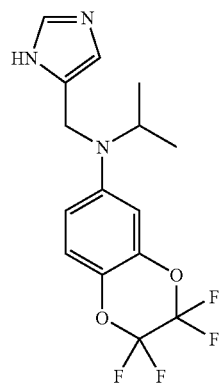 [SMILES: CC(C)N(Cc1cnc[nH]1)c1ccc2c(c1)OC(F)(F)C(F)(F)O2]

The title compound, MS (ISP): 346.3 ([M+H]$^+$.), was obtained in comparable yield analogous to the procedure described for Example 297 using 2,2,3,3-tetrafluoro-6-aminobenzodioxene instead of 3,4-dibromoaniline in step a).

Example 299

(4-Chloro-3-fluoro-phenyl)-(1H-imidazol-4-ylmethyl)-isopropyl-amine

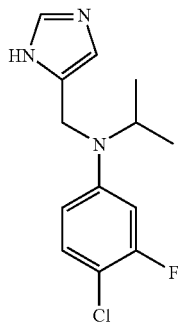 [SMILES: CC(C)N(Cc1cnc[nH]1)c1ccc(Cl)c(F)c1]

The title compound, MS (ISP): 270.2 ([$^{37}$Cl M+H]$^+$.), 268.2 ([$^{35}$Cl M+H]$^+$.), was obtained in comparable yield analogous to the procedure described for Example 67 using 4-chloro-3-fluoro-aniline instead of 4-trifluoromethoxyaniline in step a).

Example 300

(3,5-Bis-trifluoromethyl-phenyl)-(1H-imidazol-4-ylmethyl)-isopropyl-amine

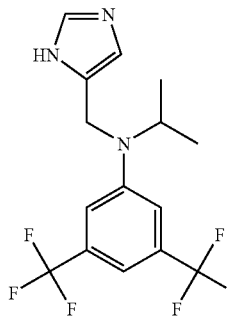

The title compound, MS (ISP): 352.5 ([M+H]$^+$.), was obtained in comparable yield analogous to the procedure described for Example 297 using 3,5-bis(trifluoromethyl)aniline instead of 3,4-dibromoaniline in step a).

Example 301

Ethyl-(4-fluoro-phenyl)-(1H-imidazol-4-ylmethyl)-amine

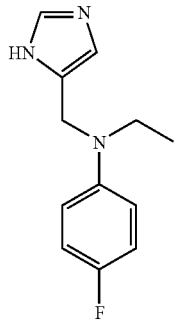

(4-Fluoro-phenyl)-(1H-imidazol-4-ylmethyl)-amine

To a solution of 4-fluoroaniline (0.60 g, 5.40 mmol) in 1,2-dichloroethane (5 ml) were added 4-formylimidazole (0.78 g, 8.10 mmol), sodium triacetoxyborohydride (2.29 g, 10.8 mmol) and acetic acid (0.06 ml). The reaction mixture was stirred at 50° C. for 4 h. The reaction mixture was then concentrated in vacuo and the residue was purified using flash chromatography (column: Isolute® Flash-NH$_2$ (Separtis); eluent: methanol/dichloromethane gradient) to yield a white solid (160 mg, 16%); MS (ISP): 192.2 ((M+H)$^+$.).

Ethyl-(4-fluoro-phenyl)-(1H-imidazol-4-ylmethyl)-amine

To a solution of (4-fluoro-phenyl)-(1H-imidazol-4-ylmethyl)-amine (0.20 g, 1.05 mmol) in 1,2-dichloroethane (6 ml) were added acetaldehyde (0.30 ml, 5.23 mmol), sodium triacetoxyborohydride (0.67 g, 3.14 mmol) and acetic acid (0.06 ml). The reaction mixture was stirred at 40° C. for 16 h. The reaction mixture was then concentrated in vacuo and the residue was purified using flash chromatography (column: Isolute® Flash-NH$_2$ (Separtis); eluent: methanol/ethyl acetate/heptane gradient) to yield a white solid (131 mg, 57%); MS (ISP): 220.4 ((M+H)$^+$.).

Example 302

(4-Bromo-phenyl)-ethyl-(1H-imidazol-4-ylmethyl)-amine

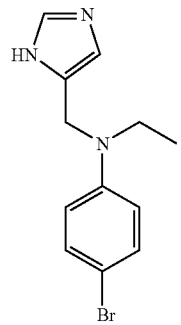 [SMILES: CCN(Cc1cnc[nH]1)c1ccc(Br)cc1]

(4-Bromo-phenyl)-(1H-imidazol-4-ylmethyl)-amine

The title compound, MS (ISP): 254.0 ([$^{81}$Br M+H]$^+$.), 252.1 ([$^{79}$Br M+H]$^+$.), was obtained in comparable yield analogous to the procedure described for Example 63 using 4-bromoaniline instead of 2-methoxyaniline.

(4-Bromo-phenyl)-ethyl-(1H-imidazol-4-ylmethyl)-amine

The title compound, MS (ISP): 282.1 ([$^{81}$Br M+H]$^+$.), 280.0 ([$^{79}$Br M+H]$^+$.), was obtained analogous to the procedure described for Example 301 step b).

Example 303

(3,5-Dichloro-phenyl)-ethyl-(1H-imidazol-4-ylmethyl)-amine

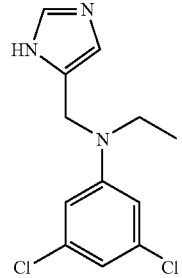 [SMILES: CCN(Cc1cnc[nH]1)c1cc(Cl)cc(Cl)c1]

The title compound, MS (ISP): 274.0 ([$^{37}$Cl M+H]$^+$.), 272.1 ([$^{37}$Cl $^{35}$Cl M+H]$^+$.), 270.2 ([$^{35}$Cl M+H]$^+$.), was obtained analogous to the procedure described for Example 301 using 3,5-dichloro-aniline instead of 4-fluoroaniline in step a).

Example 304

(3-Chloro-phenyl)-ethyl-(1H-imidazol-4-ylmethyl)-amine

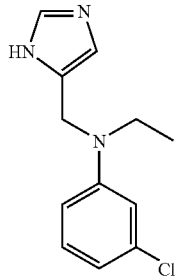

The title compound, MS (ISP): 238.0 ($[^{37}Cl\ M+H]^+$.), 236.1 ($[^{35}Cl\ M+H]^+$.), was obtained analogous to the procedure described for Example 301 using 3,5-dichloro-aniline instead of 4-fluoroaniline in step a).

Example 305

(4-Bromo-3-fluoro-phenyl)-ethyl-(1H-imidazol-4-ylmethyl)-amine

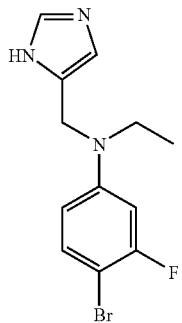

The title compound, MS (ISP): 300.0 ($[^{81}Br\ M+H]^+$.), 298.1 ($[^{79}Br\ M+H]^+$.), was obtained analogous to the procedure described for Example 301 using 4-bromo-3-fluoro-aniline instead of 4-fluoroaniline in step a).

Example 306

(3,5-Difluoro-phenyl)-ethyl-(1H-imidazol-4-ylmethyl)-amine

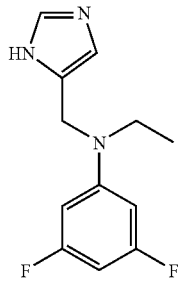 [SMILES: CCN(Cc1cnc[nH]1)c1cc(F)cc(F)c1]

The title compound, MS (ISP): 238.1 ($[M+H]^+$.), was obtained analogous to the procedure described for Example 301 using 3,5-difluoro-aniline instead of 4-fluoroaniline in step a).

Example 307

(4-Chloro-3-fluoro-phenyl)-ethyl-(1H-imidazol-4-ylmethyl)-amine

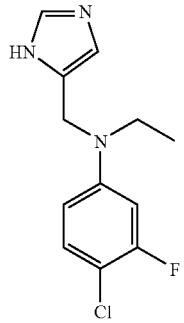

The title compound, MS (ISP): 256.0 ($[^{37}Cl\ M+H]^+$.), 254.1 ($[^{35}Cl\ M+H]^+$.), was obtained analogous to the procedure described for Example 302 using 4-chloro-3-fluoro-aniline instead of 4-bromoaniline in step a).

Example 308

(3-Chloro-5-fluoro-phenyl)-ethyl-(1H-imidazol-4-ylmethyl)-amine

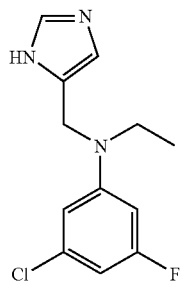 [SMILES: CCN(Cc1cnc[nH]1)c1cc(F)cc(Cl)c1]

The title compound, MS (ISP): 256.0 ($[^{37}Cl\ M+H]^+$.), 253.9 ($[^{35}Cl\ M+H]^+$.), was obtained analogous to the procedure described for Example 302 using 3-chloro-5-fluoro-aniline instead of 4-bromoaniline in step a).

Example 309

(3-Bromo-4-fluoro-phenyl)-ethyl-(1H-imidazol-4-ylmethyl)-amine

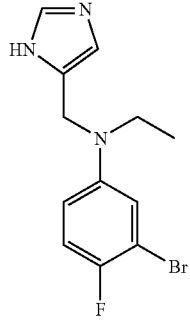

The title compound, MS (ISP): 300.0 ($[^{81}Br\ M+H]^+$.), 298.1 ($[^{79}Br\ M+H]^+$.), was obtained analogous to the procedure described for Example 301 using 3-bromo-4-fluoro-aniline instead of 4-fluoroaniline in step a).

Example 310

(2,2-Difluoro-benzo[1,3]dioxol-5-yl)-ethyl-(1H-imidazol-4-ylmethyl)-amine

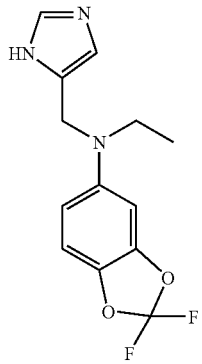 [SMILES: CCN(Cc1cnc[nH]1)c1ccc2c(c1)OC(F)(F)O2]

The title compound, MS (ISP): 282.0 ([M+H]$^+$.), was obtained analogous to the procedure described for Example 302 using 2,2-difluoro-5-amino-benzodioxole instead of 4-bromoaniline in step a).

Example 311

(2,2-Difluoro-benzo[1,3]dioxol-5-yl)-(1H-imidazol-4-ylmethyl)-isopropyl-amine

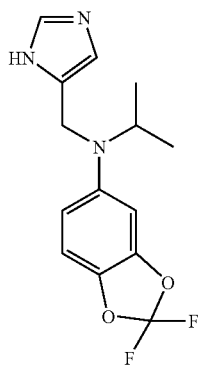 [SMILES: CC(C)N(Cc1cnc[nH]1)c1ccc2c(c1)OC(F)(F)O2]

The title compound, MS (ISP): 296.4 ([M+H]$^+$.), was obtained in comparable yield analogous to the procedure described for Example 67 using 2,2-difluoro-5-aminobenzodioxole instead of 4-trifluoromethoxyaniline in step a).

Example 312

(3-Chloro-4-fluoro-phenyl)-ethyl-(1H-imidazol-4-ylmethyl)-amine

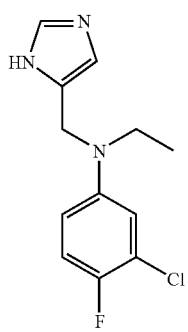

The title compound, MS (ISP): 256.1 ([$^{37}$Cl M+H]$^+$.), 253.9 ([$^{35}$Cl M+H]$^+$.), was obtained analogous to the procedure described for Example 302 using 3-chloro-4-fluoro-aniline instead of 4-bromoaniline in step a).

Example 313

(3H-Imidazol-4-ylmethyl)-isopropyl-(6-trifluoromethyl-pyridin-2-yl)-amine

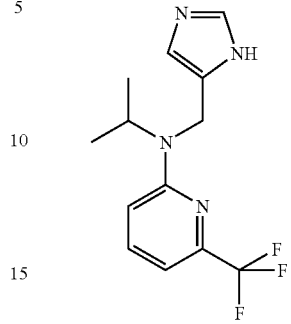

The title compound, MS (ISP): 285.0 ((M+H)$^+$.) was obtained in comparable yield analogous to the procedure described for Example 67 using 2-amino-6-trifluoromethyl-pyridine instead of 4-trifluormethoxyaniline in step a).

Example 314

Biphenyl-3-yl-(3H-imidazol-4-ylmethyl)-amine

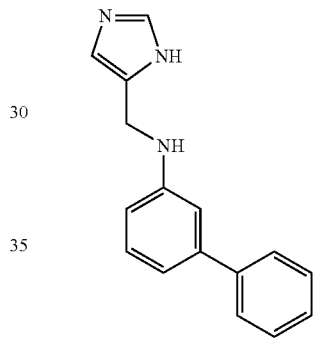

The title compound, MS (ISP): 250.1 ((M+H)$^+$.) was obtained in comparable yield analogous to the procedure described for Example 63 using 3-aminobiphenyl instead of 2-methoxyaniline.

Example 315

(3H-Imidazol-4-ylmethyl)-(4'-trifluoromethyl-biphenyl-3-yl)-amine

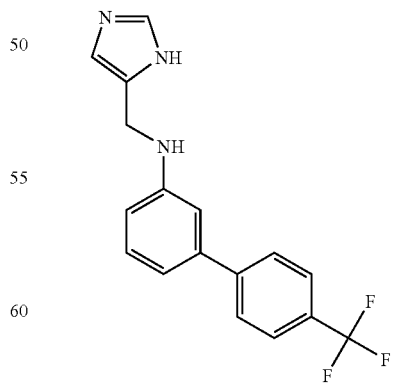

The title compound, MS (ISP): 318.0 ((M+H)$^+$.) was obtained in comparable yield analogous to the procedure described for Example 63 using 4'-trifluoromethyl-biphenyl-3-ylamine instead of 2-methoxyaniline.

Example 316

(3'-Chloro-biphenyl-3-yl)-(3H-imidazol-4-ylmethyl)-amine

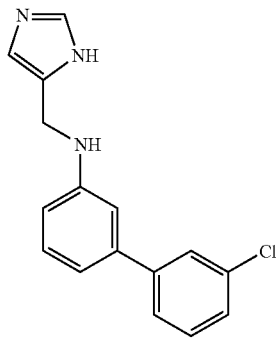 [SMILES: Clc1cccc(-c2cccc(NCc3cnc[nH]3)c2)c1]

The title compound, MS (ISP): 284.0 ((M+H)$^+$.) was obtained in comparable yield analogous to the procedure described for Example 63 using 3'-chloro-biphenyl-3-ylamine instead of 2-methoxyaniline.

Example 317

(1H-Imidazol-4-ylmethyl)-isopropyl-(4-trifluoromethyl-pyrimidin-2-yl)-amine

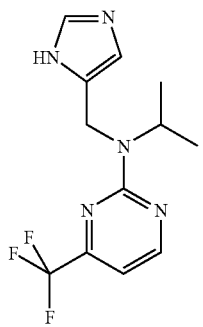 [SMILES: CC(C)N(Cc1cnc[nH]1)c1nccc(C(F)(F)F)n1]

The title compound, MS (ISP): 286.3 ((M+H)$^+$.) was obtained in comparable yield analogous to the procedure described for Example 210 using isopropylamine instead of ethylamine in step a) and 2-chloro-4-(trifluoromethyl)-pyrimidine instead of 2-chloro-4-methoxy-pyrimidine in step b).

Example 318

(1H-Imidazol-4-ylmethyl)-isopropyl-(2-trifluoromethyl-pyrimidin-4-yl)-amine

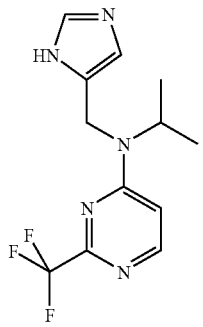 [SMILES: CC(C)N(Cc1cnc[nH]1)c1ccnc(C(F)(F)F)n1]

The title compound, MS (ISP): 286.0 ((M+H)$^+$.) was obtained in comparable yield analogous to the procedure described for Example 210 using isopropylamine instead of ethylamine in step a) and 4-chloro-2-(trifluoromethyl)-pyrimidine instead of 2-chloro-4-methoxy-pyrimidine in step b).

Example 319

(1H-Imidazol-4-ylmethyl)-isopropyl-(6-methoxy-pyrimidin-4-yl)-amine

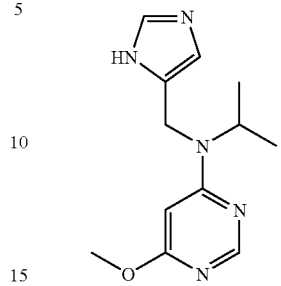

The title compound, MS (ISP): 248.1 ((M+H)$^+$.) was obtained in comparable yield analogous to the procedure described for Example 210 using isopropylamine instead of ethylamine in step a) and 4-chloro-6-methoxy-pyrimidine instead of 2-chloro-4-methoxy-pyrimidine in step b).

Example 320

(1H-Imidazol-4-ylmethyl)-isopropyl-(6-phenyl-pyrimidin-4-yl)-amine

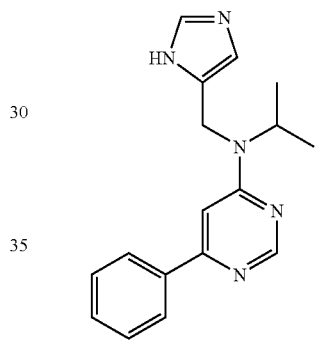

The title compound, MS (ISP): 294.2 ((M+H)$^+$.) was obtained in comparable yield analogous to the procedure described for Example 210 using isopropylamine instead of ethylamine in step a) and 4-chloro-6-phenyl-pyrimidine instead of 2-chloro-4-methoxy-pyrimidine in step b).

Example 321

(1H-Imidazol-4-ylmethyl)-methyl-(2-trifluoromethyl-pyrimidin-4-yl)-amine

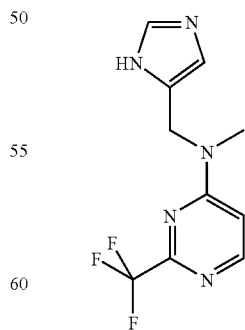

The title compound, MS (ISP): 258.0 ((M+H)$^+$.) was obtained in comparable yield analogous to the procedure described for Example 210 using methylamine instead of ethylamine in step a) and 4-chloro-2-(trifluoromethyl)-pyrimidine instead of 2-chloro-4-methoxy-pyrimidine in step b).

Example 322

(3-Chloro-4-methoxy-phenyl)-ethyl-(1H-imidazol-4-ylmethyl)-amine

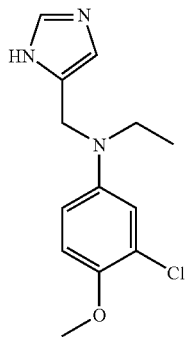 [SMILES: CCN(Cc1cnc[nH]1)c1ccc(OC)c(Cl)c1]

The title compound, MS (ISP): 268.2 ($[^{37}Cl$ M+H$]^+$.), 266.1 ($[^{35}Cl$ M+H$]^+$.), was obtained analogous to the procedure described for Example 302 using 3-chloro-4-methoxy-aniline instead of 4-bromoaniline in step a).

Example 323

(4-Chloro-3-fluoro-phenyl)-(1H-imidazol-4-ylmethyl)-methyl-amine

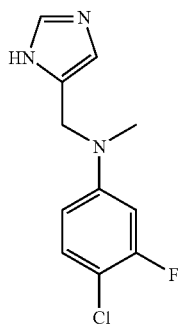 [SMILES: CN(Cc1cnc[nH]1)c1ccc(Cl)c(F)c1]

The title compound, MS (ISP): 242.1 ($[^{37}Cl$ M+H$]^+$.), 240.1 ($[^{35}Cl$ M+H$]^+$.), was obtained analogous to the procedure described for Example 186 using 4-chloro-3-fluoro-aniline instead of m-anisidine in step a).

Example 324

(4-Chloro-3-methoxy-phenyl)-ethyl-(1H-imidazol-4-ylmethyl)-amine

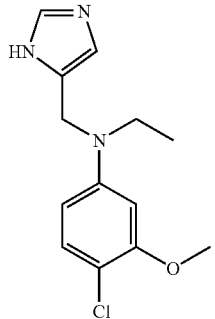 [SMILES: CCN(Cc1cnc[nH]1)c1ccc(Cl)c(OC)c1]

The title compound, MS (ISP): 268.2 ($[^{37}Cl$ M+H$]^+$.), 266.2 ($[^{35}Cl$ M+H$]^+$.), was obtained analogous to the procedure described for Example 302 using 4-chloro-3-methoxy-aniline instead of 4-bromoaniline in step a).

Example 325

(4-Bromo-3-chloro-phenyl)-(1H-imidazol-4-ylmethyl)-amine

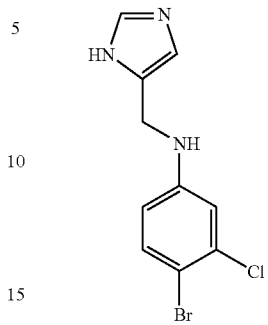

The title compound, MS (ISP): 290.1 ($^{81}Br\,^{37}Cl$ [M+H]$^+$.), 288.1 ($^{81}Br\,^{35}Cl\,^{79}Br^{37}C$ [M+H]$^+$.), 286.1 ($^{79}Br^{35}Cl$ [M+H]$^+$.), was obtained in comparable yield analogous to the procedure described for Example 63 using 4-bromo-3-chloro-aniline instead of 2-methoxyaniline.

Example 326

(1H-Imidazol-4-ylmethyl)-(4-trifluoromethoxy-phenyl)-amine

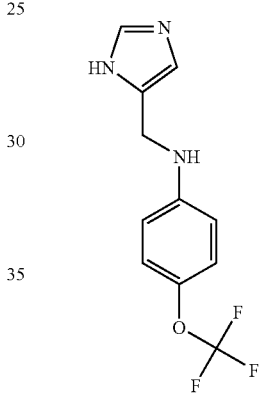

The title compound, MS (ISP): 258.3 ([M+H]$^+$.), was obtained in comparable yield analogous to the procedure described for Example 63 using 4-(trifluoromethoxy)-aniline instead of 2-methoxyaniline.

Example 327

(3-Chloro-4-trifluoromethoxy-phenyl)-(1H-imidazol-4-ylmethyl)-amine

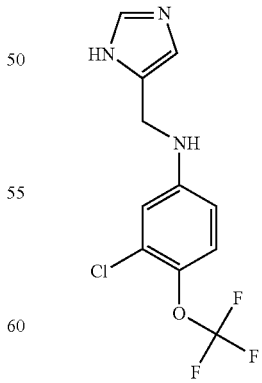

The title compound, MS (ISP): 294.0 ($^{37}Cl$ [M+H]$^+$.), 292.1 ($^{35}Cl$ [M+H]$^+$.), was obtained in comparable yield analogous to the procedure described for Example 63 using 3-chloro-4-(trifluoromethyoxy)aniline instead of 2-methoxyaniline.

Example 328

(1H-Imidazol-4-ylmethyl)-[4-(2,2,2-trifluoro-ethoxy)-phenyl]-amine

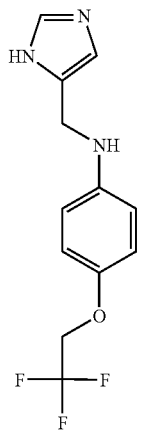

The title compound, MS (ISP): 272.1 ([M+H]$^+$.), was obtained in comparable yield analogous to the procedure described for Example 63 using 4-(2,2,2-trifluoro-ethoxy)-phenylamine instead of 2-methoxyaniline.

Example 329

(1H-Imidazol-4-ylmethyl)-[3-(1,1,2,2-tetrafluoro-ethoxy)-phenyl]-amine

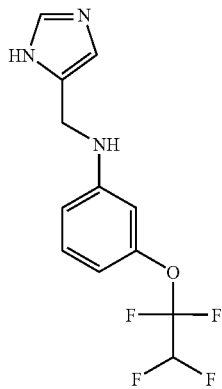 [SMILES: FC(F)C(F)(F)Oc1cccc(NCc2cnc[nH]2)c1]

The title compound, MS (ISP): 290.0 ([M+H]$^+$.), was obtained in comparable yield analogous to the procedure described for Example 63 using 3-(1,1,2,2-tetrafluoroethoxy) aniline instead of 2-methoxyaniline.

Example 330

Ethyl-(1H-imidazol-4-ylmethyl)-(4-methoxy-phenyl)-amine

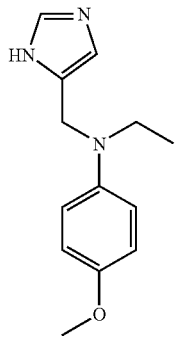 [SMILES: CCN(Cc1cnc[nH]1)c1ccc(OC)cc1]

The title compound, MS (ISP): 232.1 ([M+H]$^+$.), was obtained analogous to the procedure described for Example 302 using 4-methoxy-aniline instead of 4-bromoaniline in step a).

Example 331

(4-Bromo-3-chloro-phenyl)-(1#H!-imidazol-4-ylm-ethyl)-isopropyl-amine

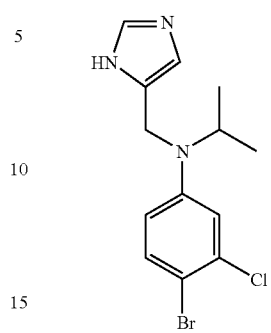

The title compound, MS (ISP): 332.1 ($^{81}$Br $^{37}$Cl [M+H]$^+$.), 330.0 ($^{81}$Br $^{35}$Cl/$^{79}$Br $^{37}$Cl [M+H]$^+$.), 328.1 ($^{79}$Br$^{35}$Cl [M+H]$^+$.), was obtained in comparable yield analogous to the procedure described for Example 67 using 4-bromo-3-chloro-aniline instead of 4-trifluoromethoxyaniline in step a).

Example 332

Ethyl-(1H-imidazol-4-ylmethyl)-(4-trifluo-romethoxy-phenyl)-amine

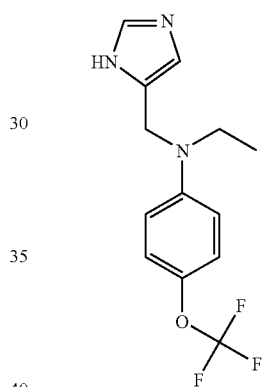

The title compound, MS (ISP): 286.1 ([M+H]$^+$.), was obtained analogous to the procedure described for Example 302 using 4-trifluoromethoxy-aniline instead of 4-bromoaniline in step a).

Example 333

(3-Chloro-4-trifluoromethoxy-phenyl)-ethyl-(1H-imidazol-4-ylmethyl)-amine

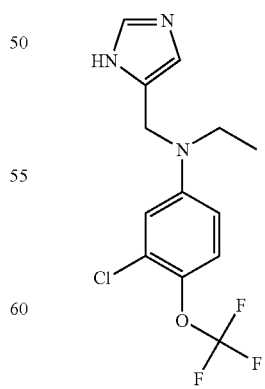

The title compound, MS (ISP): 322.2 ([$^{37}$Cl M+H]$^+$.), 320.1 ([$^{35}$Cl M+H]$^+$.), was obtained analogous to the procedure described for Example 302 using 3-chloro-4-trifluoromethoxy-aniline instead of 4-bromoaniline in step a).

Example 334

(1H-Imidazol-4-ylmethyl)-isopropyl-[4-(2,2,2-trifluoro-ethoxy)-phenyl]-amine

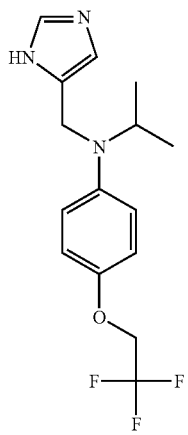 [SMILES: CC(C)N(Cc1cnc[nH]1)c1ccc(OCC(F)(F)F)cc1]

The title compound, MS (ISP): 314.0 ([M+H]⁺.), was obtained in comparable yield analogous to the procedure described for Example 67 using 4-(2,2,2-trifluoro-ethoxy)-phenylamine instead of 4-trifluoromethoxyaniline in step a).

Example 335

(3-Bromo-4-fluoro-phenyl)-(1H-imidazol-4-ylmethyl)-methyl-amine

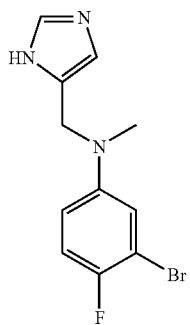

The title compound, MS (ISP): MS (ISP): 285.9 ([⁸¹Br M+H]⁺.), 283.9 ([⁷⁹Br M+H]⁺.), was obtained analogous to the procedure described for Example 186 using 3-bromo-4-fluoro-aniline instead of m-anisidine in step a).

Example 336

Ethyl-(1H-imidazol-4-ylmethyl)-[3-(1,1,2,2-tetrafluoro-ethoxy)-phenyl]-amine

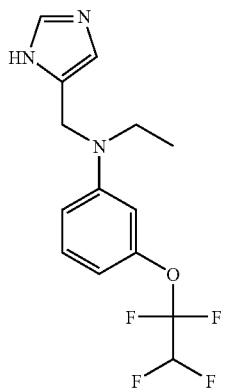 [SMILES: CCN(Cc1cnc[nH]1)c1cccc(OC(F)(F)C(F)F)c1]

The title compound, MS (ISP): 318.0 ([M+H]⁺.), was obtained analogous to the procedure described for Example 302 using 3-(1,1,2,2-tetrafluoroethoxy)aniline instead of 4-bromoaniline in step a).

Example 337

(6-Chloro-pyrimidin-4-yl)-(1H-imidazol-4-ylmethyl)-isopropyl-amine

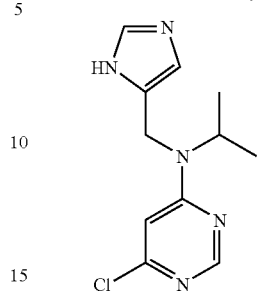

The title compound, MS (ISP): 252.1 ((M+H)⁺.) was obtained in comparable yield analogous to the procedure described for Example 210 using isopropylamine instead of ethylamine in step a) and 4,6-dichloropyrimidine instead of 2-chloro-4-methoxy-pyrimidine in step b).

Example 338

(1H-Imidazol-4-ylmethyl)-isopropyl-(1-methyl-1H-pyrazol-3-yl)-amine

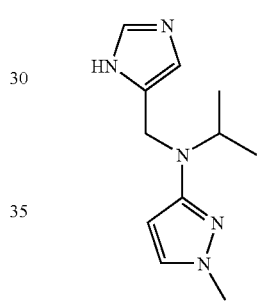

The title compound, MS (ISP): 220.4 ([M+H]⁺.), was obtained in comparable yield analogous to the procedure described for Example 67 using 3-amino-1-methylpyrazole instead of 4-trifluoromethoxyaniline in step a).

Example 339

(1H-Imidazol-4-ylmethyl)-isopropyl-(1-phenyl-1H-pyrazol-3-yl)-amine

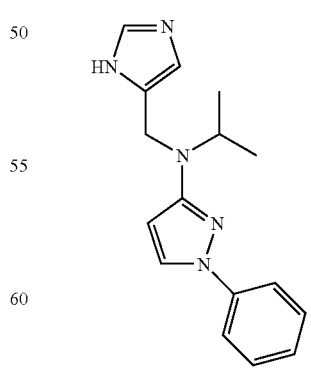

The title compound, MS (ISP): 282.1 ([M+H]⁺.), was obtained in comparable yield analogous to the procedure described for Example 67 using 1-phenyl-1H-pyrazol-3-ylamine instead of 4-trifluoromethoxyaniline in step a).

Example 340

Ethyl-(1H-imidazol-4-ylmethyl)-(2-methyl-2H-pyrazol-3-yl)-amine

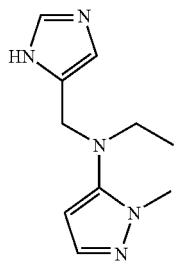

The title compound, MS (ISP): 206.1 ([M+H]$^+$.), was obtained analogous to the procedure described for Example 302 using 5-amino-1-methylpyrazole instead of 4-bromoaniline in step a).

Example 341

Ethyl-(1H-imidazol-4-ylmethyl)-(1-phenyl-1H-pyrazol-3-yl)-amine

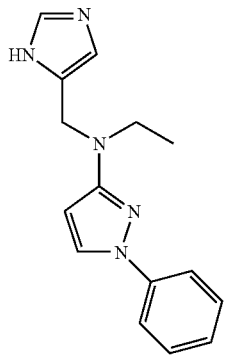 [SMILES: CCN(Cc1cnc[nH]1)c1ccn(-c2ccccc2)n1]

The title compound, MS (ISP): 268.3 ([M+H]$^+$.), was obtained analogous to the procedure described for Example 302 using 1-phenyl-1H-pyrazol-3-ylamine instead of 4-bromoaniline in step a).

Example 342

(1H-Imidazol-4-ylmethyl)-(4-trifluoromethyl-thiazol-2-yl)-amine

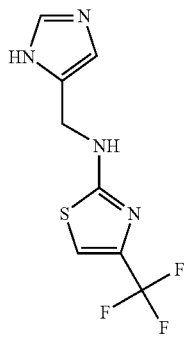 [SMILES: FC(F)(F)c1csc(NCc2cnc[nH]2)n1]

The title compound, MS (ISP): 249.1 ([M+H]$^+$.), was obtained in comparable yield analogous to the procedure described for Example 63 using 4-(trifluoromethyl)-1,3-thiazol-2-amine instead of 2-methoxyaniline.

Example 343

(1H-Imidazol-4-ylmethyl)-(2-methoxy-pyrimidin-4-yl)-(2,2,2-trifluoro-ethyl)-amine

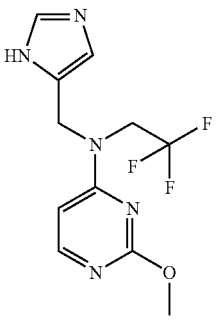 [SMILES: COc1nccc(N(Cc2cnc[nH]2)CC(F)(F)F)n1]

The title compound, MS (ISP): 288.1 ((M+H)$^+$.) was obtained in comparable yield analogous to the procedure described for Example 229 using 2,2,2-trifluoroethylamine instead of ethylamine in step a) and sodium methoxide in 1,2-dimethoxyethane instead of sodium hydride/phenol in dimethylformamide in step b).

Example 344

(1H-Imidazol-4-ylmethyl)-(2,2,2-trifluoro-ethyl)-(4-trifluoromethyl-pyrimidin-2-yl)-amine

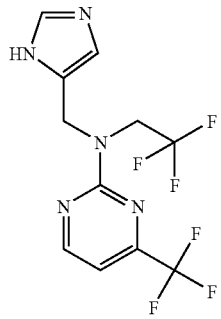 [SMILES: FC(F)(F)CN(Cc1cnc[nH]1)c1nccc(C(F)(F)F)n1]

The title compound, MS (ISP): 326.3 ((M+H)$^+$.) was obtained in comparable yield analogous to the procedure described for Example 210 using 2,2,2-trifluoroethylamine instead of ethylamine in step a) and 2-chloro-4-(trifluoromethyl)-pyrimidine instead of 2-chloro-4-methoxy-pyrimidine in step b).

Example 345

(6-Chloro-pyrazin-2-yl)-(3H-imidazol-4-ylmethyl)-amine

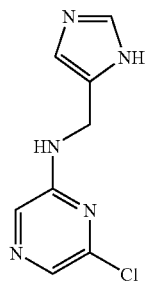 [SMILES: Clc1cncc(NCc2cnc[nH]2)n1]

The title compound, MS (ISP): 209.8; 211.8 ((M+H)+.) was obtained in comparable yield analogous to the procedure described for Example 63 using 2-amino-6-chloropyrazine instead of 2-methoxyaniline.

Example 346

(6-Chloro-pyrazin-2-yl)-(3H-imidazol-4-ylmethyl)-isopropyl-amine

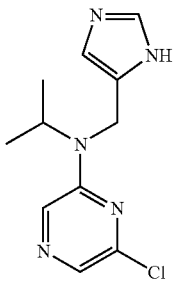 [SMILES: CC(C)N(Cc1cnc[nH]1)c1cncc(Cl)n1]

The title compound, MS (ISP): 252.3; 254.3 ((M+H)+.) was obtained in comparable yield analogous to the procedure described for Example 67 using 2-amino-6-chloropyrazine instead of 4-trifluormethoxyaniline in step a).

Example 347

The ability of the compounds of the present invention to bind to TAAR1 was investigated in accordance with the test given hereinafter.
Materials and Methods
Construction of TAAR Expression Plasmids and Stably Transfected Cell Lines For the construction of expression plasmids the coding sequences of human, rat and mouse TAAR 1 were amplified from genomic DNA essentially as described by Lindemann et al. (2005) *Genomics* 85, 372-385. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described Lindemann et al. (2005) *Genomics* 85, 372-385. For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hours post transfection the culture medium was supplemented with 1 mg/ml G418 (Sigma, Buchs, Switzerland). After a culture period of about 10 days, clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.
Membrane Preparation and Radioligand Binding Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. The cell pellet was then suspended in 20 ml HEPES-NaOH (20 mM), pH 7.4 containing 10 mM EDTA, and homogenized with a Polytron (PT 3000, Kinematica) at 10,000 rpm for 10 seconds. The homogenate was centrifuged at 48,000×g for 30 minutes at 4° C. and the pellet resuspended in 20 ml HEPES-NaOH (20 mM), pH 7.4 containing 0.1 mM EDTA (buffer A), and homogenized with a Polytron at 10,000 rpm for 10 seconds. The homogenate was then centrifuged at 48,000×g for 30 minutes at 4° C. and the pellet resuspended in 20 ml buffer A, and homogenized with a Polytron at 10,000 rpm for 10 seconds. Protein concentration was determined by the method of Pierce (Rockford, Ill.). The homogenate was then centrifuged at 48,000×g for 10 minutes at 4° C., resuspended in HEPES-NaOH (20 mM), pH 7.0 including $MgCl_2$ (10 mM) and $CaCl_2$ (2 ml) (buffer B) at 200 µg protein per ml and homogenized with a Polytron at 10,000 rpm for 10 seconds.

Binding assay was performed at 4° C. in a final volume of 1 ml, and with an incubation time of 30 minutes. The radio-ligand [$^3$H]-rac-2-(1,2,3,4-tetrahydro-1-naphthyl)-2-imidazoline was used at a concentration equal to the calculated $K_d$ value of 60 nM to give a total binding at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 µM). Competing ligands were tested in a wide range of concentrations (10 pM-30 µM). The final dimethylsulphoxide concentration in the assay was 2%, and it did not affect radioligand binding. Each experiment was performed in duplicate. All incubations were terminated by rapid filtration through Uni-Filter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 D/well, Packard Instrument Company) and bound radioactivity was counted by a TopCount Microplate Scintillation Counter (Packard Instrument Company).

The preferred compounds show a Ki value (µM) in mouse on TAAR1 in the range of 0.0009-0.01 as shown in the table below.

| Example | Ki (µM) mouse |
|---|---|
| 1 | 0.0061 |
| 2 | 0.0081 |
| 4 | 0.0029 |
| 6 | 0.0018 |
| 7 | 0.0046 |
| 9 | 0.0013 |
| 10 | 0.0045 |
| 18 | 0.0039 |
| 19 | 0.0077 |
| 20 | 0.0059 |
| 21 | 0.0078 |
| 23 | 0.0012 |
| 24 | 0.001 |
| 25 | 0.0055 |
| 26 | 0.0034 |
| 27 | 0.0023 |
| 28 | 0.0031 |
| 31 | 0.0045 |
| 32 | 0.0012 |
| 33 | 0.0028 |

-continued

| Example | Ki (μM) mouse |
|---------|---------------|
| 51 | 0.0009 |
| 52 | 0.004 |
| 53 | 0.0015 |
| 57 | 0.0014 |
| 58 | 0.0014 |
| 62 | 0.0081 |
| 67 | 0.0067 |
| 70 | 0.0082 |
| 73 | 0.0055 |
| 76 | 0.0011 |
| 77 | 0.0053 |
| 78 | 0.0052 |
| 81 | 0.0036 |
| 82 | 0.0012 |
| 101 | 0.003 |
| 102 | 0.006 |
| 109 | 0.0041 |
| 110 | 0.0067 |
| 113 | 0.0024 |
| 114 | 0.0041 |
| 115 | 0.009 |
| 123 | 0.0021 |
| 125 | 0.0044 |
| 128 | 0.0023 |
| 130 | 0.0039 |
| 133 | 0.0077 |
| 139 | 0.0039 |
| 141 | 0.0015 |
| 142 | 0.0079 |
| 149 | 0.0082 |
| 155 | 0.0094 |
| 161 | 0.0072 |
| 170 | 0.0025 |
| 175 | 0.0036 |
| 179 | 0.0026 |
| 181 | 0.0098 |
| 183 | 0.0051 |
| 186 | 0.0089 |
| 188 | 0.0024 |
| 189 | 0.0068 |
| 190 | 0.0014 |
| 192 | 0.001 |
| 193 | 0.008 |
| 194 | 0.0048 |
| 195 | 0.0042 |
| 200 | 0.0028 |
| 202 | 0.0084 |
| 204 | 0.005 |
| 206 | 0.005 |
| 207 | 0.002 |
| 208 | 0.003 |
| 225 | 0.001 |
| 226 | 0.001 |
| 228 | 0.002 |
| 237 | 0.004 |
| 242 | 0.001 |
| 244 | 0.004 |
| 247 | 0.001 |
| 251 | 0.009 |
| 275 | 0.001 |
| 277 | 0.006 |
| 279 | 0.004 |
| 281 | 0.004 |
| 284 | 0.002 |
| 287 | 0.007 |
| 288 | 0.002 |
| 291 | 0.001 |
| 292 | 0.007 |
| 296 | 0.004 |
| 297 | 0.001 |
| 302 | 0.003 |
| 303 | 0.001 |
| 304 | 0.001 |
| 305 | 0.002 |
| 306 | 0.002 |
| 307 | 0.002 |
| 308 | 0.001 |
| 309 | 0.003 |

-continued

| Example | Ki (μM) mouse |
|---------|---------------|
| 312 | 0.001 |
| 324 | 0.002 |
| 325 | 0.002 |
| 327 | 0.002 |
| 331 | 0.001 |
| 333 | 0.001 |

The invention claimed is:

1. A compound of formula I

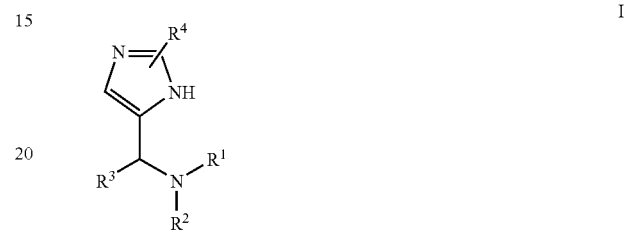

wherein:
R$^1$ is selected from the group consisting of:
  hydrogen;
  lower alkyl;
  —(CR$_2$)$_n$—OH;
  —(CH$_2$)$_n$-aryl, optionally substituted by halogen, lower alkoxy, or lower alkyl substituted by halogen;
  —(CH$_2$)$_n$-heteroaryl, optionally substituted by halogen, lower alkoxy, or lower alkyl substituted by halogen;
  —(CR$_2$)$_n$-cycloalkyl, optionally substituted by hydroxyl;
  —(CH$_2$)$_n$-heterocyclyl;
  —(CH$_2$)$_n$—NH—S(O)$_2$CH$_3$; and
  —(CR$_2$)$_n$O-lower alkyl substituted by halogen;
each R is independently selected from the group consisting of hydrogen and lower alkyl;
R$^2$ is selected from the group consisting of:
  aryl, substituted by one or more substituents, selected from the group consisting of:
    cycloalkyl;
    lower alkoxy substituted by halogen;
    —(CH$_2$)$_n$—S(O)$_2$—NH-lower alkyl;
    —(CH$_2$)$_n$—O-lower alkyl;
    —NHC(O)-lower alkyl;
    —O-tetrahydro-naphthalenyl;
    —(CH$_2$)$_n$-aryl, optionally substituted by-halogen, by aryloxy optionally substituted by halogen, by lower alkoxy, or by lower alkyl substituted by halogen;
    —CH═CH-aryl optionally substituted by halogen;
    —(CH$_2$)$_n$—O-aryl optionally substituted by halogen, lower alkoxy, or lower alkyl substituted by halogen;
    —O—(CH$_2$)$_n$-aryl, optionally substituted by halogen;
    —(CH$_2$)$_n$-heteroaryl,-optionally-substituted by ═O;
    —(CH$_2$)$_n$—O-heteroaryl;
    —(CH$_2$)$_n$-heterocyclyl,-optionally substituted by ═O;
    —(C$_2$)$_n$—O-heterocyclyl, optionally substituted by lower alkyl;
    —S-aryl;
    —CH(OH)-aryl;

—C(CH$_3$)$_2$-aryl;
—NR-aryl; and
2-oxo-2H-pyridin-1-yl;
R$^3$ is selected from the group consisting of: hydrogen and lower alkyl;
R$^4$ is selected from the group consisting of: hydrogen and lower alkyl; and
n is 1, 2, 3 or 4;
or a pharmaceutically active salt thereof.

2. A compound according to claim 1 wherein said compound is a compound of formula IA

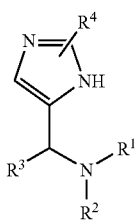

IA wherein:
R$^1$ is selected from the group consisting of:
hydrogen;
lower alkyl;
—(CH$_2$)$_n$-aryl, optionally substituted by halogen, lower alkoxy, or lower alkyl substituted by halogen;
—(CR$_2$)$_n$-cycloalkyl, optionally substituted by hydroxyl;
—(CR$_2$)$_n$—OH;
—(CH$_2$)$_n$-heterocyclyl; and
—(CH$_2$)—NH—S(O)$_2$CH$_3$;
each R is independently selected from the group consisting of: hydrogen and lower alkyl;
R$^2$ is selected from the group consisting of:
aryl, substituted by one or more substituents, selected from the group consisting of:
lower alkoxy substituted by halogen;
—(CH$_2$)$_n$—S(O)$_2$—NH-lower alkyl;
—(CH$_2$)$_n$—O-lower alkyl;
—NHC(O)-lower alkyl;
—(CH$_2$)$_n$-aryl, optionally substituted by halogen, by aryloxy optionally substituted by halogen, by lower alkoxy, or by lower alkyl substituted by halogen;
—S-aryl;
—CH(OH)-aryl;
—C(CH$_3$)$_2$-aryl;
—NR-aryl; and
2-oxo-2H-pyridin-1-yl;
—(CH$_2$)$_n$-heterocyclyl, optionally substituted by =O;
—(CH$_2$)$_n$-heteroaryl; and
—(CH$_2$)$_n$—O-heteroaryl;
R$^3$ is selected from the group consisting of: hydrogen and lower alkyl;
R$^4$ is selected from the group consisting of: hydrogen and lower alkyl; and
n is 1, 2, 3 or 4
or a pharmaceutically active salt thereof.

3. A compound according to claim 2, selected from the group consisting of:
(3H-imidazol-4-ylmethyl)-isopropyl-(4-trifluoromethoxy-phenyl)-amine;
(3-benzyloxy-phenyl)-(3H-imidazol-4-ylmethyl)-isopropyl-amine;
(3H-imidazol-4-ylmethyl)-isopropyl-(3-trifluoromethoxy-phenyl)-amine;
((3-difluoromethoxy-phenyl)-(3H-imidazol-4-ylmethyl)-isopropyl-amine;
(3H-imidazol-4-ylmethyl)-isopropyl-[3-(1,1,2,2-tetrafluoro-ethoxy)-phenyl]-amine;
(3-benzyl-phenyl)-(3H-imidazol-4-ylmethyl)-isopropyl-amine;
N-(1H-imidazol-4-ylmethyl)-N'-phenyl-benzene-1,4-diamine;
{4-[2-(4-chloro-phenyl)-ethyl]-phenyl}-ethyl-(1H-imidazol-4-ylmethyl)-amine;
(3-difluoromethoxy-phenyl)-(3H-imidazol-4-ylmethyl)-methyl-amine;
(3-benzyloxy-phenyl)-(3H-imidazol-4-ylmethyl)-methyl-amine;
(3-benzyloxy-phenyl)-ethyl-(3H-imidazol-4-ylmethyl)-amine;
[3-(3-chloro-phenoxy)-phenyl]-(3H-imidazol-4-ylmethyl)-isopropyl-amine; and
(3H-imidazol-4-ylmethyl)-isopropyl-(3-phenoxymethyl-phenyl)-amine.

4. A compound according to claim 1, wherein R$^1$ is lower alkyl.

5. A compound according to claim 1, wherein R$^1$ is hydrogen.

6. A compound according to claim 1, wherein R$^1$ is CH$_2$-aryl, optionally substituted by halogen, lower alkoxy, or lower alkyl substituted by halogen.

7. A compound according to claim 1, wherein R$^1$ is CRH-cycloalkyl.

8. A pharmaceutical composition comprising a compound of formula I

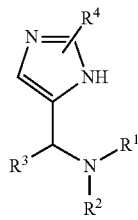

I wherein:
R$^1$ is selected from the group consisting of:
hydrogen;
lower alkyl;
—(CR$_2$)$_n$—OH;
—(CH$_2$)$_n$-aryl, optionally substituted by halogen, lower alkoxy, or lower alkyl substituted by halogen;
—(CH$_2$)$_n$-heteroaryl, optionally substituted by halogen, lower alkoxy, or lower alkyl substituted by halogen;
—(CR2)$_n$-cycloalkyl, optionally substituted by hydroxyl;
—(CH$_2$)$_n$-heterocyclyl;
—(CH$_2$)$_n$—NH—S(O)$_2$CH$_3$; and
—(CR$_2$)O-lower alkyl substituted by halogen;
each R is independently selected from the group consisting of hydrogen and lower alkyl;

$R^2$ is selected from the group consisting of:
aryl, substituted by one or more substituents, selected from the group consisting of:
cycloalkyl;
lower alkoxy substituted by halogen;
—$(CH_2)_n$—$S(O)_2$—NH-lower alkyl;
—$(CH_2)_n$—O-lower alkyl;
—NHC(O)-lower alkyl;
—O-tetrahydro-naphthalenyl;
—$(CH_2)_n$-aryl, optionally substituted by halogen, by aryloxy optionally substituted by halogen, by lower alkoxy, or by lower alkyl substituted by halogen;
—CH=CH-aryl optionally substituted by halogen;
—$(CH_2)_n$-O-aryl optionally substituted by halogen, lower alkoxy, or lower alkyl substituted by halogen;
—O—$(CH_2)_n$-aryl, optionally substituted by halogen;
—$(CH_2)_n$-heteroaryl, optionally substituted by =O;
—$(CH_2)_n$—O-heteroaryl;
—$(CH_2)_n$-heterocyclyl, optionally substituted by =O;
—$(CH_2)_n$—O-heterocyclyl, optionally substituted by lower alkyl;
—S-aryl;
—CH(OH)-aryl;
—$C(CH_3)2$-aryl;
—NR-aryl; and
2-oxo-2H-pyridin-1-yl;

$R^3$ is selected from the group consisting of: hydrogen and lower alkyl;

$R^4$ is selected from the group consisting of: hydrogen and lower alkyl; and n is 1, 2, 3 or 4;

or a pharmaceutically active salt thereof and a pharmaceutically acceptable carrier.

9. A compound selected from the group consisting of (4-chloro-3-trifluoromethyl-phenyl)-(3H-imidazol-4-ylmethyl)-isopropyl-amine;

(3-chloro-4-trifluoromethoxy-phenyl)-(3H-imidazol-4-ylmethyl)-isopropyl-amine;

(3H-imidazol-4-ylmethyl)-isopropyl-naphthalen-2-yl-amine (3H-imidazol-4-ylmethyl)-indan-5-yl-isopropyl-amine;

ethyl-(3H-imidazol-4-ylmethyl)-naphthalen-2-yl-amine;

(4-benzyloxy-3-chloro-phenyl)-(1H-imidazol-4-ylmethyl)-isopropyl-amine;

[3-chloro-4(4-chloro-phenoxy)-phenyl]-ethyl-(1H-imidazol-4-ylmethyl)-amine;

(4-fluoro-3-phenoxy-phenyl)-(3H-imidazol-4-ylmethyl)-isopropyl-amine; and (3-chloro-4-trifluoromethoxy-phenyl)-ethyl-(1H-imidazol-4-ylmethyl)-amine.

* * * * *